United States Patent
Cummings et al.

(10) Patent No.: US 12,213,645 B2
(45) Date of Patent: Feb. 4, 2025

(54) DEVICES, SYSTEMS, AND METHODS FOR CONTROLLING FLUIDS IN ENDOSCOPE SYSTEMS

(71) Applicant: Boston Scientific Scimed, Inc., Maple Grove, MN (US)

(72) Inventors: Nathan T. Cummings, Worcester, MA (US); Shaun D. Comee, Fiskdale, MA (US); Laura E. Richards, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 198 days.

(21) Appl. No.: 17/208,733

(22) Filed: Mar. 22, 2021

(65) Prior Publication Data
US 2021/0298568 A1    Sep. 30, 2021

Related U.S. Application Data

(60) Provisional application No. 62/994,015, filed on Mar. 24, 2020, provisional application No. 62/994,018, (Continued)

(51) Int. Cl.
*A61B 1/00*    (2006.01)
*A61B 1/015*    (2006.01)
(Continued)

(52) U.S. Cl.
CPC .......... *A61B 1/00068* (2013.01); *A61B 1/015* (2013.01); *A61B 1/12* (2013.01);
(Continued)

(58) Field of Classification Search
CPC ............ A61B 1/00068; A61B 1/00082; A61B 1/00091; A61B 1/00094; A61B 1/00119;
(Continued)

(56) References Cited

U.S. PATENT DOCUMENTS 4,061,250 A * 12/1977 Tada ................... B05B 11/1014
251/321
4,694,821 A * 9/1987 Kondo ............... A61B 1/00068
600/158
(Continued)

FOREIGN PATENT DOCUMENTS

EP    2431062 A1    3/2012
JP    2000217777 A    8/2000
(Continued)

OTHER PUBLICATIONS

International Search Report and Written Opinion for the International Patent Application No. PCT/US2021/023479, mailed Jul. 9, 2021, 12 pages.
(Continued)

*Primary Examiner* — Ryan N Henderson
(74) *Attorney, Agent, or Firm* — Seager, Tufte & Wickhem, LLP

(57) ABSTRACT

Various embodiments are generally directed to devices, systems, and methods for controlling the flow of fluids in endoscopic systems, such as endoscopic ultrasound (EUS) enabled endoscopes. Some embodiments are particularly directed to valve sets and/or valve interface mechanisms for controlling air, water, and/or suction flow through a valve well for an endoscopic system. Several embodiments are directed to user interface mechanisms and techniques for enabling an operator to interact with and control endoscope valves. Many embodiments are directed to mechanisms and techniques for translating interface input motion into valve control motions. In one or more embodiments, the valve sets and/or valve interface mechanisms may be disposable.

3 Claims, 61 Drawing Sheets

Related U.S. Application Data filed on Mar. 24, 2020, provisional application No. 62/994,019, filed on Mar. 24, 2020, provisional application No. 62/994,021, filed on Mar. 24, 2020, provisional application No. 62/994,024, filed on Mar. 24, 2020, provisional application No. 62/994,008, filed on Mar. 24, 2020.

(51) Int. Cl.
  *A61B 1/12* (2006.01)
  *F16K 21/20* (2006.01)
  *A61B 1/018* (2006.01)

(52) U.S. Cl.
  CPC .......... *F16K 21/20* (2013.01); *A61B 1/00082* (2013.01); *A61B 1/018* (2013.01)

(58) Field of Classification Search
  CPC . A61B 1/00128; A61B 1/00137; A61B 1/015; A61B 1/018; A61B 1/12; A61B 1/126; A61B 1/127; F16K 21/20
  See application file for complete search history.

(56) References Cited

U.S. PATENT DOCUMENTS

| | | | | |
|---|---|---|---|---|
| 4,800,869 | A * | 1/1989 | Nakajima | A61B 1/00068 600/158 |
| 5,027,791 | A * | 7/1991 | Takahashi | A61B 1/126 600/158 |
| 5,938,589 | A * | 8/1999 | Wako | A61B 1/12 200/5 B |
| 6,334,844 | B1 * | 1/2002 | Akiba | A61B 1/00068 600/156 |
| 6,346,075 | B1 | 2/2002 | Arai et al. | |
| 8,568,303 | B2 * | 10/2013 | Yamane | A61B 1/12 600/156 |
| 9,161,680 | B2 * | 10/2015 | Bellofatto | A61B 1/0011 |
| 2010/0049001 | A1 * | 2/2010 | Yamane | A61B 1/015 600/159 |
| 2011/0208003 | A1 * | 8/2011 | Yamane | A61B 1/12 600/159 |
| 2011/0298169 | A1 * | 12/2011 | Nguyen | A61B 1/125 269/86 |
| 2012/0085956 | A1 * | 4/2012 | Morimoto | A61B 8/445 251/324 |
| 2012/0088973 | A1 * | 4/2012 | Morimoto | A61B 1/00068 600/156 |
| 2012/0088975 | A1 * | 4/2012 | Morimoto | A61B 1/00068 600/159 |
| 2015/0144215 | A1 * | 5/2015 | Bellofatto | F16K 11/0712 137/625.69 |
| 2015/0148608 | A1 * | 5/2015 | Fukushima | A61B 1/00094 600/116 |
| 2016/0302646 | A1 * | 10/2016 | Hamazaki | A61B 1/00 |
| 2018/0361034 | A1 * | 12/2018 | Tobien | F16K 31/5245 |
| 2019/0125167 | A1 * | 5/2019 | Taniguchi | A61B 1/015 |
| 2019/0350441 | A1 * | 11/2019 | Saiga | A61B 1/00068 |
| 2019/0350444 | A1 * | 11/2019 | Saiga | A61B 1/00068 |
| 2019/0350445 | A1 * | 11/2019 | Saiga | G02B 23/2476 |
| 2019/0350446 | A1 * | 11/2019 | Saiga | A61B 1/00068 |
| 2020/0016637 | A1 * | 1/2020 | Still | A61B 1/125 |
| 2020/0187756 | A1 * | 6/2020 | Maurice | A61B 1/126 |
| 2020/0355281 | A1 * | 11/2020 | Harris | A61M 39/16 |
| 2020/0375434 | A1 * | 12/2020 | Scutti | A61B 1/00137 |
| 2020/0386330 | A1 * | 12/2020 | Stanton | F16K 11/0712 |
| 2021/0007586 | A1 * | 1/2021 | Gavalis | A61B 1/015 |
| 2021/0076914 | A1 * | 3/2021 | Arai | G02B 23/24 |

FOREIGN PATENT DOCUMENTS

| | | |
|---|---|---|
| JP | 2007111266 A | 5/2007 |
| WO | 2019225562 A1 | 11/2019 |

OTHER PUBLICATIONS

International Search Report and Written Opinion for the International Patent Application No. PCT/US2021/023482, mailed Jul. 9, 2021, 12 pages.

International Search Report and Written Opinion for the International Patent Application No. PCT/US2021/023484, mailed Jul. 9, 2021, 12 pages.

International Search Report and Written Opinion for the International Patent Application No. PCT/US2021/023478, mailed Jun. 10, 2021, 49 pages.

* cited by examiner

100

SUCTION VALVE ASSEMBLY 102

SUCTION VALVE WELL 104

| SUCTION CHANNEL 106 | WORKING CHANNEL 108 |
| BALLOON CHANNEL 114 | ATMOSPHERIC CHANNEL 116 |

SUCTION VALVE SET 118

| WORKING CHANNEL VALVE 120 | BALLOON VALVE 122 | ATMOSPHERIC VALVE 124 |

VALVE INTERFACE MECHANISM 126

| BIASING MEMBER SET 128 | USER INTERFACE MECHANISM 130 |

AIR/WATER (AW) VALVE ASSEMBLY 202

AW VALVE SET 204

| AIR INPUT CHANNEL 206 | WATER INPUT CHANNEL 208 | AIR OUTPUT CHANNEL 210 |
|---|---|---|
| WATER OUTPUT CHANNEL 212 | BALLOON CHANNEL 214 | ATMOSPHERIC CHANNEL 216 |

AW VALVE SET 218

| PRIMARY CONTROL VALVE 220 | AIR INPUT VALVE 222 | ATMOSPHERIC VALVE 224 |
|---|---|---|

VALVE INTERFACE MECHANISM 226

| BIASING MEMBER SET 228 | USER INTERFACE MECHANISM 230 |
|---|---|

ATMOSPHERIC VALVE OPEN STATE 715-1

1200B

PRIMARY VALVE WATER OUTPUT STATE 1215-2

DEVICES, SYSTEMS, AND METHODS FOR CONTROLLING FLUIDS IN ENDOSCOPE SYSTEMS

PRIORITY

The present application claims the benefit of priority under 35 U.S.C. § 119 to U.S. Provisional Application Ser. Nos. 62/994,008, 62/994,015, 62/994,018, 62/994,019, 62/994,021, and 62/994,024, each filed Mar. 24, 2020, the disclosures of which are incorporated herein by reference in their entirety.

FIELD

The present disclosure relates generally to the field of medical devices. In particular, the present disclosure relates to devices, systems, and methods to control flow through a valve well for an endoscope.

BACKGROUND

An endoscopy procedure is used in medicine to access the interior of a body for diagnostic and/or therapeutic procedures. Oftentimes, the endoscopy procedure uses an endoscope to examine or manipulate the interior of a hollow organ or cavity of the body. Unlike many other medical imaging techniques, endoscopes are inserted directly into the organ. Typically, an endoscope includes one or more channels for the flow of one or more fluids therethrough. For example, one or more of suction, air, and water may flow through an endoscope. A valve assembly may be configured and used in various fashion to control the flow of the one or more fluids through the endoscope. In the case of an echoendoscope or ultrasound endoscope, control of fluids may also be used to inflate and deflate a balloon at the end of an endoscope.

It is with these considerations in mind that a variety of advantageous outcomes may be realized by the devices, systems, and methods of the present disclosure.

SUMMARY

In one aspect, the present disclosure relates to a medical device comprising an air/water (AW) valve set and a valve interface mechanism. The valve set may include a primary control valve, an air input valve, and an atmospheric valve. The primary control valve may be configured to control flow between a water input channel, a water output channel, and a balloon channel of a valve well. The air input valve may be configured to control flow through an air input channel of the valve well. The atmospheric valve may be configured to control flow through an atmospheric channel. In many embodiments, the primary control valve comprises the air input valve. The valve interface mechanism may include a set of one or more biasing members and a user interface mechanism. The user interface mechanism may be operable between a first state, a second state, a third state, and a fourth state. The first state may comprise the valve set configured to place the air input channel in fluid communication with the atmospheric channel, the second state may comprise the valve set configured to place the air input channel in fluid communication with the air output channel, the third state may comprise the valve set configured to place the water input channel in fluid communication with the water output channel, and the fourth state may comprise the valve set configured to place the water input channel in fluid communication with the balloon channel. In various embodiments, the primary control valve comprises a set of radial seals, wherein a first subset of the set of radial seals comprise the air input valve. In various such embodiments, each seal in the first subset of the set of seals may create a seal with one or more portions of the valve interface mechanism. In several embodiments, the primary control valve may comprise a set of seals, wherein a first subset of the set of seals is configured to control flow through the air input channel of the valve well and a second subset of the set of seals is configured to control flow between the water input channel, the water output channel, and the balloon channel of the valve well. In several such embodiments, the set of seals may comprise a set of radial seals with two or more different diameters. In some such embodiments, each seal in a first subset of the set of seals creates a seal with the valve well and each seal in a second subset of the set of seals creates a separate seal with one or more portions of the valve interface mechanism. In many embodiments, the primary control valve comprises a top, a bottom, and a length therebetween, wherein the set of seals are disposed along the length of the primary control valve. In one or more embodiments, the set of seals are concentric. In various embodiments, the primary control valve may comprise a radial seal with a first side and a second side, wherein the first side of the seal is configured to control a flow of air in the valve well and the second side of the seal is configured to control a flow of water in the valve well. In some embodiments, the valve interface mechanism comprises a hat with a top side and a bottom side and the set of one or more biasing members comprise first and second biasing members disposed on the top side of the hat. In several embodiments, the set of one or more biasing members may comprise a cantilever biasing member with a first end and a second end, wherein the first end is coupled to the primary control valve. In some such embodiments, the second end of the cantilever biasing member is disposed in two or more vertical slots comprised in the valve interface mechanism. In many such embodiments, the second end of the cantilever biasing member is disposed in a circumferential slot comprised in the valve interface mechanism. In one embodiment, the primary control valve comprises a duckbill seal. In one such embodiment, the duckbill seal is configured to control flow through the water output channel.

In another aspect, the present disclosure relates to a medical device comprising a suction valve set and a valve interface mechanism. The suction valve set may include a working channel valve, a balloon valve, and an atmospheric valve. The working channel valve may control flow through a working channel of a valve well. The balloon valve may control flow through a balloon channel of the valve well. The atmospheric valve may control flow through an atmospheric channel. The suction valve set may be configurable between a first state, a second state, and a third state. The first state may place the suction channel in fluid communication with the atmospheric channel, the second state may place the suction channel in fluid communication with the working channel, and the third state may place the suction channel in fluid communication with the balloon channel. The valve interface mechanism may include a set of one or more biasing members, an interface member, and a valve mechanism with a top and a bottom. In many embodiments, the bottom of the valve mechanism is coupled to the balloon valve and the working channel valve. In some embodiments, the valve mechanism is configured to move the balloon valve and the working channel valve in unison. Many embodiments comprise a linkage coupled to the bottom of the valve mechanism and the set of one or more biasing members comprise at least one biasing member coupled to the linkage. In several embodiments, at least one biasing member coupled to the linkage comprises a cantilever biasing member. In one or more embodiments, the top of the valve mechanism is coupled to the interface member.

In yet another aspect, the present disclosure relates to a method. The method may include placing an air input channel of a valve well in fluid communication with an atmospheric channel based on operation of a valve interface mechanism to a first state, the valve set comprising a primary control valve, an air input valve, and an atmospheric valve, wherein the primary control valve comprises the air input valve. The method may include placing the air input channel in fluid communication with an air output channel of the valve well based on operation of the valve interface mechanism to a second state. The method may include placing the water input channel in fluid communication with a water output channel of the valve well based on operation of the valve interface mechanism to a third state. The method may include placing the water input channel in fluid communication with the balloon channel of the valve well based on operation of the valve interface mechanism to a fourth state. In some embodiments, the method may include rotating an interface member in a first direction to operate the user interface mechanism to the second state and rotating the interface member in a second direction to operate the user interface mechanism to the third state and/or fourth state. In many embodiments, the method may include rotating the interface member adjust one or more valves in an air/water valve set via a cam. In several embodiments, the method may include operating one or more of a lever, a rocker switch, and an interface member to adjust between one or more of the first state, the second state, the third state, and the fourth state.

In still another aspect, the present disclosure relates to a method. The method may include configuring a valve set to place an air input channel of a valve well in fluid communication with an atmospheric channel based on operation of a valve interface mechanism to a first state, the valve set comprising a primary control valve, an air input valve, and an atmospheric valve, wherein the primary control valve comprises the air input valve. The method may include configuring the valve set to place the air input channel in fluid communication with an air output channel of the valve well based on operation of the valve interface mechanism to a second state. The method may include configuring the valve set to place the water input channel in fluid communication with a water output channel of the valve well based on operation of the valve interface mechanism to a third state. The method may include configuring the valve set to place the water input channel in fluid communication with the balloon channel of the valve well based on operation of the valve interface mechanism to a fourth state. In some embodiments, the method may include configuring a set of seals along a length of the primary control valve to control flow through the air input channel of the valve well. In various embodiments, the method may include configuring a first side of a radial seal comprised in the primary control valve to control a flow of air through the valve well and configuring a second side of the radial seal comprised in the primary control valve to control a flow of water through the valve well.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 1 includes a block diagram of an exemplary suction valve assembly, according to one or more embodiments described herein.

FIG. 2 includes a block diagram of an exemplary air/water (AW) valve assembly, according to one or more embodiments described herein.

DETAILED DESCRIPTION

Figure 3A:
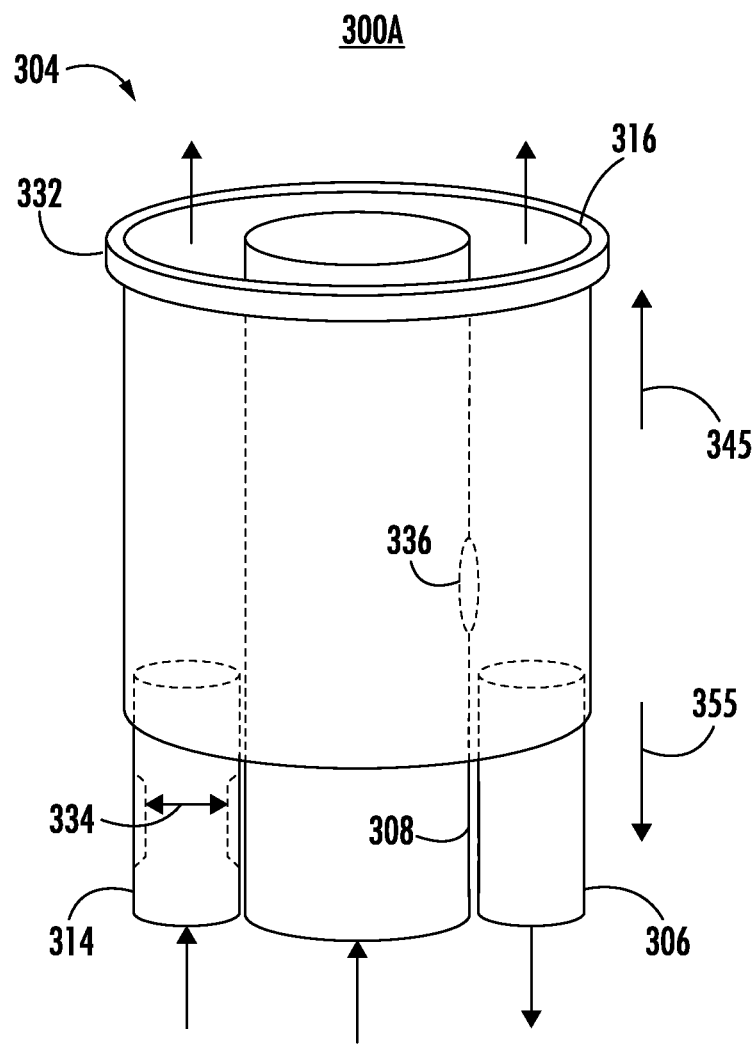
FIGS. 3A-3D illustrate various aspects of an exemplary suction valve well, according to one or more embodiments described herein.

Various embodiments are generally directed to devices, systems, and methods for controlling the flow of fluids in endoscopic systems, such as endoscopic ultrasound (EUS) enabled endoscopes. Some embodiments are particularly directed to valve sets and/or valve interface mechanisms for controlling air, water, and/or suction flow through a valve well for an endoscopic system. Several embodiments are directed to user interface mechanisms and techniques for enabling an operator to interact with and control endoscope valves. Many embodiments are directed to mechanisms and techniques for translating interface input motion into valve control motions. In one or more embodiments, the valve sets and/or valve interface mechanisms may be disposable. These and other embodiments are described and claimed.

Some challenges when controlling the flow of fluids through endoscopes include unreliable valves prone to failure. For example, many valves and valve interface mechanisms are fragile and likely to leak. These issues can be compounded when the components are designed, constructed, and/or assembled economically to facilitate disposal after a single use. Alternatively, these issues can be compounded when reusable components are worn down from multiple use/cleaning cycles. Adding further complexity, user interface mechanisms may be confusing to operate and require a steep learning curve. For instance, delicate and nonintuitive movements may be required to accurately control fluid flows. Further, little or no feedback may be provided to indicate how a set of valves is arranged. For example, an operator may not be able to easily discern via a user interface mechanism whether the set of valves is arranged to provide suction to a working channel or provide suction to a balloon channel. These and other factors may result in devices, systems, and methods for controlling the flow of fluids through endoscopes that are difficult to use, inaccurate, inefficient, and unreliable, resulting in limited applicability and/or uncertain outcomes. Such limitations can drastically reduce the dependability, ergonomics, and intuitiveness of flow control in endoscopes and procedures performed therewith, contributing to reduced usability, adverse outcomes, excess fatigue, and lost revenues.

Various embodiments described herein include one or more components of a valve assembly, such as valves and/or valve interface mechanisms, that provide reliable and intuitive control of fluid flow through endoscopes. In several embodiments, the components may provide reliable operation while providing sufficient value to be disposable (e.g., single-use). In many embodiments, the components may provide accurate and intuitive interfaces to improve operator experience. For example, embodiments may utilize one or more of up-and-down, forward-and-back, side-to-side, and rotational interfaces to provide ergonomic and intuitive control of fluid flows through endoscopes. Some such embodiments may include one or more interface members, such as push/pull switches, bellows, rotational switches, knobs, buttons, and toggle switches. In many embodiments, one or more of the components may provide/enable tactile feedback. For example, one or more components of the valve interface mechanism may provide tactile or haptic feedback to indicate how a set of valves is arranged (e.g., arranged to permit/block flows between various channels). In some examples, the force to operate a user interface mechanism may vary to indicate transitions between valve states. In various embodiments, tactile feedback may be produced as a result of different components of a valve assembly coming into contact, such as due to received input.

In various embodiments, one or more of the components may be designed to simplify manufacturability. For instance, the location of one or more biasing members may simplify component assembly. In these and other ways, components/ techniques described here may improve operator experience, decrease learning curves, improve reliability, and/or decrease manufacturing complexity via realization of more efficient and valuable devices, systems, and methods for controlling the flow of fluids in endoscopic systems. In many embodiments, one or more of the advantageous features may result in several technical effects and advantages over conventional technology, including increased capabilities and improved adaptability.

The present disclosure is not limited to the particular embodiments described. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure may be described with specific reference to specific medical devices and systems (e.g., an endoscope), it should be appreciated that such medical devices and systems may be used in a variety of medical procedures which require navigating one or more accessory tools through ductal, luminal, or vascular anatomies, including, for example, interventional radiology procedures, balloon angioplasty procedures, thrombolysis procedures, angiography procedures, Endoscopic Retrograde Cholangio-Pancreatography (ERCP) procedures, and the like. The disclosed medical devices and systems may be inserted via different access points and approaches, e.g., percutaneously, endoscopically, laparoscopically or some combination thereof.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional/operator when introducing a device into a patient, while the term "proximal" refers to the end closest to the medical professional when introducing a device into a patient.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. In other instances, well known structures and devices are shown in block diagram form to facilitate a description thereof. The intention is to cover all modification, equivalents, and alternatives within the scope of the claims.

FIGS. 1 and 2 illustrate block diagrams of exemplary valve assemblies in environments 100, 200, according to one or more embodiments described herein. In some embodiments, one or more components of environment 100 and/or environment 200 may be the same or similar to one or more other components described herein. Environment 100 may include a suction valve assembly 102 with a suction valve well 104, a suction valve set 118, and a valve interface mechanism 126. Environment 200 may include an air/water (AW) valve assembly 202 with an AW valve well 204, an AW valve set 218, and a valve interface mechanism 226. In one or more embodiments described herein, various components of suction valve assembly 102 and/or AW valve assembly 202 may interoperate to provide reliable and intuitive control of fluid flow through endoscopic systems. For example, one or more components of valve sets 118, 218 and valve interface mechanisms 126, 226 may provide reliable and intuitive control of fluid flow through suction valve well 104 or AW valve well 204. In many embodiments, components of a valve assembly may be classified as, belong to, include, implement, and/or interoperate with one or more of a valve well, a valve set, and a valve interface mechanism. For instance, a valve interface mechanism may include one or more portions of a valve. Embodiments are not limited in this context.

In environment 100, the suction valve well 104 may include suction channel 106, working channel 108, balloon channel 114, and atmospheric channel 116; the suction valve set 118 may include working channel valve 120, balloon valve 122, and atmospheric valve 124; and the valve interface mechanism 126 may include biasing member set 128 and user interface mechanism 130. In various embodiments, the channels of the suction well 104 may be connected to other components in an endoscopic system, such as via tubing or piping. In one or more embodiments described herein, the suction channel 106 may be connected to a suction source, the working channel 108 may be connected to a working channel of an endoscopic device (e.g., endoscope or component disposed therethrough), the balloon channel 114 may be connected to a balloon of an endoscopic device. In several embodiments, suction valve set 118 and valve interface mechanism 126 may control the flow of suction (e.g., induced by negative pressure relative to atmospheric pressure) through suction valve well 104. In several such embodiments, the flow of suction may be controlled to the suction channel 106 from one of the working channel 108, the balloon channel 114, and the atmospheric channel 116.

In environment 200, the AW valve well 204 may include air input channel 206, water input channel 208, air output channel 210, water output channel 212, balloon channel 214, and atmospheric channel 216; the AW valve set 218 may include primary control valve 220, air input valve 222, and atmospheric valve 224; and the valve interface mechanism 226 may include biasing member set 228 and user interface mechanism 230. In various embodiments, the channels of the AW well 204 may be connected to other components in an endoscopic system, such as via tubing or piping. In one or more embodiments described herein, the air input channel 206 may be connected to a pressurized air source, the water input channel 208 may be connected to a water source, the air output channel 210 may be connected to an air channel of an endoscopic device (e.g., endoscope or component disposed therethrough), the water output channel 212 may be connected to a water channel of an endoscopic device, and the balloon channel 214 may be connected to a balloon of an endoscopic device. In several embodiments, AW valve set 218 and valve interface mechanism 226 may control the flow of air and water through AW valve well 204. In several such embodiments, the flow of air may be controlled from air input channel 206 to one of the air output channel 210, the atmospheric channel 216, or blocked, and/or the flow of water may be controlled from water input channel 208 to one of water output channel 212, the balloon channel 214, or blocked.

In many embodiments, suction valve assembly 102 and/or AW valve assembly 202 may be used in conjunction with an endoscopic system, such as an EUS system. In various embodiments, reference to a balloon may refer to a balloon in the EUS system that can be inflated/deflated to provide medium to facilitate transmission of sound waves and capturing of ultrasound images. For example, valve interface mechanism 126 may receive input to control the flow through suction valve well 104 to deflate the balloon by arranging the suction valve set 118 to place the suction channel 106 in fluid communication with the balloon channel 114. In another example, valve interface mechanism 226 may receive input to control the flow of water through AW valve well to inflate the balloon by arranging the AW valve set 218 to place the water input channel 208 in fluid communication with balloon channel 214. In other embodiments, one or more of the components of the valve assembly for AW and/or suction may be implemented in configurations that do not require or include a balloon, such as video capable scope with ultrasound functionality.

More generally, in several embodiments, each channel in a valve well may refer to a flow path comprising an input/output of a fluid from/to a corresponding entity. For example, suction channel 106 may refer to a flow path comprising an input from a suction source. In another example, an atmospheric channel may refer to a flow path comprising an output to the atmosphere. These and other aspects of the present disclosure will be described in more detail below, such as with respect to FIGS. 3A-4E. In various embodiments, each valve in a valve set may refer to a component that physically controls flow through or between one or more channels. For instance, when closed, the atmospheric valve 124 may block the flow of air out of the atmospheric channel 116. In another instance, in a first position, or first state, the primary control valve 220 may place the water input channel 208 in fluid communication with the water output channel 212, and in a second position, the primary control valve 220 may place the water input channel 208 in fluid communication with the balloon channel 214. These and other aspects of the present disclosure will be described in more detail below, such as with respect to FIGS. 5-12C.

In various embodiments, the valve interface mechanisms may include one or more components to enable control over the arrangement of valves in a valve set. In such embodiments, biasing member sets may include one or more, torsional springs, lever springs, coil spring, baffles, dampers, clips, and the like that provide a force to bias one or more components in a specific direction or position. For example, the biasing member set 228 may cause air to flow out the atmospheric channel when no input is being received. In an additional, or alternative example, the biasing member set 128 may provide differing resistance to operation of the user interface mechanism 130 between different states, such as to provide tactile indications of the state. In various embodiments, each of the user interface mechanisms 130, 230 may include one or more of an interface, an interface member, a user interface, a housing, a linkage, a knob, a lever, a rocker switch, a push/pull switch, a knob, a button, a diaphragm switch, a toggle switch, and the like. In some embodiments, an interface, an interface member, and/or a user interface may be the same or similar.

In several embodiments, user interface mechanisms may include one or more components to receive input and/or implement valve arrangements. For example, user interface mechanism 130 may include a user interface comprising a lever and one or more linkages to translate motion of the lever into appropriate motion of one or more valves to achieve a desired flow. In various embodiments, user interface mechanisms may include one or more biasing members and/or biasing members may include one or more user interface mechanisms. It will be appreciated that one or more components described herein in the context of a suction valve assembly may be utilized in or adapted for use in an AW valve assembly, and vice versa, without departing from the scope of this disclosure. For example, a rotational user interface mechanism described with respect to a suction valve interface mechanism may be utilized in or adapted for use in an AW valve interface mechanism. These and other aspects of the present disclosure will be described in more detail below.

FIGS. 3A-4E illustrate various aspects of exemplary valve well block diagrams of exemplary valve assemblies in environments 300A-D, 400A-E, according to one or more embodiments described herein. In some embodiments, one or more components of FIGS. 3A-4E may be the same or similar to one or more other components described herein. Environments 300A-D illustrate a suction valve well 304 comprising a suction channel 306, a working channel 308, a balloon channel 314 and an atmospheric channel 315. Environments 400A-E illustrate an AW valve well 404 with an air input channel 406, a water input channel 408, an air output channel 210, a water output channel 212, a balloon channel 214, and an atmospheric channel 216. In one or more embodiments described herein, fluid may flow through the valve wells based on the arrangement of one or more valves as positioned by one or more valve interface mechanisms. Embodiments are not limited in this context.

Referring to FIG. 3A, environment 300A illustrates various components of suction valve well 304. The suction valve well 304 may include a top 345 and a bottom 335. The suction channel 306, working channel 308, and balloon channel 314 may comprise respective entrances/exits towards the bottom 355 while the atmospheric channel 316 may comprise an entrance towards the top 345. In the illustrated embodiment, the balloon channel 314 includes a necking portion 334, the working channel 308 includes a well radial hole 336, and the atmospheric channel 316 includes a lip 332. In one or more embodiments, the necking portion 334 may enable a valve to prevent fluid flow through the balloon channel 314, such as by blocking the necking portion 334. In various embodiments, the well radial hole 336 may enable the working channel 308 to be placed in fluid communication with the suction channel 306. In several embodiments, the lip 332 may enable one or more suction valve sets and/or valve interface mechanisms to couple to the suction valve well 304. In many embodiments, valves and/or valve interface mechanisms may be inserted through atmospheric channel 316 for assembly of a suction valve assembly. It will be appreciated that the orientation and/or arrangement of one or more of the channels and/or flows may be modified in various embodiments without departing from the scope of this disclosure.

Figure 3B:
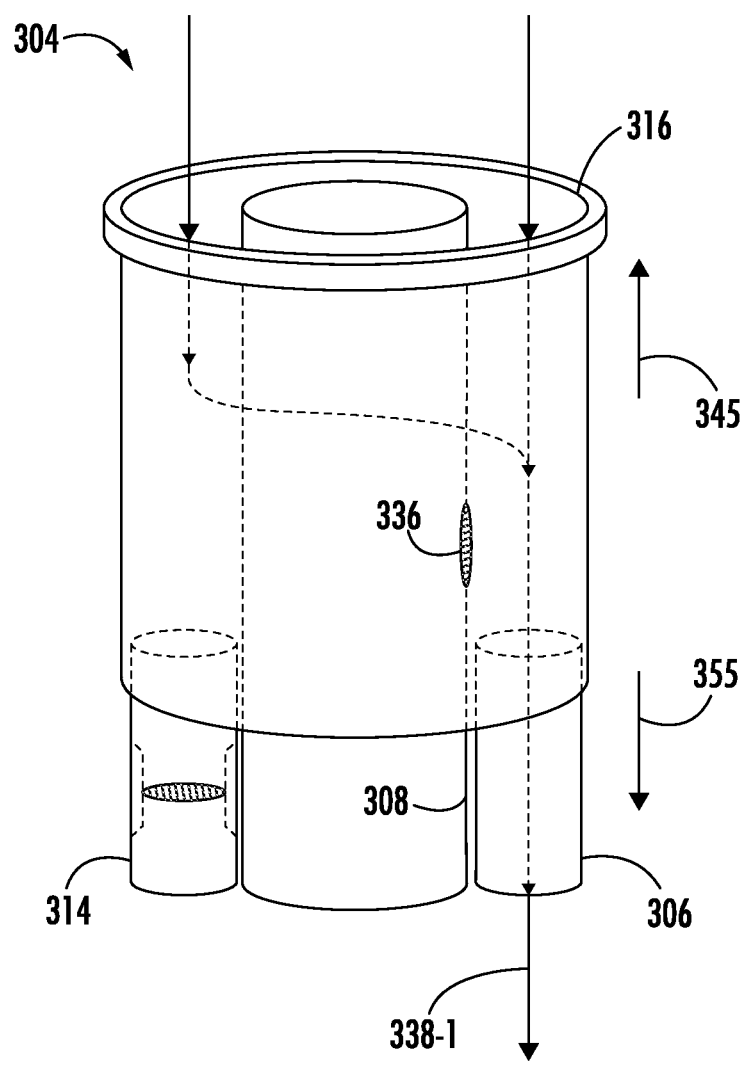

Referring to FIG. 3B, environment 300B illustrates a flow 338-1 through the suction valve well 304 in an atmospheric suction state 305-1. In the atmospheric suction state 305-1, flow 338-1 may enter via the atmospheric channel 316 and exit through the suction channel 306. For example, suction channel 306 may be an input in the handle of a medical scope that is connected to a vacuum system, such as for a hospital, home, and/or mobile device.

Further, in some embodiments, flow may be blocked through the balloon channel 314 at the necking portion 334 and flow may be blocked through the working channel 308 at the well radial hole 336. As will be discussed in more detail below, in operation, fluid communication with the atmosphere may be provided through a passage/channel in, or created by, one or more components (e.g., a valve inserted into the atmospheric channel 316). Further, one or more components may be used to seal portions of the atmospheric channel 316 to facilitate blocking of fluid communication with the atmosphere by an atmospheric valve.

Figure 3C:
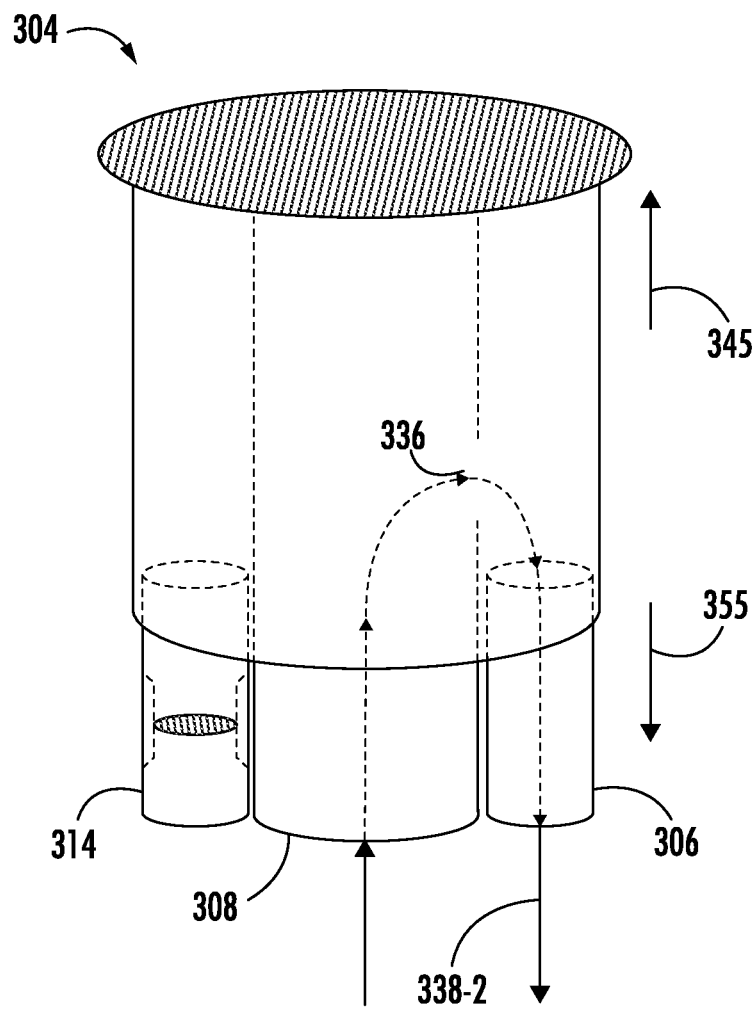

Referring to FIG. 3C, environment 300C illustrates a flow 338-2 through the suction valve well 304 in a working channel suction state 305-2. In the working channel suction state 305-2, flow 338-2 may enter via the working channel 308, pass through the well radial hole 336, and exit through the suction channel 306. Further, in many embodiments, flow may be blocked through the balloon channel 314 at the necking portion 334 and flow may be blocked through the atmospheric channel 316.

Figure 3D:
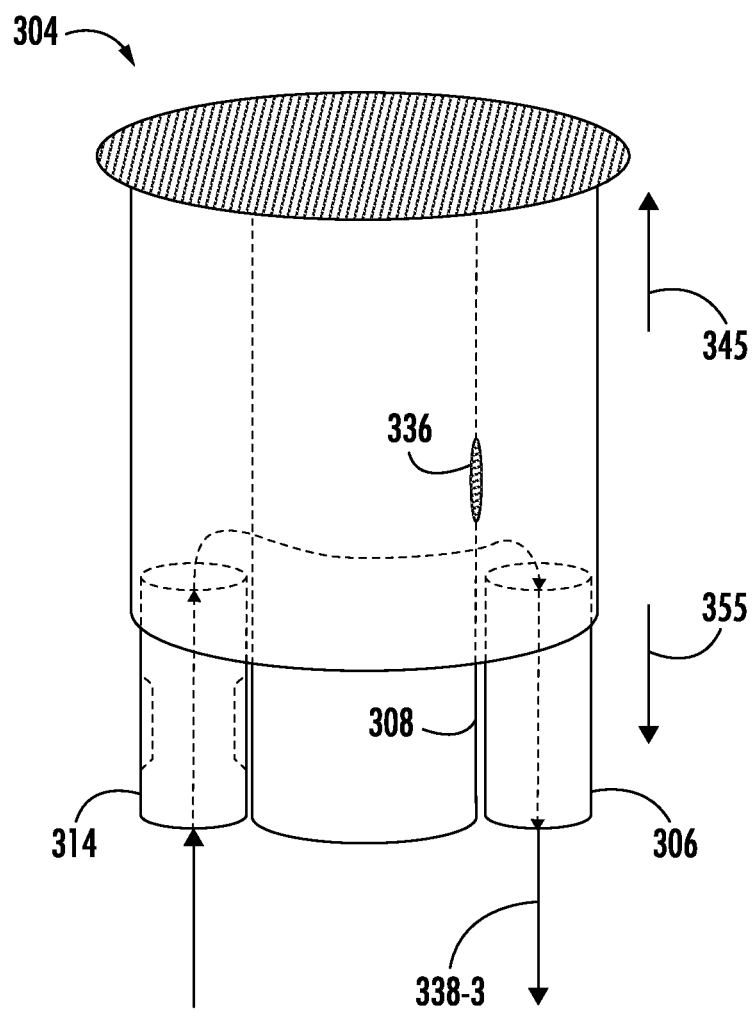

Referring to FIG. 3D, environment 300D illustrates a flow 338-3 through the suction valve well 304 in a balloon channel suction state 305-3. In the balloon channel suction state 305-3, flow 338-3 may enter via the balloon channel 314 and exit through the suction channel 306. Further, in several embodiments, flow may be blocked through the working channel 308 at the well radial hole 336 and may be blocked through the atmospheric channel 316.

Figure 4A:
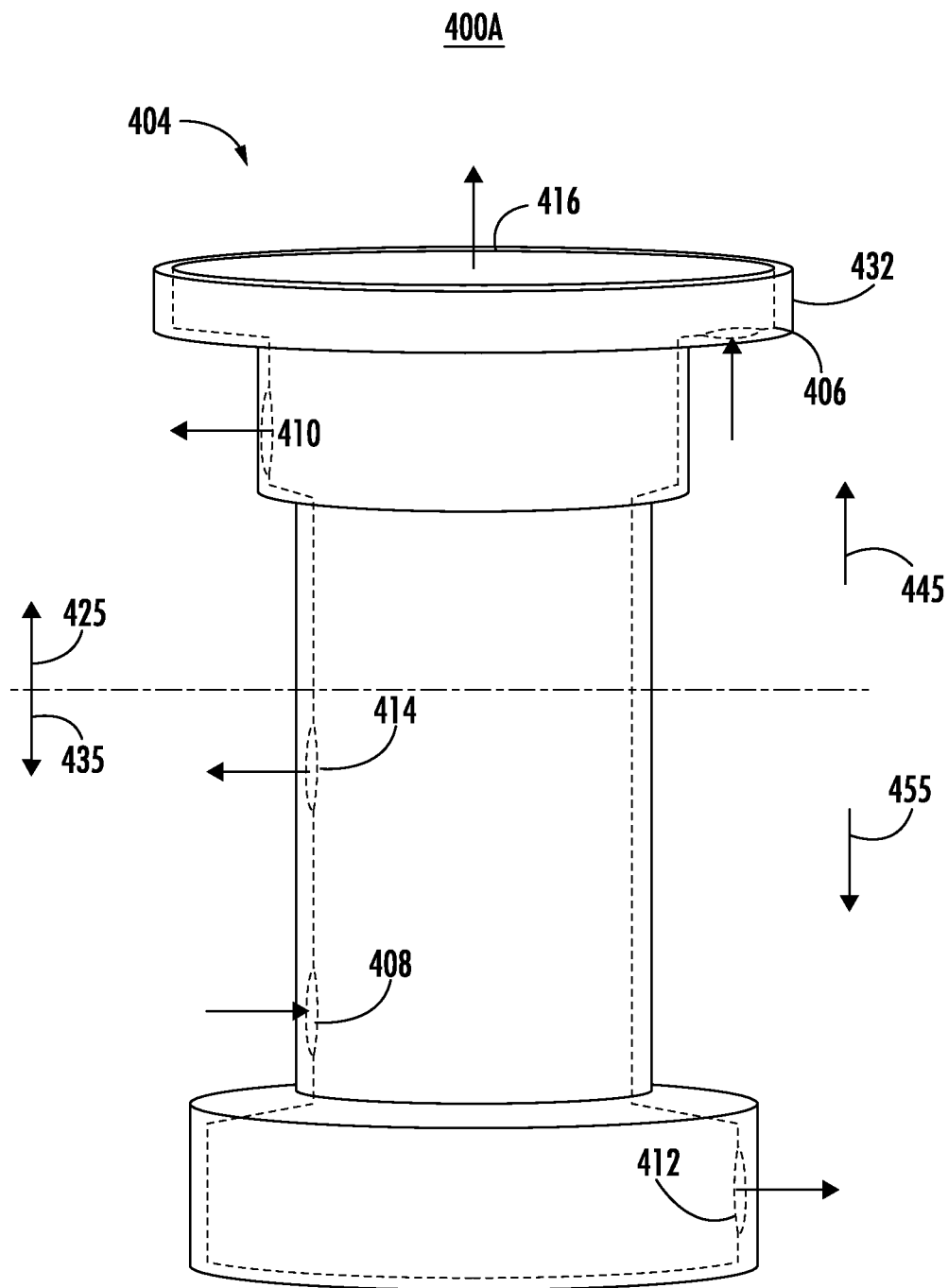
FIGS. 4A-4E illustrate various aspects of an exemplary AW valve well, according to one or more embodiments described herein.

Referring to FIG. 4A, environment 400A illustrates various components of AW valve well 404. The AW valve well 404 may include a top 445 and a bottom 435 and/or an air portion 425 and a water portion 435. The air output channel 410, air input channel 412, and atmospheric channel 416 may be in the air portion 425. The atmospheric channel 416 may comprise a horizontally-oriented exit towards the top 345 and lip 432, the air input channel 412 may comprise a horizontally-oriented entrance towards the top 345, the air output channel 410 may comprise a vertically-oriented exit towards the top. The water input channel 408, water output channel 412, and balloon channel 414 may be in the water portion 435. The balloon channel 414 may comprise a vertically-oriented exit proximate the middle, the water input channel 408 may comprise a vertically-oriented entrance toward the bottom 455, and the water output channel 412 may comprise a vertically-oriented exit toward the bottom 455. In several embodiments, the lip 432 may enable one or more suction valve sets and/or valve interface mechanisms to couple to the AW valve well 404.

In several embodiments, the AW valve well 404 may change diameters one or more times. For example, the diameter changes in conjunction with vertical displacement of a valve may enable flow around the valve and through a channel. In the illustrated embodiment, the AW valve well may have a first diameter comprising the entrance/exits of the air input/atmospheric channels 412, 416, a second diameter comprising the exit of the air output channel 410, a third diameter comprising the entrance/exit of the water input/balloon channels 408, 414, and a fourth diameter comprising the exit of the water output channel 412. It will be appreciated that the orientation, size, and/or arrangement of one or more of the channels and/or flows may be modified in various embodiments without departing from the scope of this disclosure.

Figure 4B:
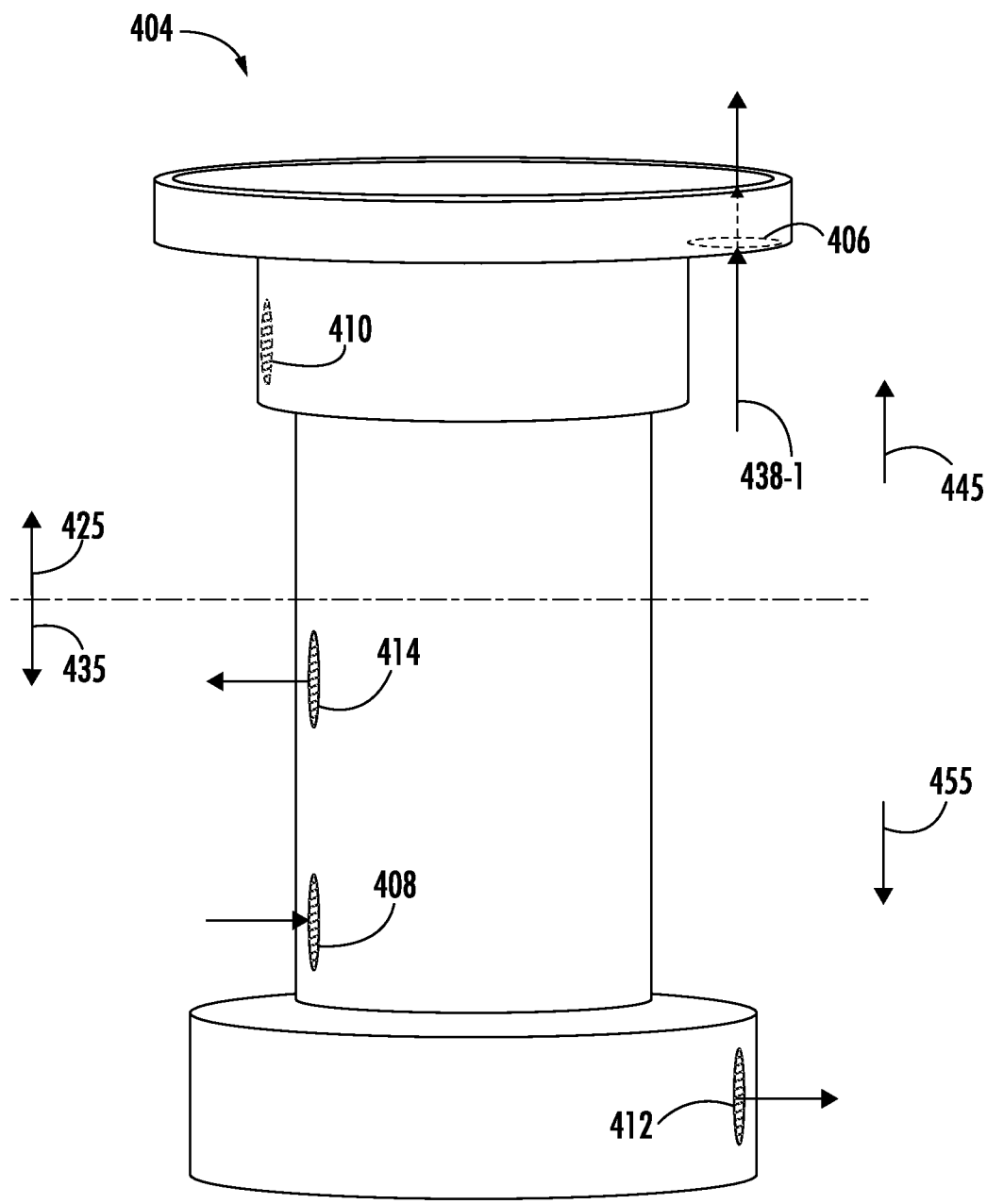

Referring to FIG. 4B, environment 400B illustrates a flow 438-1 through the AW valve well 404 in an air escape state 405-1. In the air escape state 405-1, flow 438-1 may enter via air input channel 406 and exit through the atmospheric channel 416. Further, in some embodiments, flow may be blocked through one or more of balloon channel 414, water input channel 408, and water output channel 412.

Figure 4C:
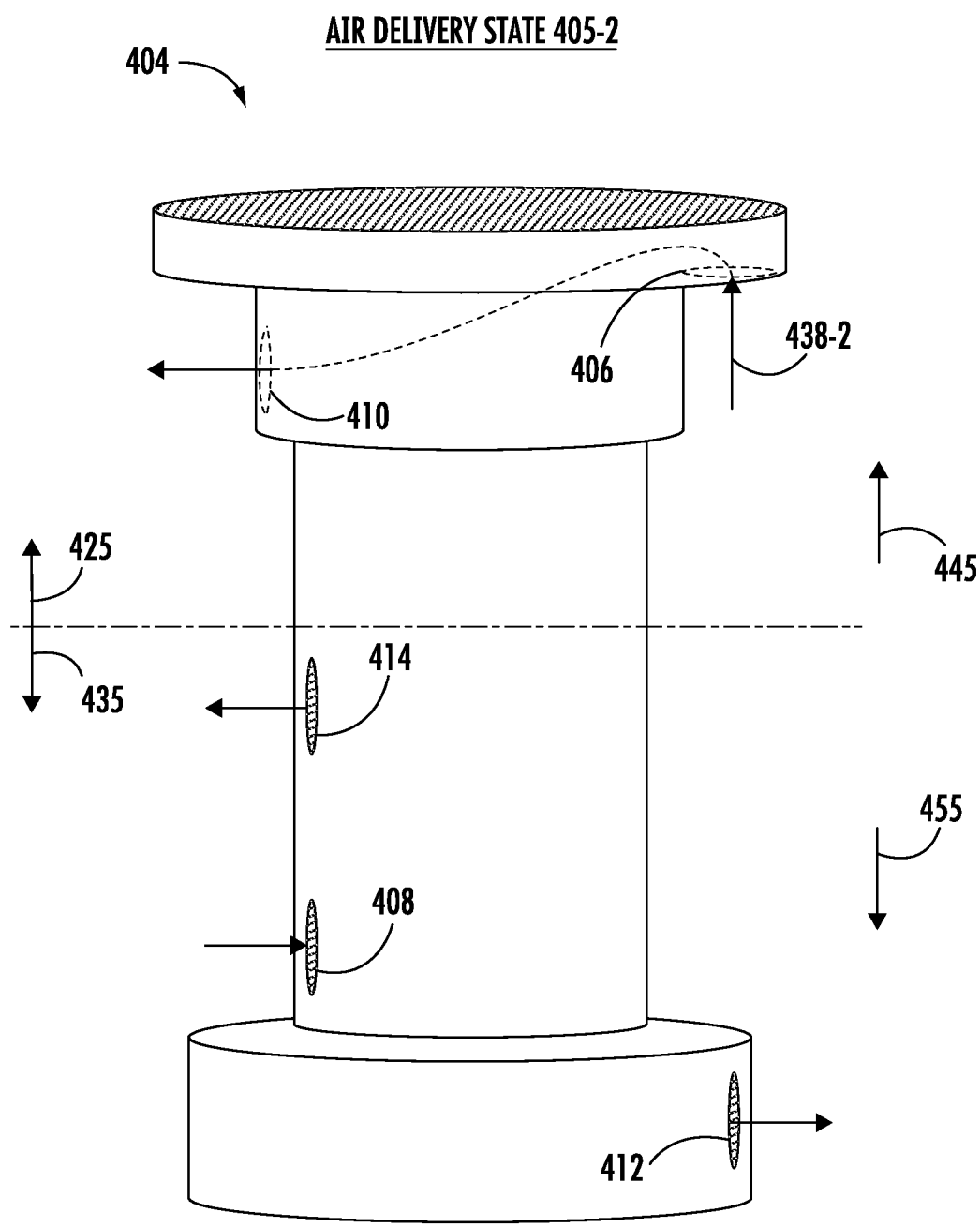

Referring to FIG. 4C, environment 400C illustrates a flow 438-2 through the AW valve well 404 in an air delivery state 405-2. In the air delivery state 405-2, flow 438-2 may enter via the air input channel 406 and exit through the air output channel 410. Further, in various embodiments, flow may be blocked through one or more of atmospheric channel 416, balloon channel 414, water input channel 408, and water output channel 412.

Figure 4D:
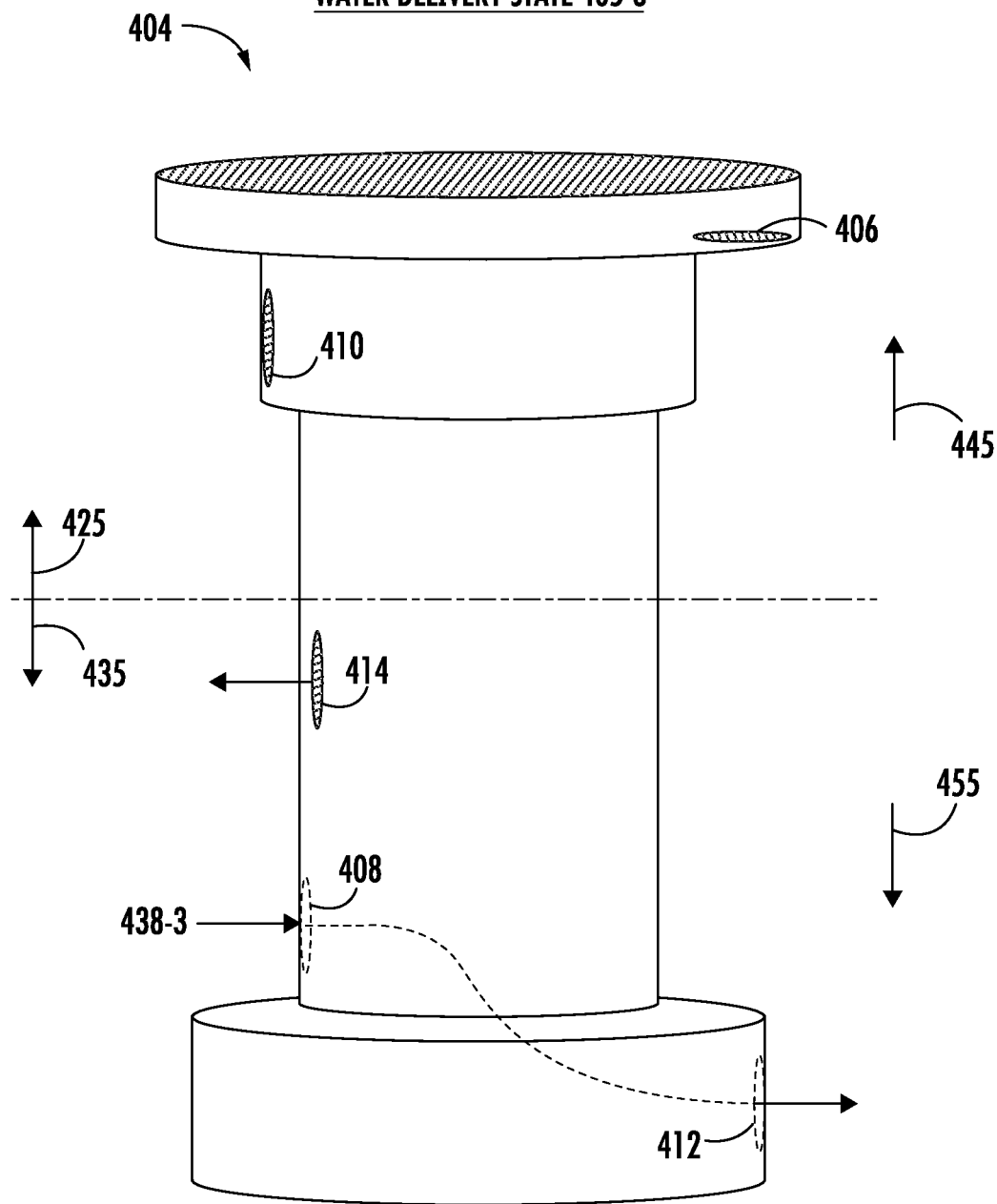

Referring to FIG. 4D, environment 400D illustrates a flow 438-3 through the AW valve well 404 in a water delivery state 405-3. In the water delivery state 405-3, flow 438-3 may enter via water input channel 408 and exit through the water output channel 412. Further, in various embodiments, flow may be blocked through one or more of the balloon channel 414, air output channel 410, air input channel 406, and atmospheric channel 416. In various embodiments, blocking flow at the air input channel 406 may cause pressure to build in a water source feeding the water input channel 408. In various such embodiments, pressure in the water source may cause fluid to flow from the water source to water input channel 408.

Figure 4E:
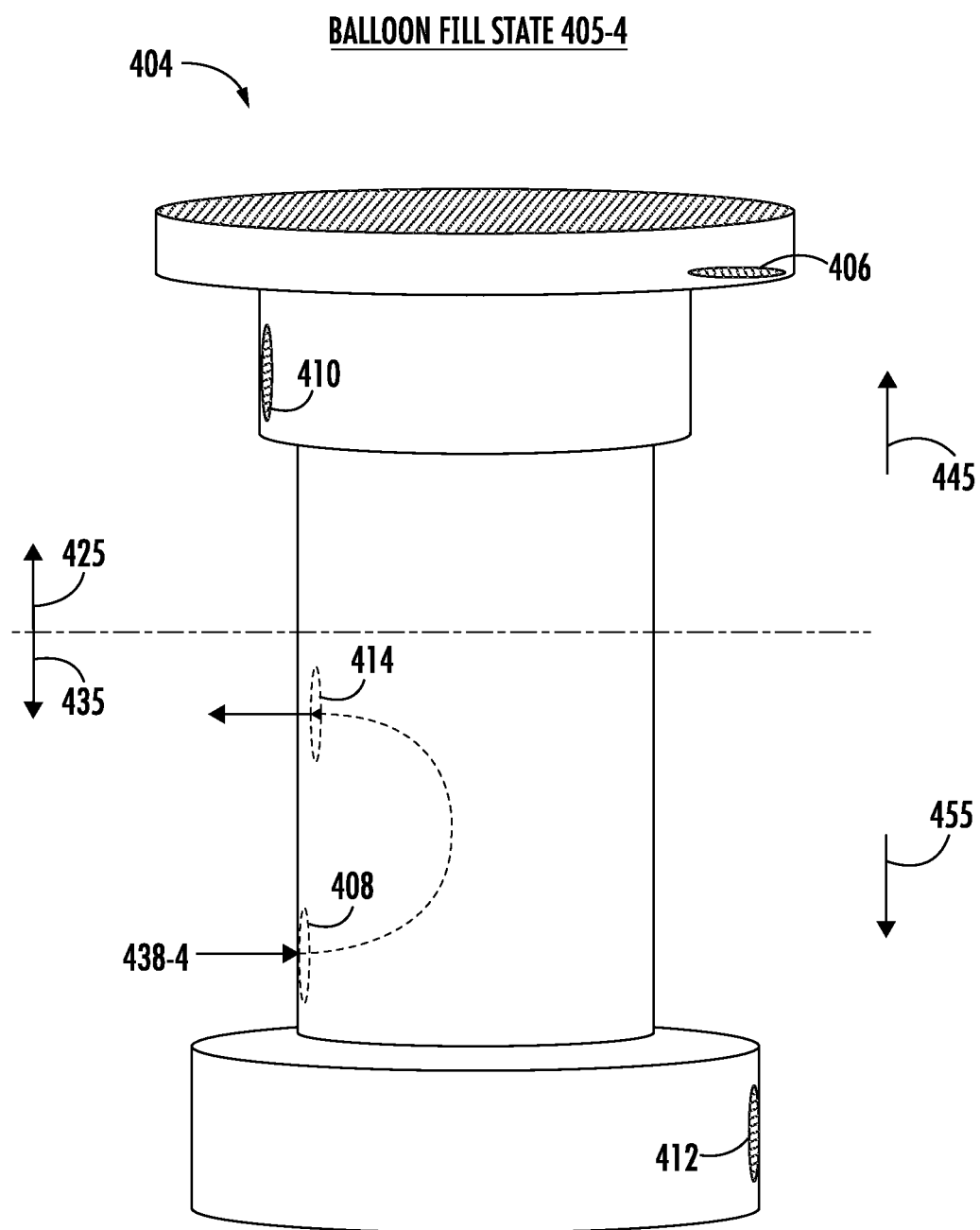

Referring to FIG. 4E, environment 400E illustrates a flow 438-4 through the AW valve well 404 in a balloon fill state 405-4. In the balloon fill state 405-4, flow 438-4 may enter via the water input channel 408 and exit through the balloon channel 414. Further, in many embodiments, flow may be blocked through one or more of the water output channel 412, air output channel 410, air input channel 406, and atmospheric channel 413.

FIGS. 5-12C illustrate various aspects of exemplary valve sets in environments 500, 600A, 600B, 700A, 700B, 800A-C, 900, 1000A, 1000B, 1100A, 1100B, 1200A-C, according to one or more embodiments described herein. In some embodiments, one or more components of FIGS. 5-12C may be the same or similar to one or more other components described herein. Environments 500-800C illustrate various aspects of a suction valve set 518 in conjunction with one or more components of suction valve well 304. Environments 900-1200C illustrate various aspects of an AW valve set 918 in conjunction with one or more components of AW valve well 404. In one or more embodiments described herein, fluid may flow through the valve wells based on the arrangement of one or more valves as positioned by one or more valve interface mechanisms. In many embodiments, one or more valves described herein may include a plurality of components configured to control fluid through a valve well. Embodiments are not limited in this context.

Figure 5:
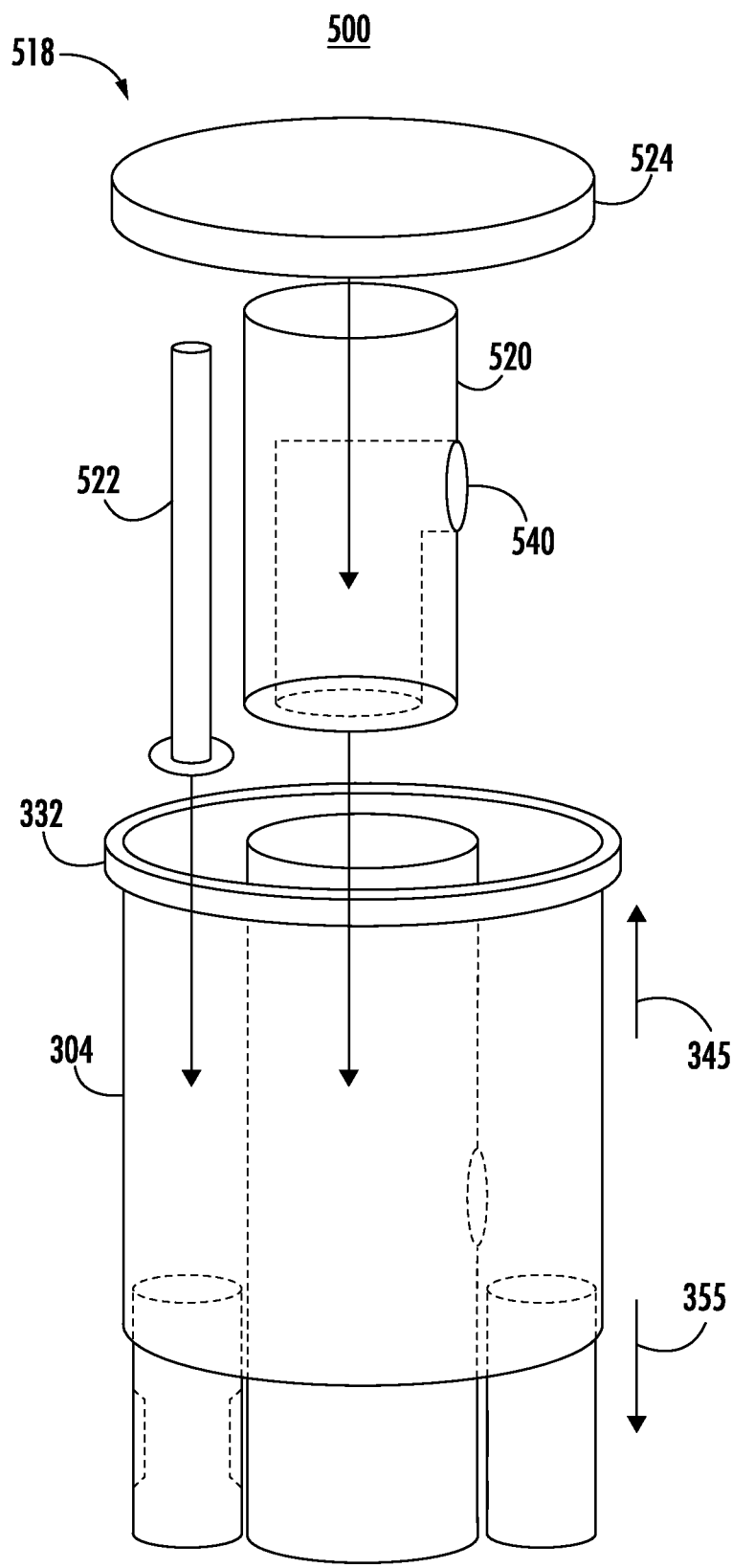
FIG. 5 illustrates an exemplary suction valve set, according to one or more embodiments described herein.

Referring to FIG. 5, environment 500 illustrates suction valve set 518 in conjunction with suction valve well 304. Suction valve set 518 may include working channel valve 520, balloon valve 522, and atmospheric valve 524. The working channel valve 520 may include a working channel valve radial hole 540 that enables fluid to flow into the working channel valve 520 out of the bottom of the working channel valve 520. In several embodiments, the working channel valve 520 may be inserted into the working channel of suction valve well 304 to control flow therethrough. The balloon valve 522 may be inserted into balloon channel 314 of suction valve well 304 to control flow therethrough. The atmospheric valve 524 may be inserted into the atmospheric channel of suction valve well 304 to control flow therethrough. In many embodiments, one or more valves in suction valve set 518 may be integrated with one or more portions of a housing and/or valve interface mechanism corresponding to suction valve well 304.

In one or more embodiments, the atmospheric valve 524 may be configured to control fluid communication with the atmosphere from the interior of the suction valve well 304. In many embodiments, the atmospheric valve 524 may include a hole in a housing. In some embodiments, the atmospheric valve 524 may be operated by covering and/or uncovering the hole, such as with a finger or other mechanism. In several embodiments, the positioning and/or configuration of the valves in suction valve set 518 may be controlled by one or more components of a corresponding valve interface mechanism. For example, depressing a valve interface mechanism to a first stop may simultaneously shut off atmospheric suction via a seal on the underside of a cap and open working channel suction by pushing down the center of the working channel valve 520 to align the working channel valve radial hole 540 and the well radial hole.

Figure 6A:
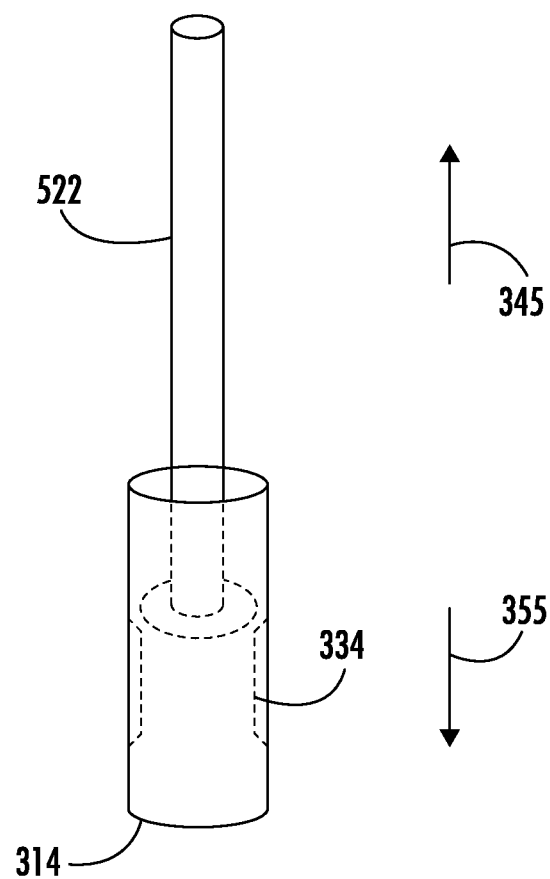
FIGS. 6A-8C illustrate various aspects of exemplary valves in suction valve sets, according to one or more embodiments described herein.
Figure 6B:
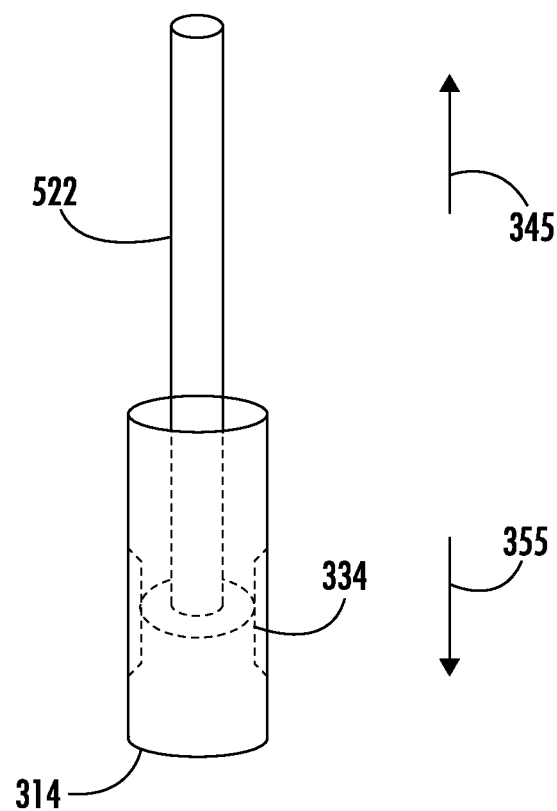

Referring to FIG. 6A, environment 600A illustrates a balloon valve open state 615-1. In the balloon valve open state 615-1, the balloon valve 522 may allow flow through the balloon channel 314 by permitting flow through the necking portion 334 of balloon channel 314. Referring to FIG. 6B, environment 600B illustrates a balloon valve sealed state 615-2. In the balloon valve sealed state 615-2, the balloon valve 522 may prevent flow through balloon channel 314 by blocking flow through the necking portion 334 of balloon channel 314. In additional, or alternative embodiments, the default state of the balloon valve 522 may be the balloon valve sealed state 615-2 and the balloon valve 522 may be depressed toward the bottom 355 and below the necking portion 334 to transition into the balloon valve open state 615-1.

Figure 7A:
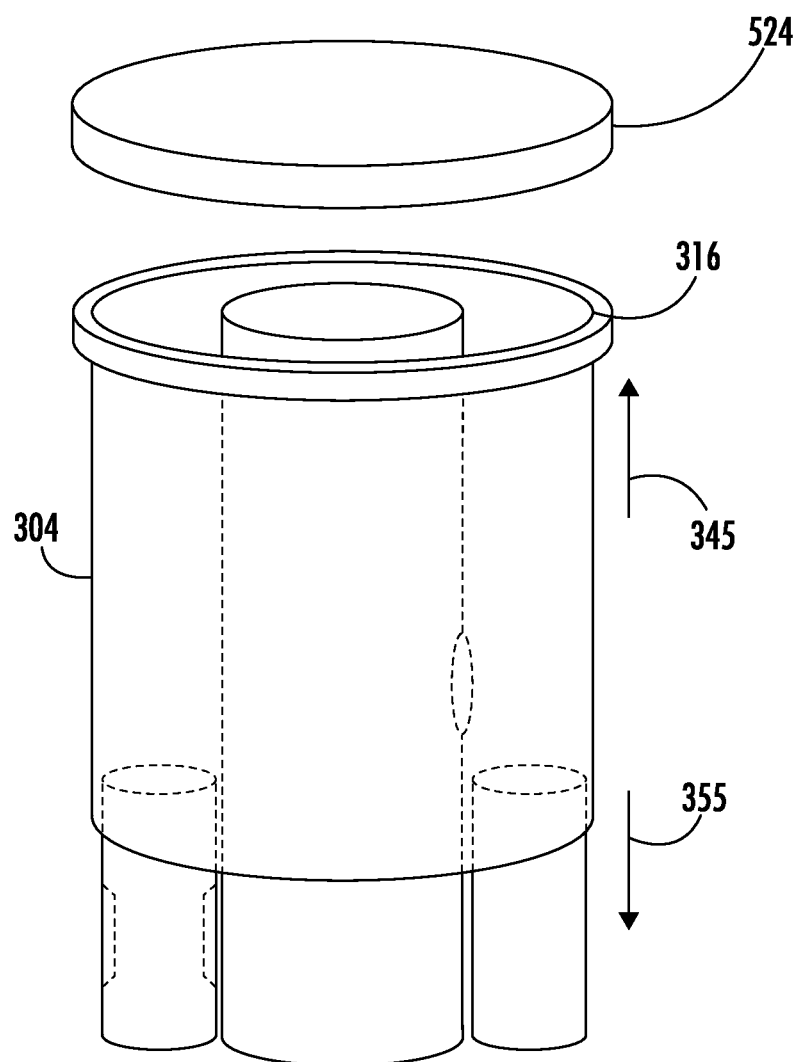
Figure 7B:
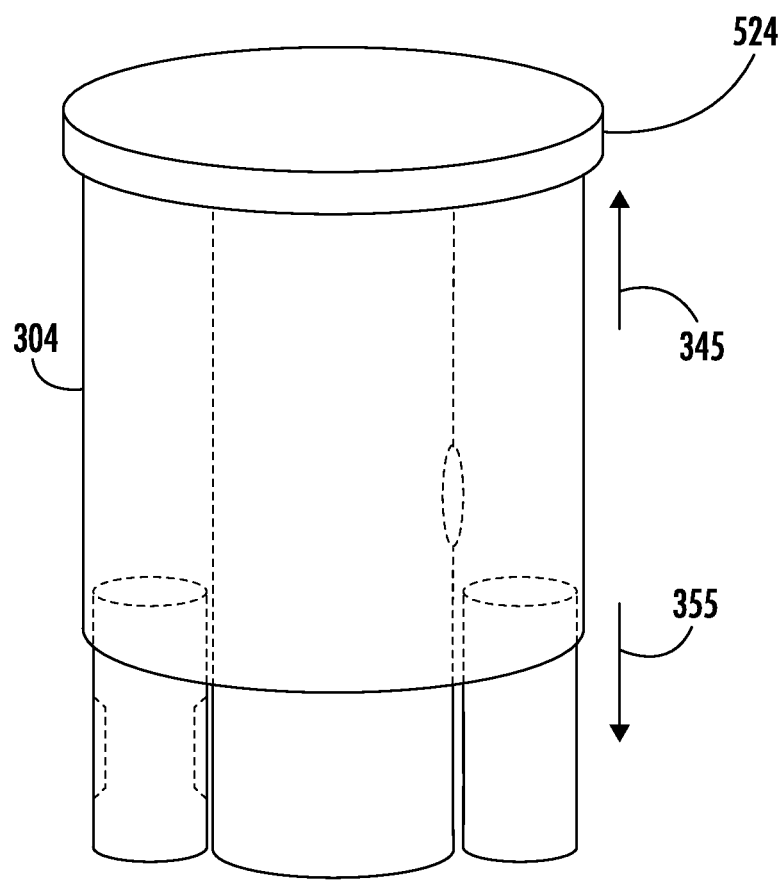

Referring to FIG. 7A, environment 700A illustrates an atmospheric valve open state 715-1. In the atmospheric valve open state 715-1, the atmospheric valve 524 may allow flow through the atmospheric channel 316 of suction valve well 304. Referring to FIG. 7B, environment 700B illustrates an atmospheric valve sealed state 715-2. In the atmospheric valve sealed state 715-2, the atmospheric valve 524 may prevent flow through atmospheric channel 316. As will be discussed in more detail below, in operation, fluid communication with the atmosphere may be provided through a passage/channel in, or created by, one or more components. Further, one or more components may be used to seal portions of the atmospheric channel 316 to facilitate control of fluid communication with the atmosphere by atmospheric valve 524. In some embodiments, atmospheric valve 524 may include a plurality of components configured to control fluid communication with the atmosphere.

Figure 8A:
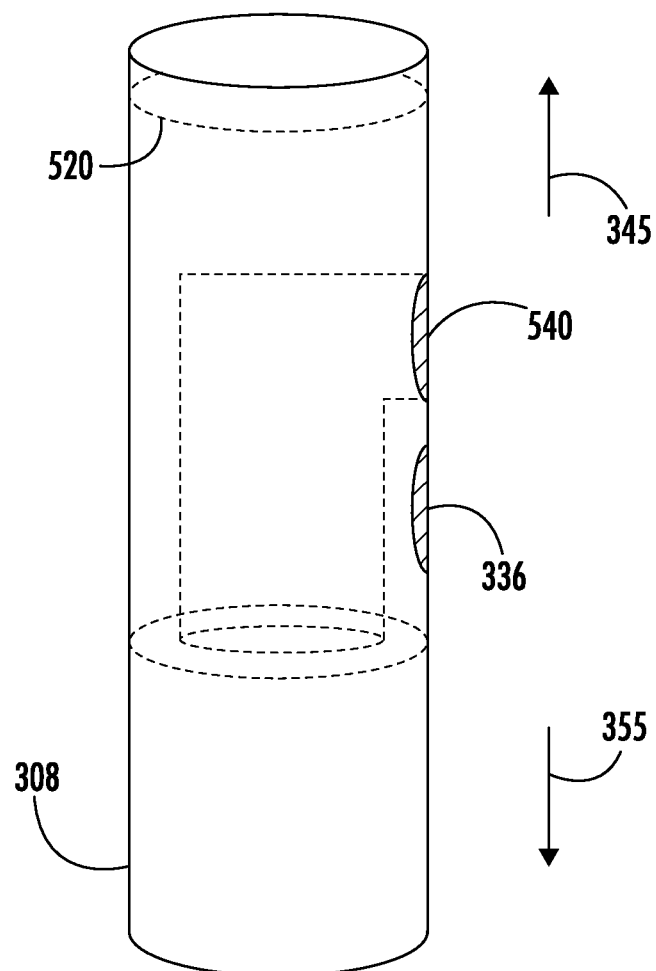
Figure 8B:
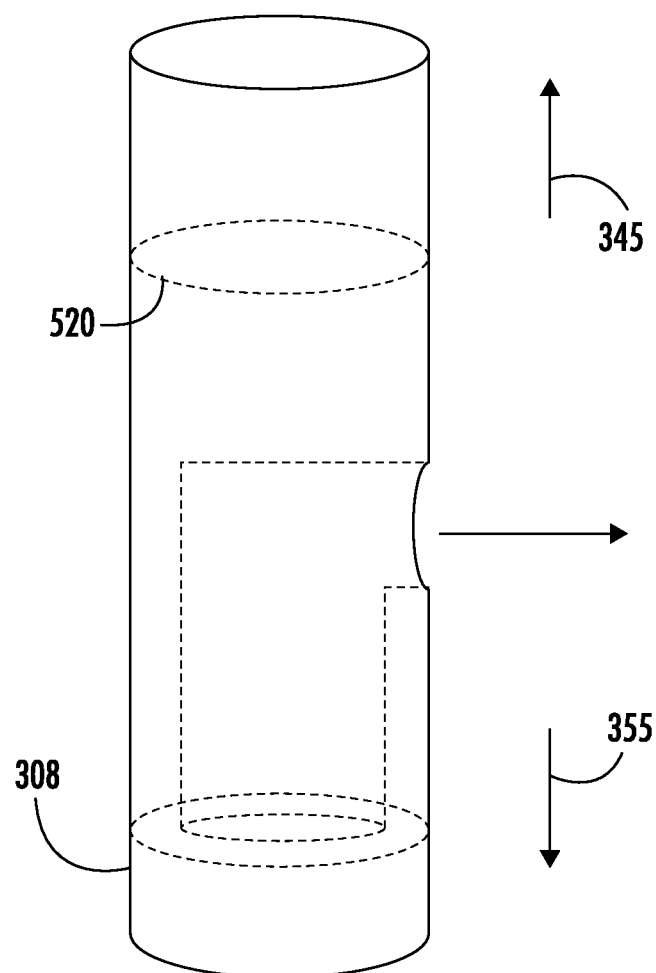
Figure 8C:
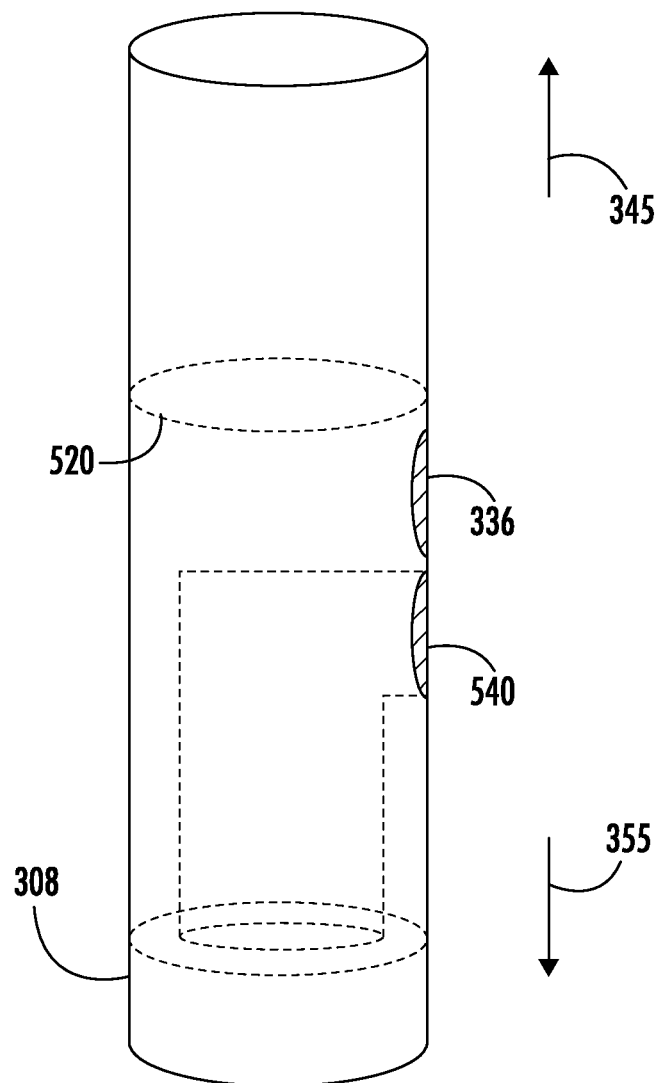

Referring to FIG. 8A, environment 800A illustrates a working channel valve first sealed state 815-1. In the working channel valve first sealed state 815-1, the working channel valve 520 may prevent flow through well radial hole 336 by misaligning the working channel valve radial hole 540 with the well radial hole 336, such as with working channel valve 520 being positioned such that working channel valve radial hole 540 is above well radial hole 336. Referring to FIG. 8B, environment 800B illustrates a working channel valve open state 815-2. In the working channel valve open state 815-2, the working channel valve radial hole 540 and the well radial hole 336 may be aligned to permit suction flow through working channel 308. For example, the flow may enter through the bottom of the working channel valve 520 and exit through the well radial hole 336. Referring to FIG. 8C, environment 800C illustrates a working channel valve second sealed state 815-3. In the working channel valve second sealed state 815-3, the working channel valve 520 may prevent flow through well radial hole 336 by misaligning the working channel valve radial hole 540 with the well radial hole 336, such as with working channel valve 520 being positioned such that working channel radial hole 440 is below well radial hole 336.

Figure 9:
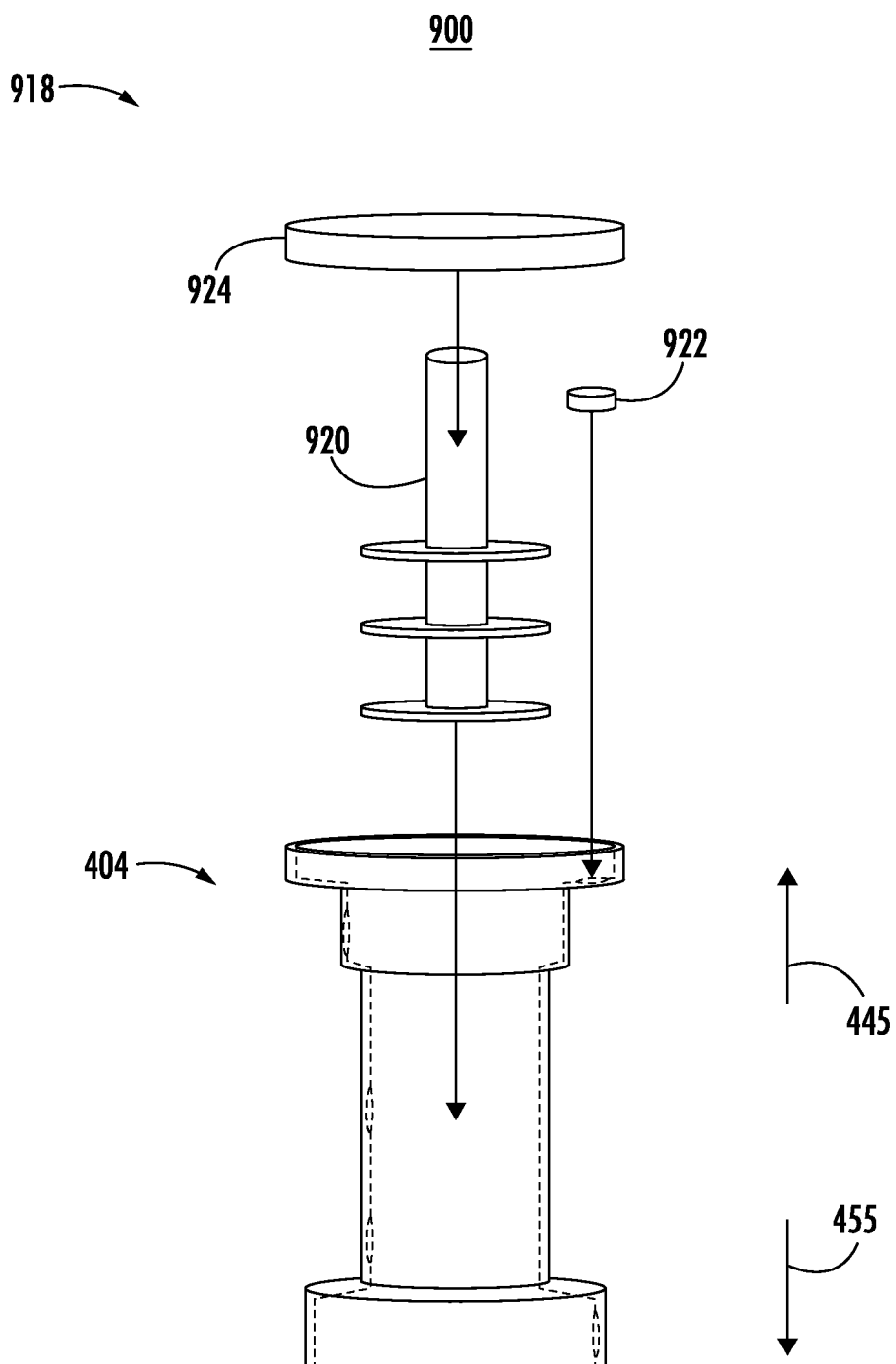
FIG. 9 illustrates an exemplary AW valve set, according to one or more embodiments described herein.

Referring to FIG. 9, environment 900 illustrates AW valve set 918 in conjunction with AW valve well 404. AW valve set 918 may include primary control valve 920, air input valve 922, and atmospheric valve 924. In several embodiments, the primary control valve 920 may be inserted into the AW valve well 404 to control, at least in part, the flow through one or more channels of the AW valve well 404. In various embodiments, the air input valve 922 may be inserted into the air input channel of the AW valve well 404 to control flow therethrough. In many embodiments, the atmospheric valve 924 may be inserted into the atmospheric channel of AW valve well 404 to control flow therethrough. In many embodiments, one or more valves in AW valve set 918 may be integrated with one or more portions of a housing and/or valve interface mechanism corresponding to AW valve well 404.

In one or more embodiments, the atmospheric valve 924 may be configured to control fluid communication with the atmosphere from the interior of the AW valve well 404. In many embodiments, the atmospheric valve 924 may include a hole in a housing. In some embodiments, the atmospheric valve 924 may be operated by covering and/or uncovering the hole, such as with a finger or other mechanism. In several embodiments, the positioning and/or configuration of the valves in AW valve set 918 may be controlled by one or more components of a corresponding valve interface mechanism. In some embodiments, one or more portions of the atmospheric channel 416 may be included in the primary control valve 920. In some such embodiments, the atmospheric channel 416 may comprise one or more passages through at least a portion of the primary control valve 920. For example, the atmospheric channel 416 may comprise a hole in the top of the primary control valve 920 in fluid communication with a radial hole in the primary control valve 920 proximate the air input channel 406. In such examples, covering the hole may direct air flow into the air output channel 410 and down a working channel of an endoscope.

Figure 10A:
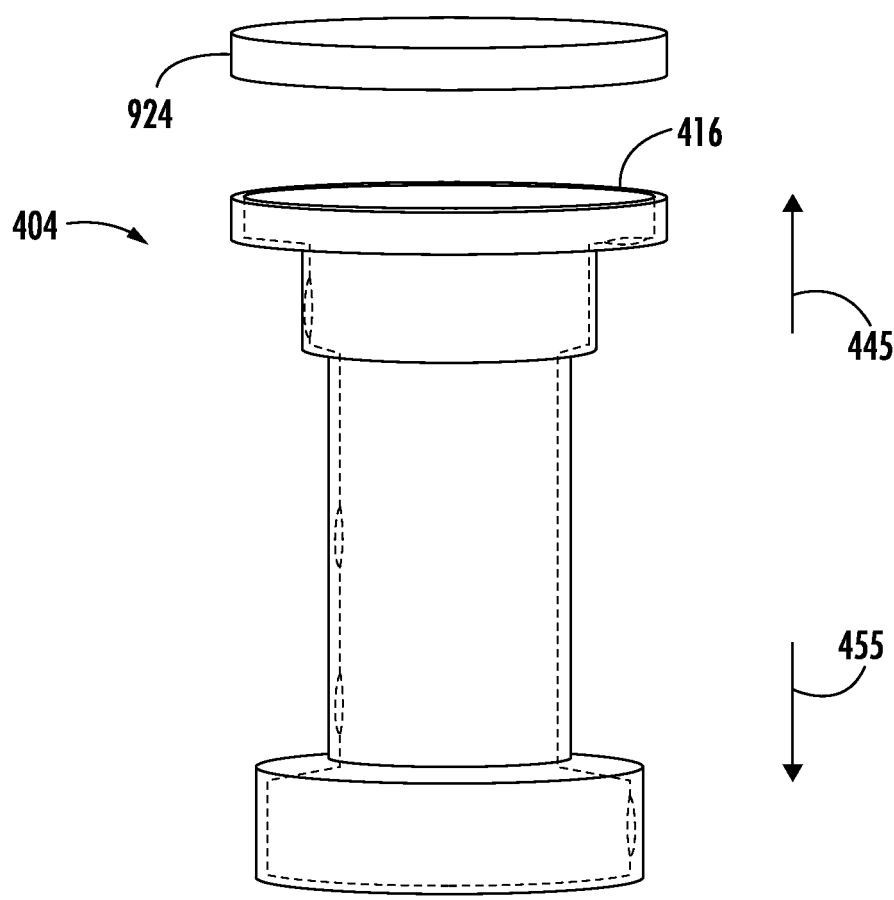
FIGS. 10A-12C illustrate various aspects of exemplary valves in AW valve sets, according to one or more embodiments described herein.
Figure 10B:
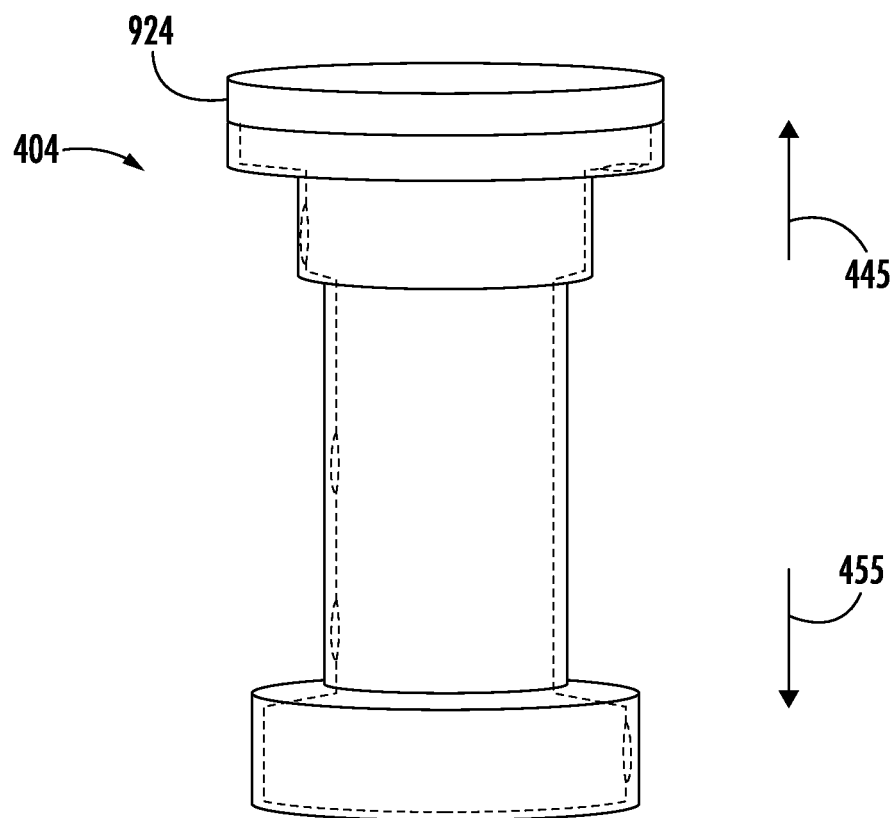

Referring to FIG. 10A, environment 1000A illustrates an atmospheric valve open state. In the atmospheric valve open state, the atmospheric valve 924 may allow flow through the atmospheric channel of AW valve well 404. Referring to FIG. 10B, environment 1000B illustrates an atmospheric valve sealed state 1015-2. In the atmospheric valve sealed state 1015-2, the atmospheric valve 924 may prevent flow through atmospheric channel of AW valve well 404. As will be discussed in more detail below, in operation, fluid communication with the atmosphere may be provided through a passage/channel in, or created by, one or more components (e.g., primary control valve 920). Further, one or more components may be used to seal portions of the atmospheric channel 316 to facilitate control of fluid communication with the atmosphere by atmospheric valve 924. In some embodiments, atmospheric valve 924 may include a plurality of components configured to control fluid communication with the atmosphere.

Figure 11A:
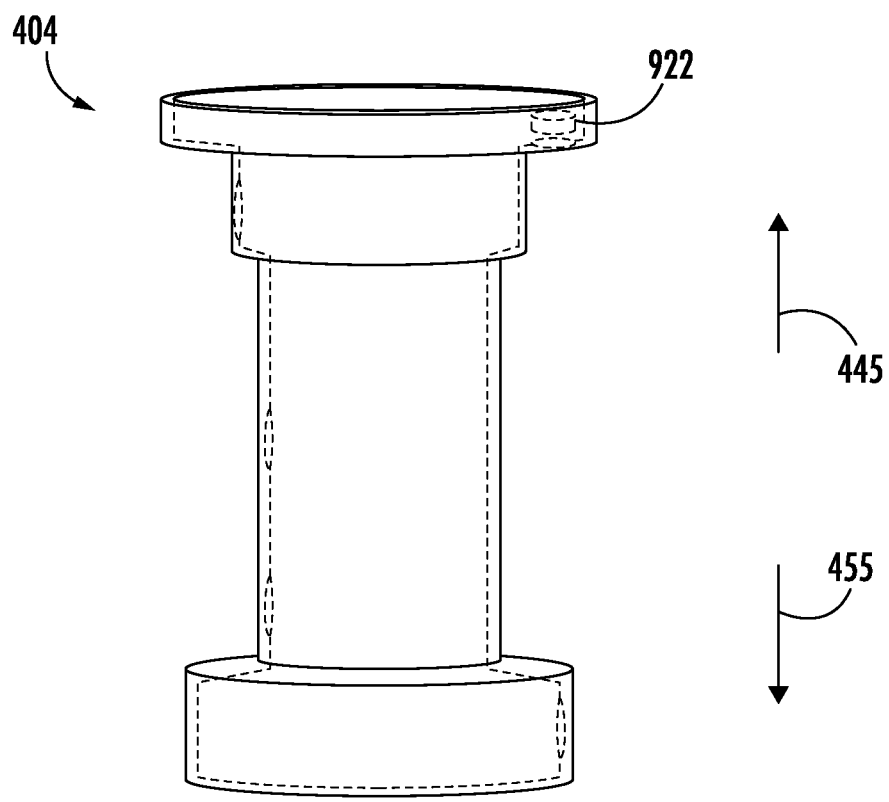
Figure 11B:
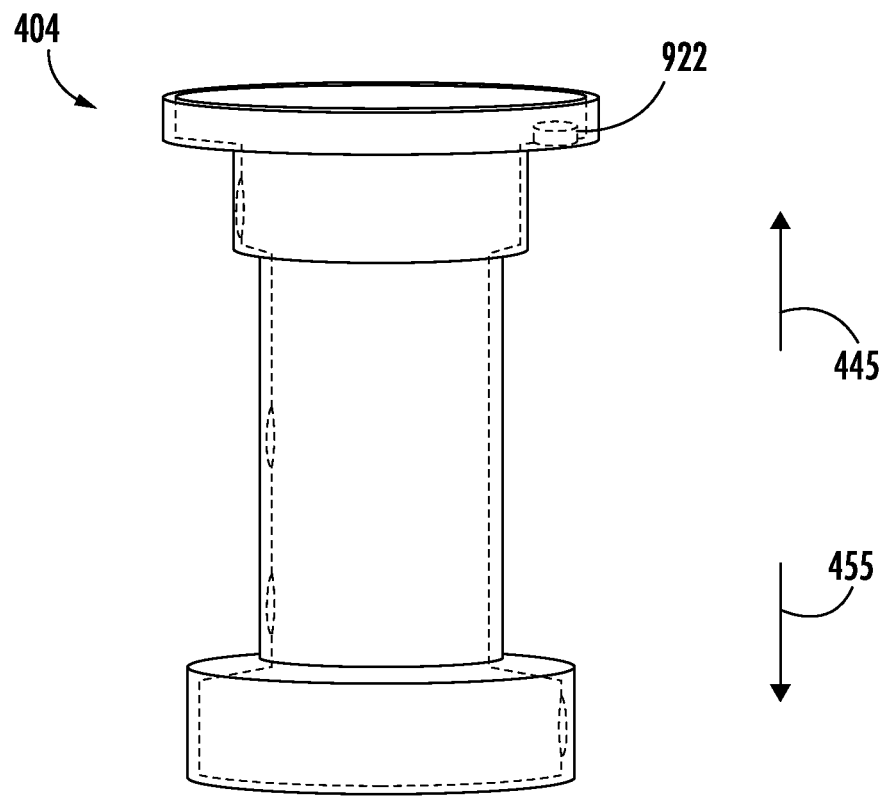

Referring to FIG. 11A, environment 1100A illustrates an air input valve open state 1115-1. In the air input valve open state 1115-1, the air input valve 522 may allow flow through the air input channel of AW valve well 404. Referring to FIG. 11B, environment 1100B illustrates an air input valve sealed state 1115-2. In the air input valve sealed state 1115-2, the air input valve 922 may prevent flow through the air input channel of AW valve well 404. In some embodiments, sealing the air input channel may cause a fluid source (e.g., water reservoir) to be pressurized, thereby enabling/causing fluid to flow into the AW valve well 404 via water input channel 408.

Figure 12A:
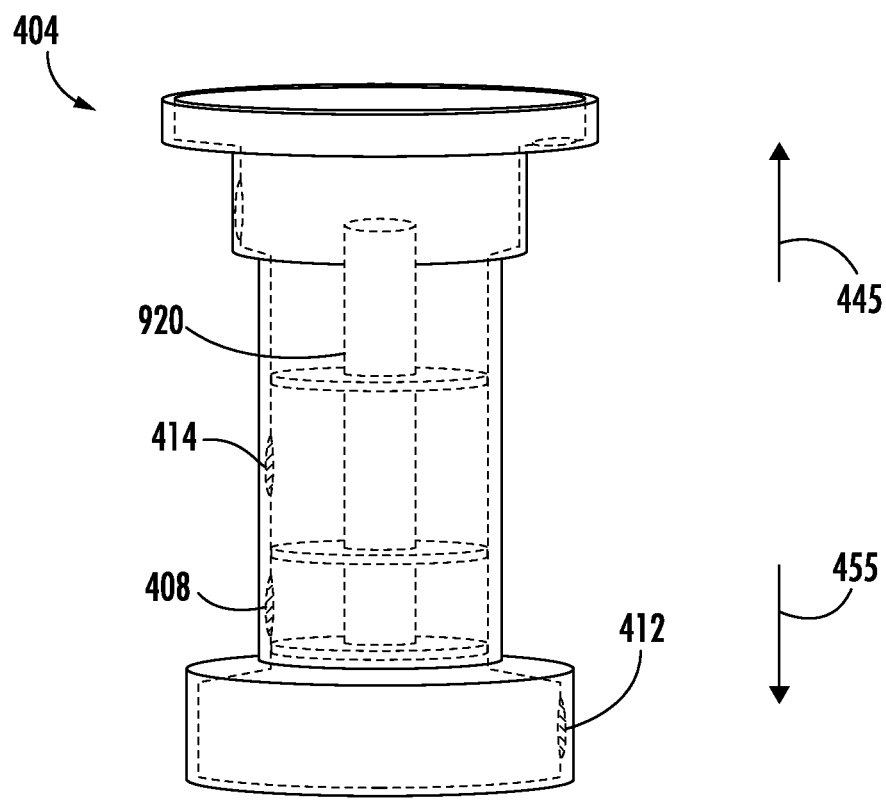
Figure 12B:
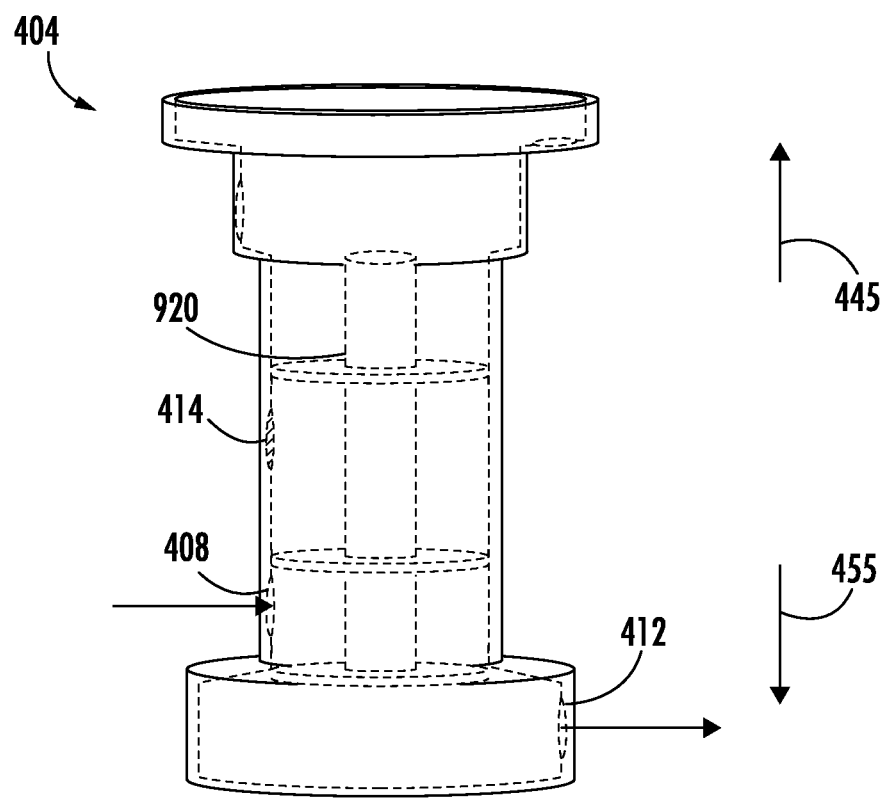
Figure 12C:
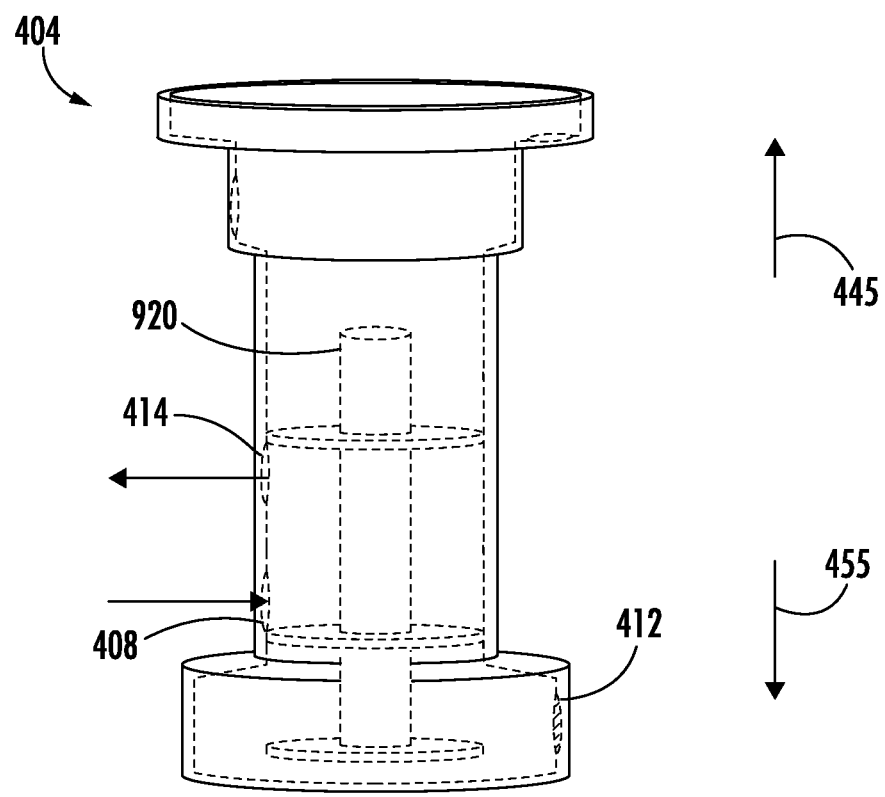

Referring to FIG. 12A, environment 1200A illustrates a primary valve sealed state 1215-1. In the primary valve sealed state 1215-1, the primary control valve 920 may prevent flow through one or more of the balloon channel 414, water input channel 408, and water output channel 412. Referring to FIG. 12B, environment 1200B illustrates a primary valve water output state 1215-2. In the primary valve water output state 1215-2, the primary control valve 920 may be positioned to block flow through balloon channel 414 and permit flow from water input channel 408 to water output channel 412. In various embodiments, primary control valve 920 may utilize changes in diameter in AW valve well 404 to control flow. Referring to FIG. 12C, environment 1200C illustrates a primary valve balloon fill state 1215-3. In the primary valve balloon fill state 1215-3, the primary control valve 920 may be positioned to block flow through water output channel 412 and permit flow from water input channel 408 to balloon channel 414. In various embodiments, one or more features of primary control valve 920 may operate as valves for multiple channels. In some embodiments, one or more features of primary control valve 920 may comprise one or more channels, or one or more portions thereof. For example, primary control valve 920 may comprise atmospheric channel 416.

Figure 13:
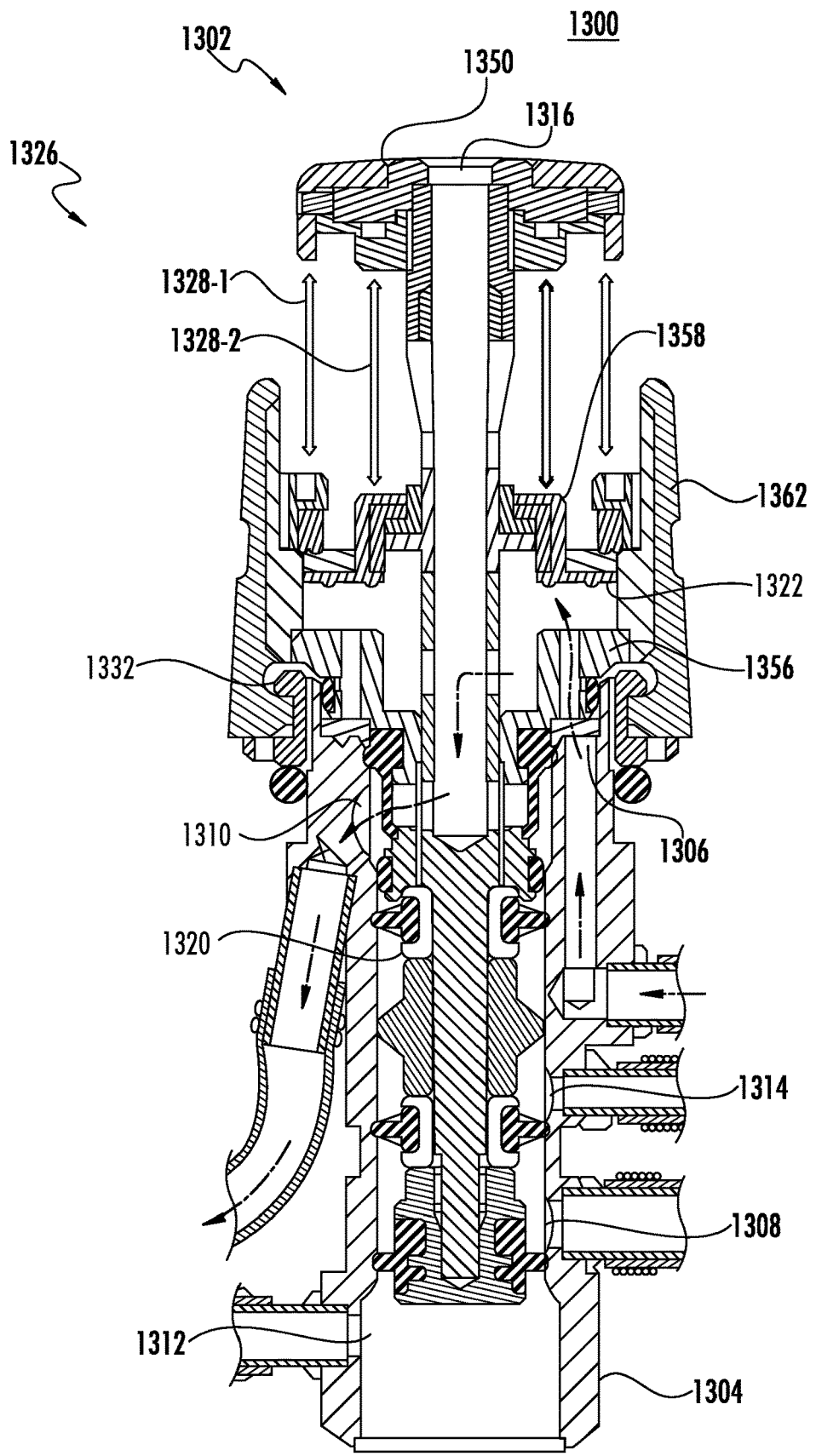
FIG. 13 illustrates various aspects of an exemplary AW valve assembly, according to one or more embodiments described herein.

FIG. 13 illustrates various aspects of an exemplary AW valve assembly 1302 in environment 1300, according to one or more embodiments described herein. In many embodiments, a cross section of one or more portions of AW valve assembly 1302 may be illustrated in environment 1300. In some embodiments, one or more components of FIG. 13 may be the same or similar to one or more other components described herein. AW valve assembly 1302 includes an AW valve well 1304, an AW valve set, and a valve interface mechanism 1326. The illustrated portion of the AW valve well 1304 includes air input channel 1306, water input channel 1308, air output channel 1310, water output channel 1312, balloon channel 1314, and lip 1332. The illustrated portion of the AW valve set may include primary control valve 1320 and an air input valve 1322 comprised in the valve interface mechanism, such as hat 1358 or interface member 1350. Additionally, or alternatively, the valve interface mechanism may include biasing members 1328-1, 1328-2, hat 1358, housing 1362, interface member 1350, linkage 1356, and atmospheric channel 1314. In one or more embodiments, the biasing members 1328 may be disposed between the hat 1358 and the interface member 1350. In various embodiments, the biasing members 1328-1, 1328-2 may be concentrically disposed. Embodiments are not limited in this context.

In several embodiments, biasing members 1328 may be configured to provide tactile feedback via the interface member 1350 to provide indications of the state of the AW valve assembly 1302. In many embodiments, biasing members 1328-1, 1328-2 may be configured to bias the AW valve assembly into a first state (e.g., an atmospheric escape state). In the illustrated embodiment, AW valve assembly 1302 may be in a second state (e.g., an air delivery state). Accordingly, as shown by the illustrated arrows, a flow may enter the AW valve assembly 1302 via air input channel 1306 and exit via air output channel 1310. In one or more embodiments, disposing the biasing member 1328 and/or one or more portions of the housing, linkages, and valves above the hat 1358 may simplify manufacturing or assembly. Further, such disposition may enable more compact components, such as a shorter hat 1358.

In various embodiments, for the third state (e.g., water delivery state), the interface member 1350 may be depressed down toward the hat 1358. In many embodiments, the interface member 1350 is depressed to a first stop in the water delivery state to provide tactile feedback. For the fourth state (e.g., balloon fill state), the interface member 1350 may depress the interface member 1350 and the hat 1358 toward the bottom of valve well 1304. In several embodiments, the interface member 1350 is depressed to a second stop in the balloon fill state to provide tactile feedback. For example, hat 1358 may come to a hard stop against linkage 1356 at the second stop.

In some embodiments, biasing member 1328-1 may provide a first resistance and biasing member 1328-2 may provide a second resistance. In one or more embodiments, biasing member 1328-2 may compress to place water input channel 1308 in fluid communication with water output channel 1312. In one or more such embodiments, the second resistance may be less than the first resistance. In various embodiments, biasing member 1328-1 and biasing member 1328-2 may compress to place water input channel 1308 in fluid communication with balloon channel 1314. In some embodiments, the biasing members 1328 may position the AW valve assembly in the atmospheric escape state in the absence of user input. In several embodiments, biasing members 1328 may bias one or more components, such as primary control valve 1320, and interface member 1350 toward the top of the AW valve assembly 1302.

FIGS. 14A-14D illustrate various aspects of an exemplary AW valve assembly 1402 in environments 1400A-1400D, according to one or more embodiments described herein. In many embodiments, a cross section of one or more components may be illustrated in environments 1400A-1400D. In some embodiments, one or more components of FIGS. 14A-14D may be the same or similar to one or more other components described herein. For instance, AW valve assembly 1402 may be the same or similar to AW valve assembly 1302. Environments 1400A-1400D may include one or more portions of the AW valve assembly 1402. In one or more embodiments described herein, AW valve assembly 1402 may include a dual spring configuration to provide reliable, intuitive, and ergonomic control of fluid through the AW valve well 1404. Embodiments are not limited in this context.

Figure 14A:
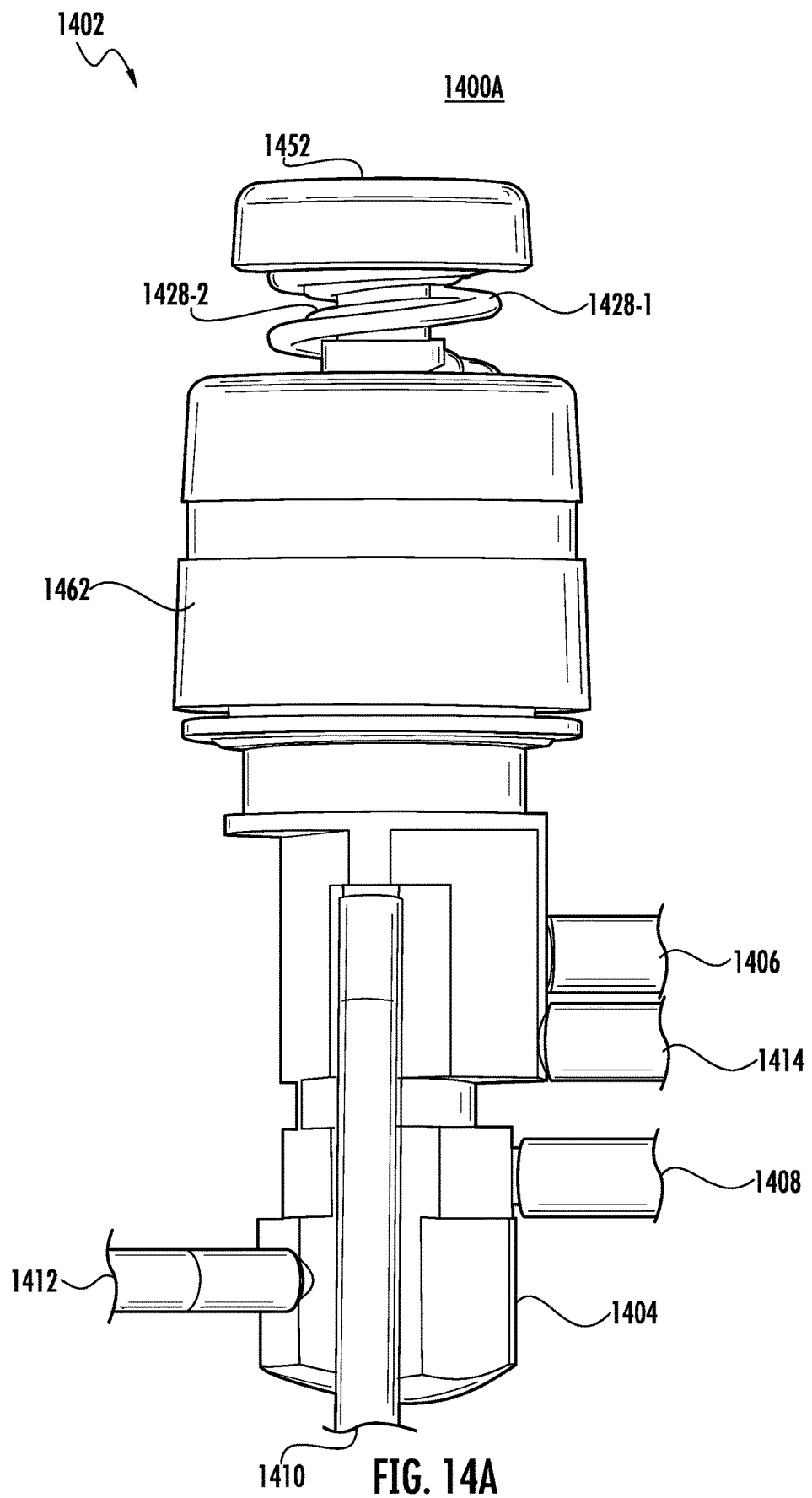
FIGS. 14A-14D illustrate various aspects of an exemplary AW valve assembly, according to one or more embodiments described herein.
Figure 14B:
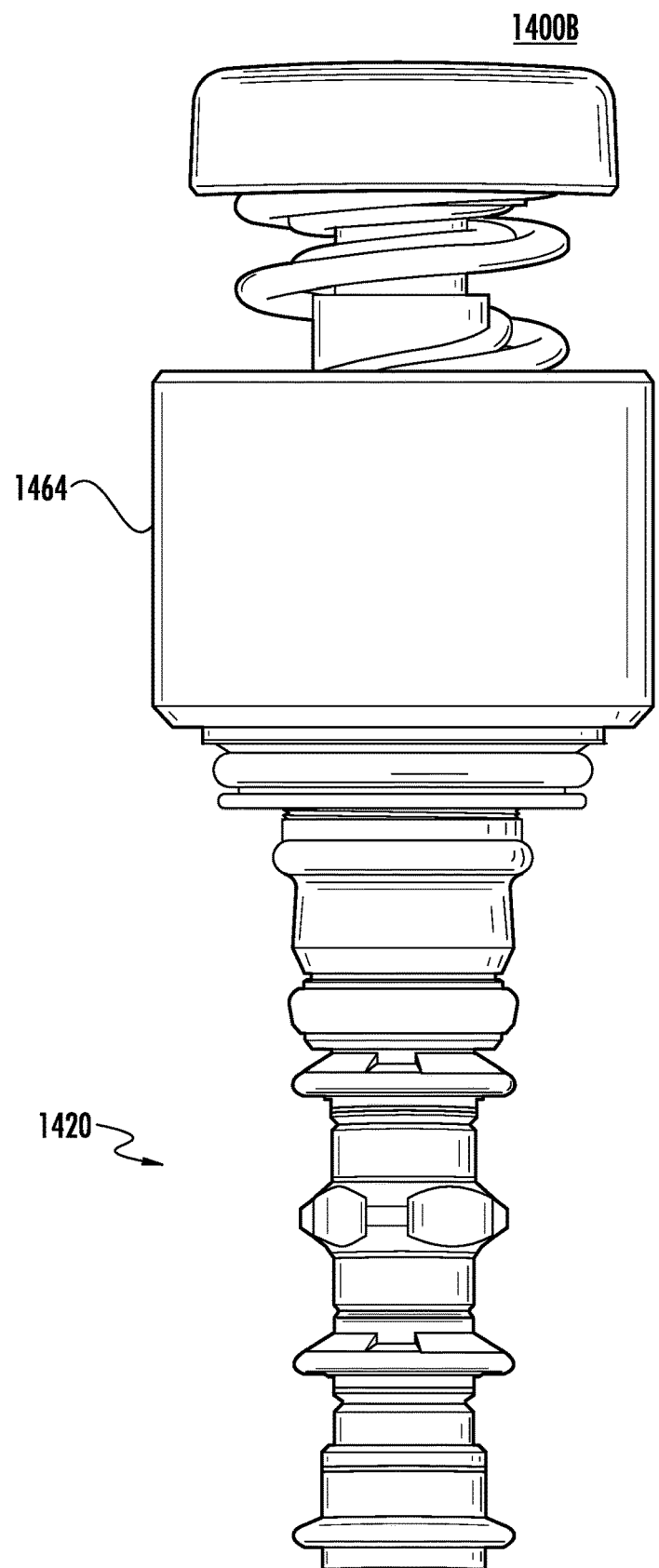

Referring to FIG. 14A, environment 1400A illustrates a perspective view of AW valve assembly 1402. In the illustrated embodiment, AW valve assembly 1402 may include an interface 1452, biasing members 1428-1, 1428-2, housing 1462, and AW valve well 1404 with air input channel 1406, water input channel 1408, air output channel 1410, water output channel 1412 and balloon channel 1414. Referring to FIG. 14B, environment 1400B illustrates an assembly stage of the AW valve assembly 1402. The illustrated embodiment may include bowl 1464 and primary control valve 1420 with a set of seals disposed along the length.

Figure 14C:
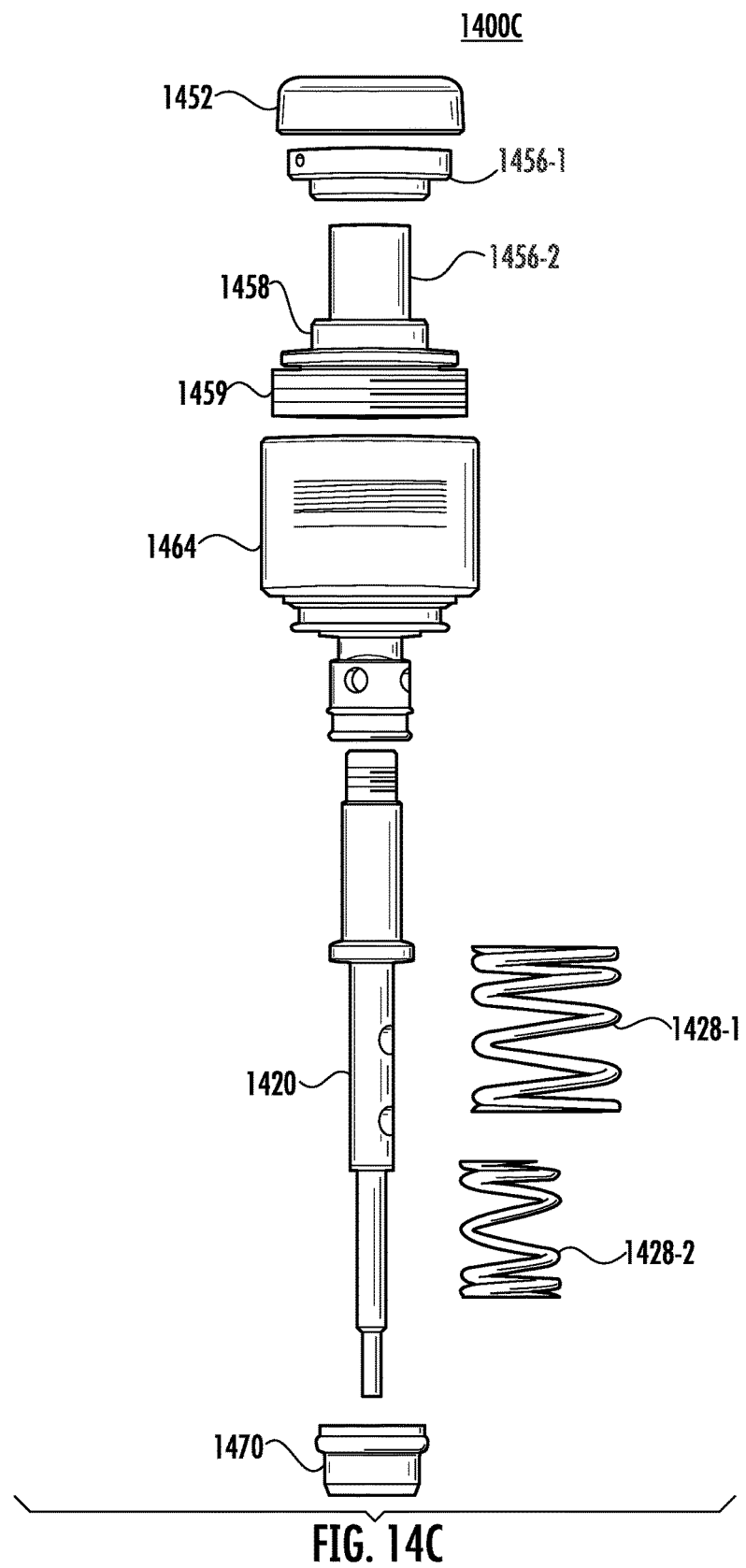

Referring to FIG. 14C, environment 1400C illustrates an exploded view of various components of AW valve assembly 1402. The illustrated embodiment may include interface 1452, hat 1458, threads 1459, bowl 1464, primary control valve 1420, biasing members 1428-1, 1428-2, linkages 1456-1, 1456-2, and bowl gasket 1470. In some embodiments, one or more of linkages 1456-1, 1456-2 may be included in and/or coupled to other components of AW valve assembly 1402. For example, linkage 1456-1 may be included in interface 1452 and/or an atmospheric valve. In another example, linkage 1456-2 may include, or at least couple with, a portion of primary control valve 1420.

Figure 14D:
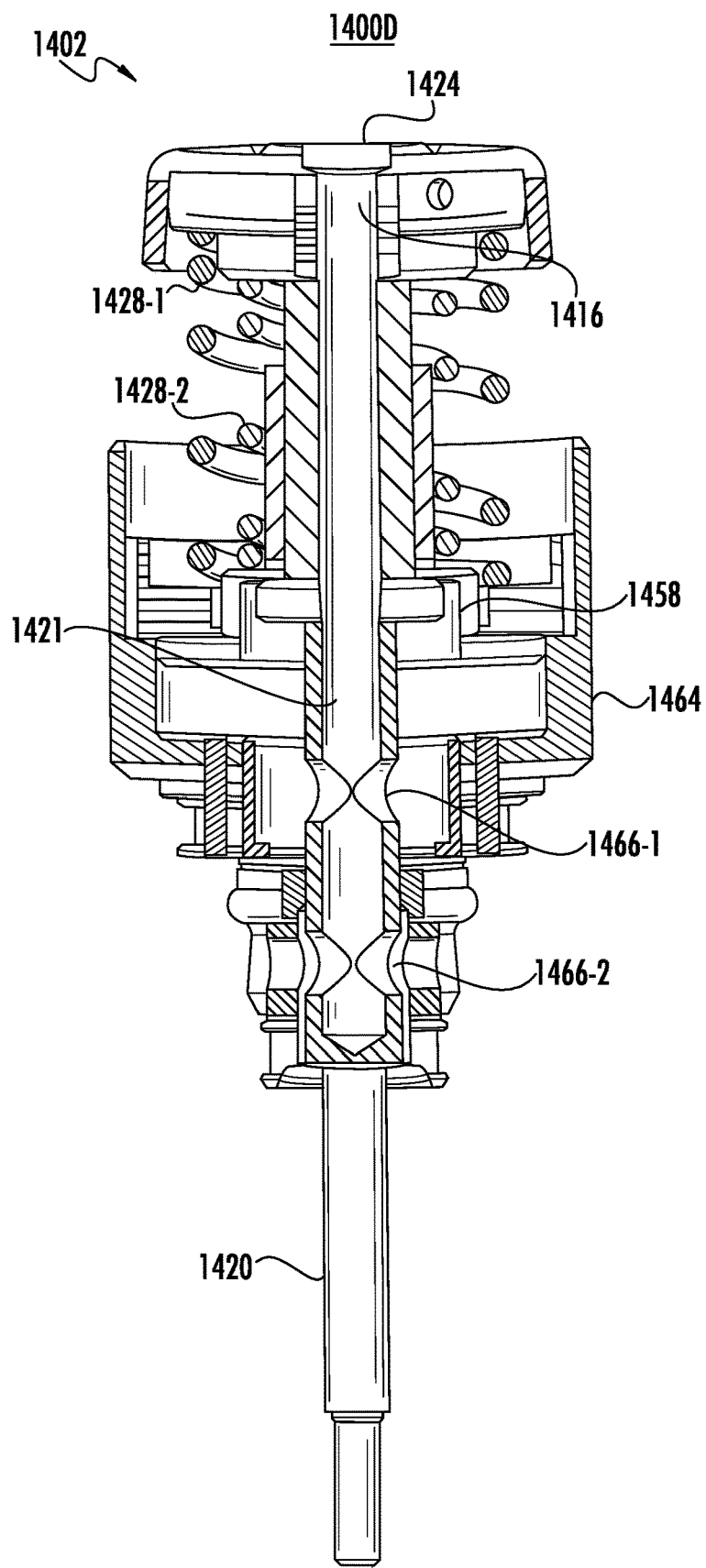

Referring to FIG. 14D, environment 1400D illustrates a cross-sectional view of AW valve assembly 1402. In the illustrated embodiment, AW valve assembly 1402 may include atmospheric valve 1424, biasing members 1428, atmospheric channel 1416, hat 1458, bowl 1464, and primary control valve 1420 with internal channel 1421, radial air holes 1466-1, 1466-2, and at least a portion of atmospheric channel 1416.

Figure 15A:
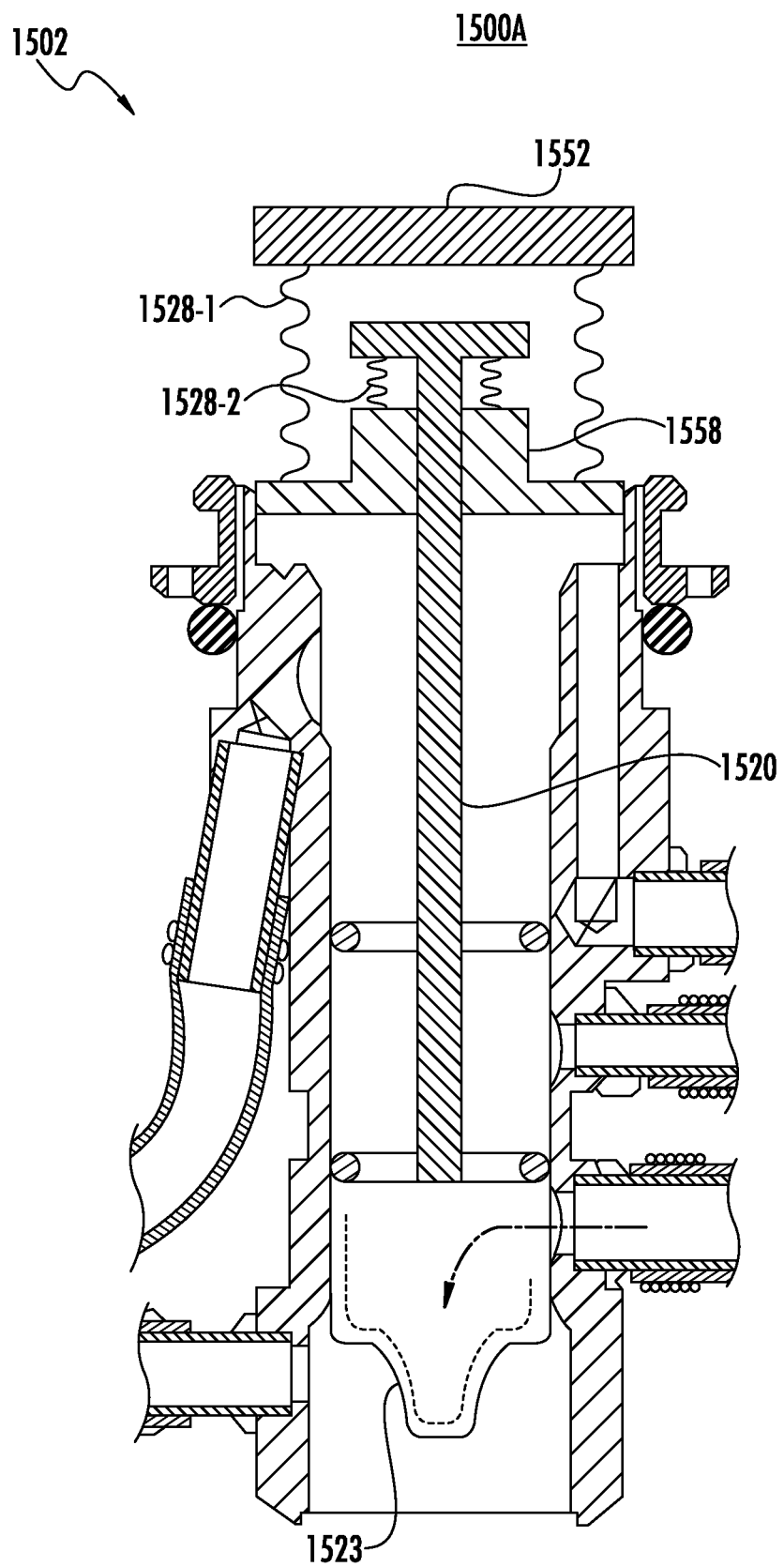
FIGS. 15A-15C illustrate various aspects of an exemplary AW valve assembly, according to one or more embodiments described herein.
Figure 15B:
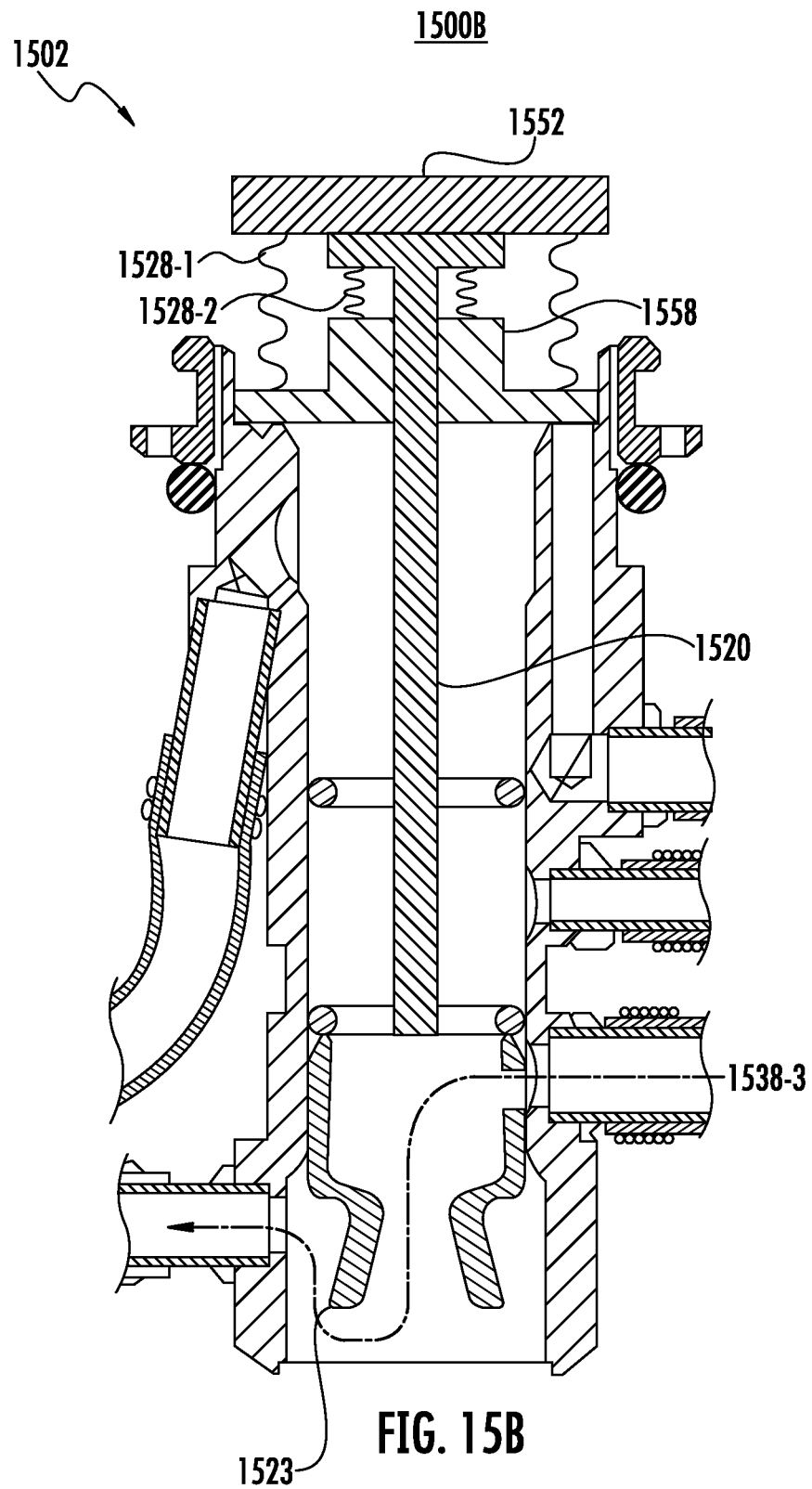
Figure 15C:
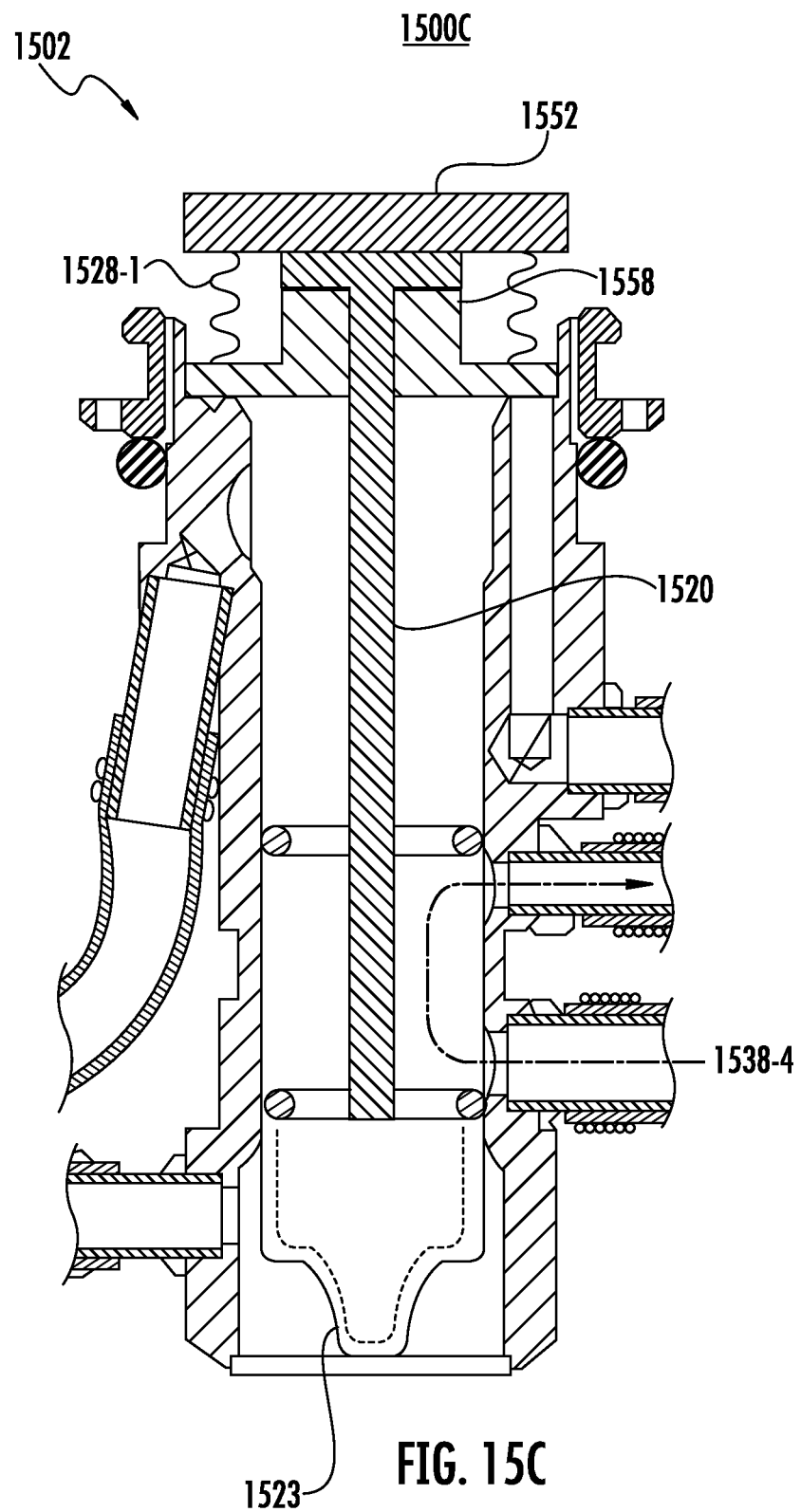

FIGS. 15A-15C illustrate various aspects of an exemplary AW valve assembly 1502 in environments 1500A, 1500B, 1500C according to one or more embodiments described herein. In many embodiments, a cross section of one or more components may be illustrated in environments 1500A, 1500B, 1500C. In some embodiments, one or more components of FIGS. 15A-15C may be the same or similar to one or more other components described herein. Environments 1500A, 1500B, 1500C may include an AW valve assembly 1502. The illustrated embodiment of AW valve assembly 1502 includes interface 1552, biasing members 1528-1, 1528-2, hat 1558, and primary control valve with duckbill valve 1523. Environment 1500A may include the AW valve assembly 1502 in an air delivery state, environment 1500B may include the AW valve assembly 1502 in a water delivery state, and environment 1500C may include the AW valve assembly 1502 in a balloon fill state. Embodiments are not limited in this context.

In some embodiments, the duckbill valve 1523 may provide the primary means of stopping water from entering the water output channel. Accordingly, duckbill valve 1523 may only allow water to pass to the water output channel when pressure from the water input channel is sufficient. In various embodiments, the hat 1558 may include the air input valve. As shown in FIGS. 15B and 15C, the hat 1558 may displace downward, due to input, to cover and seal the air input valve. In one or more embodiments, biasing member 1528-2 may bias the primary control valve 1520 toward the top of the AW valve assembly 1502 when in the water delivery state. However, in the absence of input, air pressure from the air input channel may bias the hat 1558 and/or the primary control valve 1520 toward the top of the AW valve assembly 1502. In other embodiments, a spring may bias the hat 1558 and/or the primary control valve 1520 toward the top of the AW valve assembly 1502 in the absence of input. In many embodiments, biasing member 1528-2 may resist compression to a greater degree than biasing member 1528-1. In the balloon fill state, the biasing members 1528-1, 1528-2 may be fully compressed such that interface 1552 reaches a hard stop from further downward displacement.

Figure 16A:
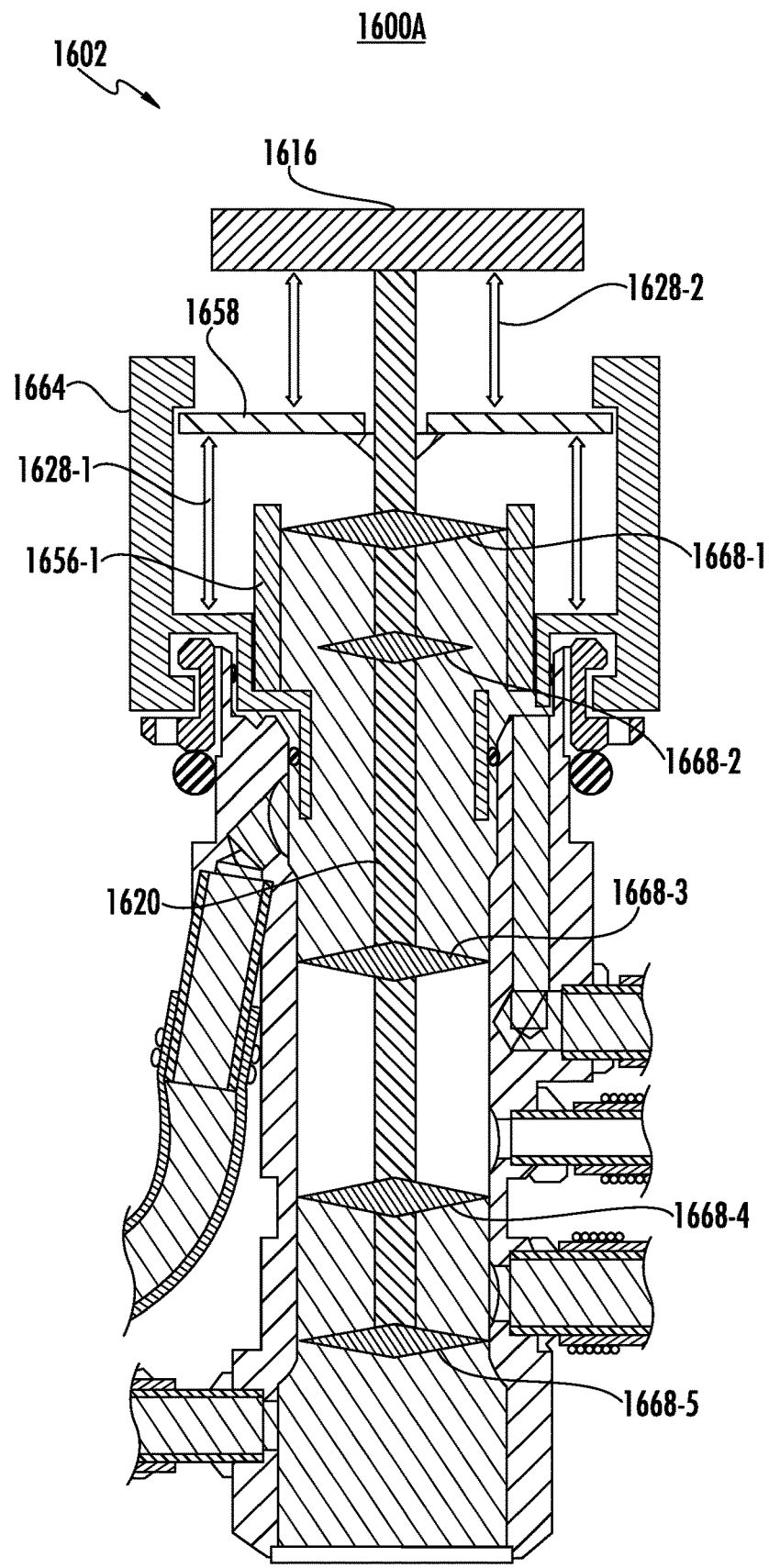
FIGS. 16A-16C illustrate various aspects of an exemplary AW valve assembly, according to one or more embodiments described herein.
Figure 16B:
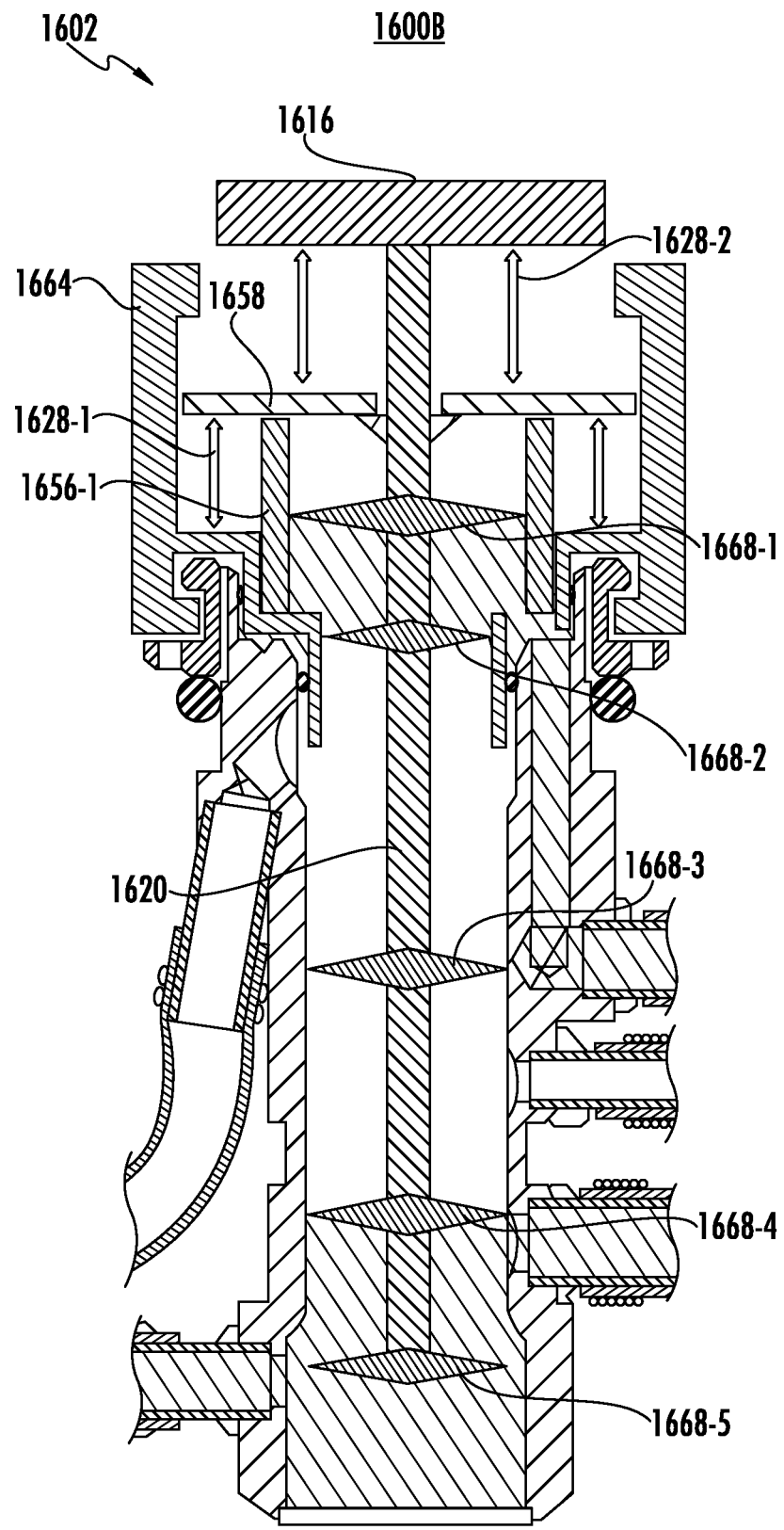
Figure 16C:
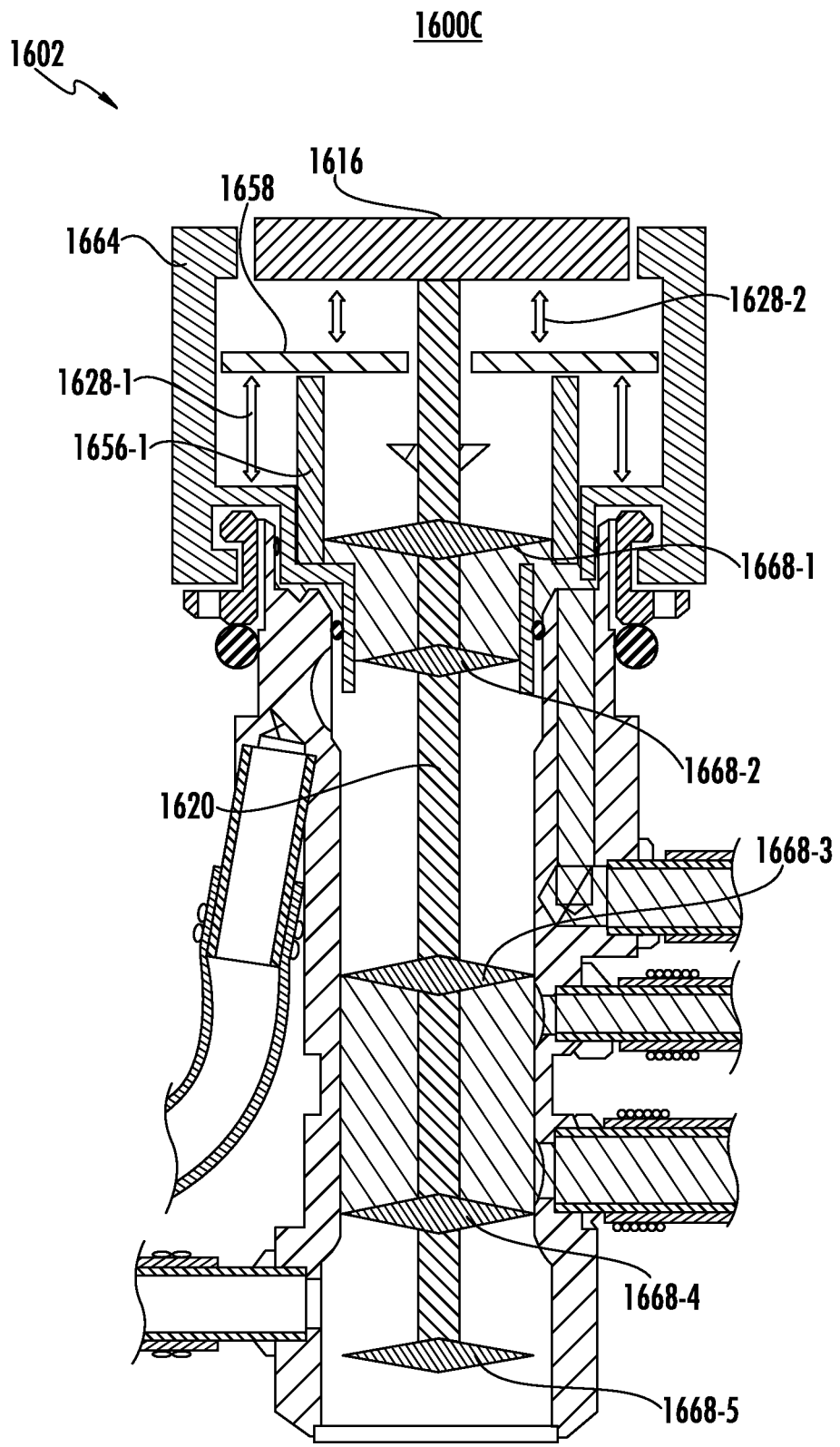

FIGS. 16A-16C illustrate various aspects of an exemplary AW valve assembly 1602 in environments 1600A, 1600B, 1600C according to one or more embodiments described herein. In many embodiments, a cross section of one or more components may be illustrated in environments 1600A, 1600B, 1600C. In some embodiments, one or more components of FIGS. 16A-16C may be the same or similar to one or more other components described herein. Environments 1600A, 1600B, 1600C may include an AW valve assembly 1602. The illustrated embodiment of AW valve assembly 1602 includes atmospheric channel 1616, biasing members 1628-1, 1628-2, linkage 1656-1, and primary control valve 1620 with a top, a bottom, and seals 1668-1, 1668-2, 1668-3, 1668-4, 1668-5 disposed along a length therebetween. In one or more embodiments, the primary control valve 1620 may be vertically displaced to control flow through the valve well. Embodiments are not limited in this context.

In various embodiments, seals 1668-1, 1668-2 may create separate seals with the valve interface mechanism. In many embodiments, seals 1668-3, 1668-4, 1668-5 may create separate seals with the valve well. In several embodiments, one or more of the seals may have different diameters. In one embodiment, a first side of seal 1668-3 may be utilized to control the flow of air through the valve well while a second side of seal 1668-3 may be utilized to control the flow of water through the valve well. In many embodiments, positioning seal 1668-1 above the linkage 1656-1 may place atmospheric channel 1616 in fluid communication with the air input channel Referring to FIG. 16A, environment 1600A illustrates the primary control valve 1620 configured to place the air input channel in fluid communication with the air output channel. In various embodiments, seal 1668-1 may create a seal with linkage 1656-1 and seal 1668-3 may create a seal with the valve well to place the air input and output channels in fluid communication. In various such embodiments, flow through the balloon channel may be confined between seals 1668-3, 1668-4, flow through the water input channel may be confined between seals 1668-4, 1668-5, and flow through the water output channel may be confined by seal 1668-5. In many embodiments, the AW valve assembly 1602 may be in an air delivery state in environment 1600A. For example, atmospheric channel 1616 may be sealed with a finger and/or an atmospheric valve. However, unsealing atmospheric channel 1616, such as by removing the finger, may transition the AW valve assembly 1602 into an air escape state.

Referring to FIG. 16B, environment 1600B illustrates the primary control valve 1620 configured to place the water input channel in fluid communication with the water output channel and block flow from the air input channel. In various embodiments, AW valve assembly 1602 may be in a water delivery state in environment 1600B. In some embodiments, seal 1668-4 may create a seal with the valve well between the balloon input channel and the water input channel and/or seal 1668-5 may be displaced into a portion of the valve well with a wider diameter to place the water input and output channel in fluid communication. In various embodiments, seals 1668-1, 1668-2 may create seals with linkage 1656-1 to block flow from the air input channel. As shown in the illustrated embodiments, seals 1668-1, 1668-2 may have different diameters to seal with different diameters of the linkage 1656-1. In many embodiments, tactile feedback may be generated in response to the hat 1658 contacting linkage 1656-1 to indicate the AW valve assembly is in the water deliver state.

Referring to FIG. 16C, environment 1600C illustrates the primary control valve 1620 configured to place the water input channel in fluid communication with the balloon channel and block flow from the air input channel. In various embodiments, AW valve assembly 1602 may be in a balloon fill state in environment 1600C. In some embodiments, seals 1668-3, 1668-4 may direct flow from water input channel into balloon fill channel and/or seal 1668-5 may be displaced into a portion of the valve well with a wider diameter to place the water input and output channel in fluid communication. In various embodiments, seals 1668-1, 1668-2 may create seals with linkage 1656-1 to block flow from the air input channel. As shown in the illustrated embodiments, seals 1668-1, 1668-2 may have different diameters to seal with different diameters of the linkage 1656-1.

FIGS. 17A-17D illustrate various aspects of an exemplary AW valve assembly 1702 in environments 1700A-1700D, according to one or more embodiments described herein. In many embodiments, a cross section of one or more components may be illustrated in environments 1700A-1700D. In some embodiments, one or more components of FIGS. 17A-17D may be the same or similar to one or more other components described herein. For instance, AW valve assembly 1702 may be the same or similar to AW valve assembly 1602. Environments 1700A-1700D may include one or more portions of the AW valve assembly 1702. In one or more embodiments described herein, AW valve assembly 1702 may include a set of components to control fluid flow (e.g., air and/or water flow) through the AW valve well. In one or more such embodiments, utilization of the set of components may provide reliable, intuitive, and ergonomic control of fluid through the AW valve well 1704. In some embodiments, the set of components may include a set of seals comprised in, or disposed along, the primary control valve to control fluid flow through the AW valve well 1704. Additionally, or alternatively, utilization of seals to control fluid flow through the AW valve well 1704 may simplify manufacturing and/or assembly. Embodiments are not limited in this context.

Figure 17A:
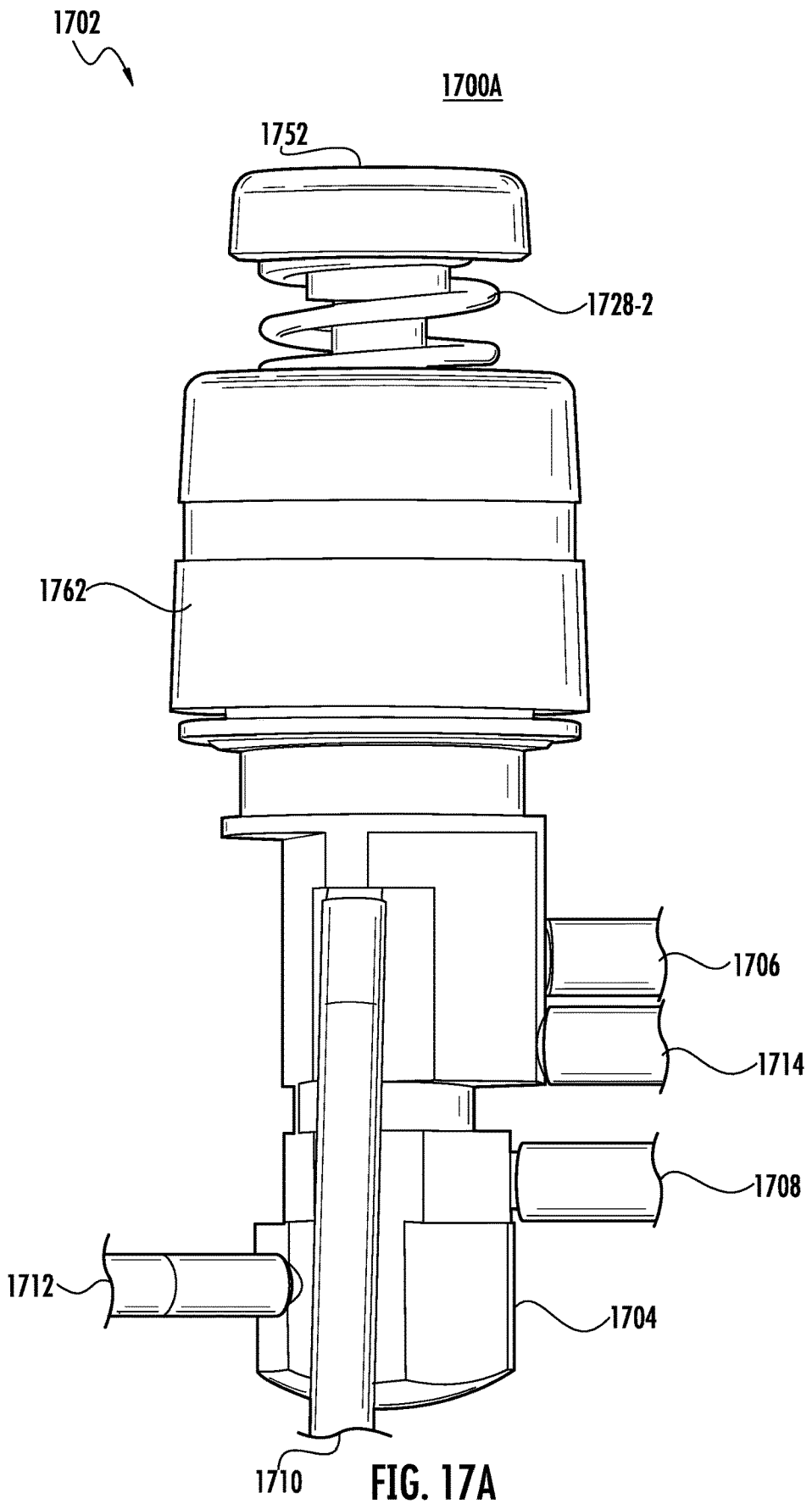
FIGS. 17A-17D illustrate various aspects of an exemplary AW valve assembly, according to one or more embodiments described herein.
Figure 17B:
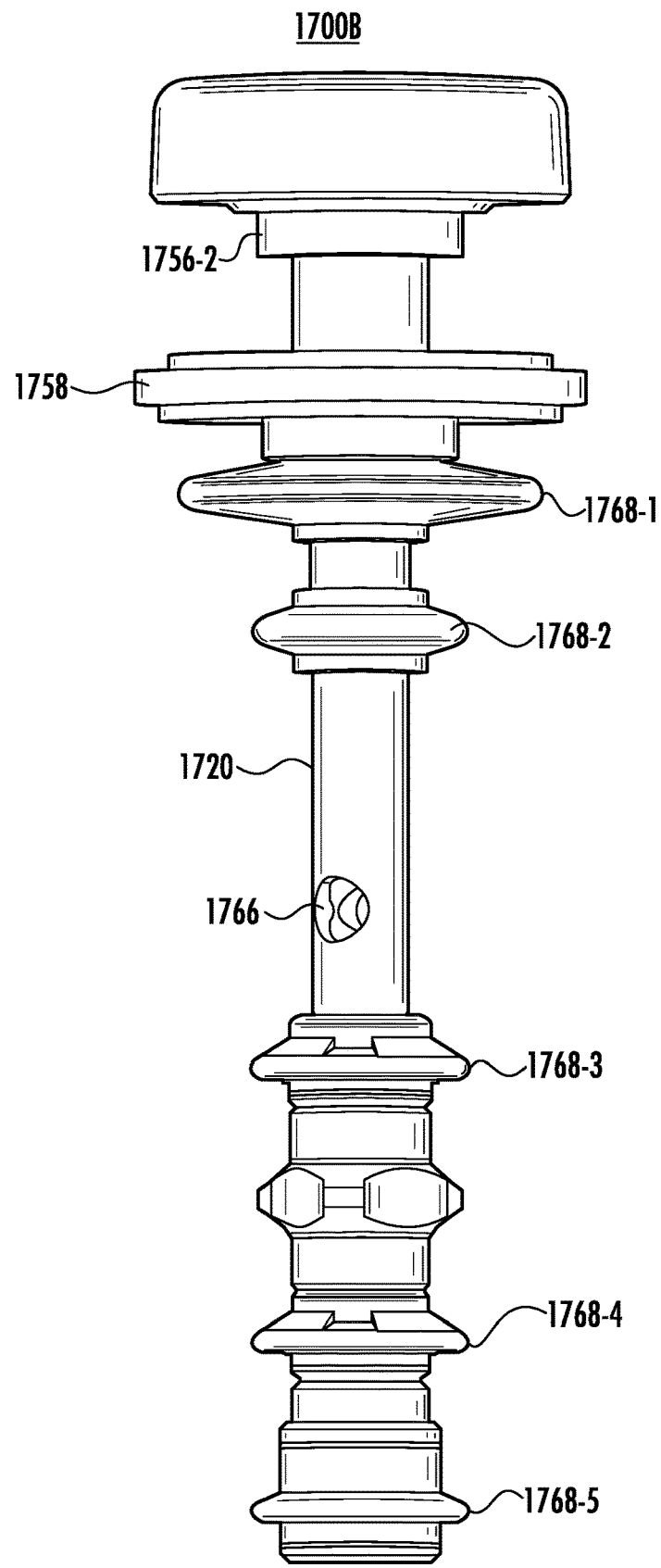

Referring to FIG. 17A, environment 1700A illustrates a perspective view of AW valve assembly 1702. In the illustrated embodiment, AW valve assembly 1702 may include an interface 1752, biasing member 1728-2, housing 1762, and AW valve well 1704 with air input channel 1706, water input channel 1708, air output channel 1710, water output channel 1712, and balloon channel 1714. Referring to FIG. 17B, environment 1700B illustrates an assembly stage of the AW valve assembly 1702. The illustrated embodiment may include linkage 1756-2, hat 1758, primary control valve 1720 with radial air hole 1766 and seals 1768-1, 1768-2, 1768-3, 1768-4, 1768-5.

Figure 17C:
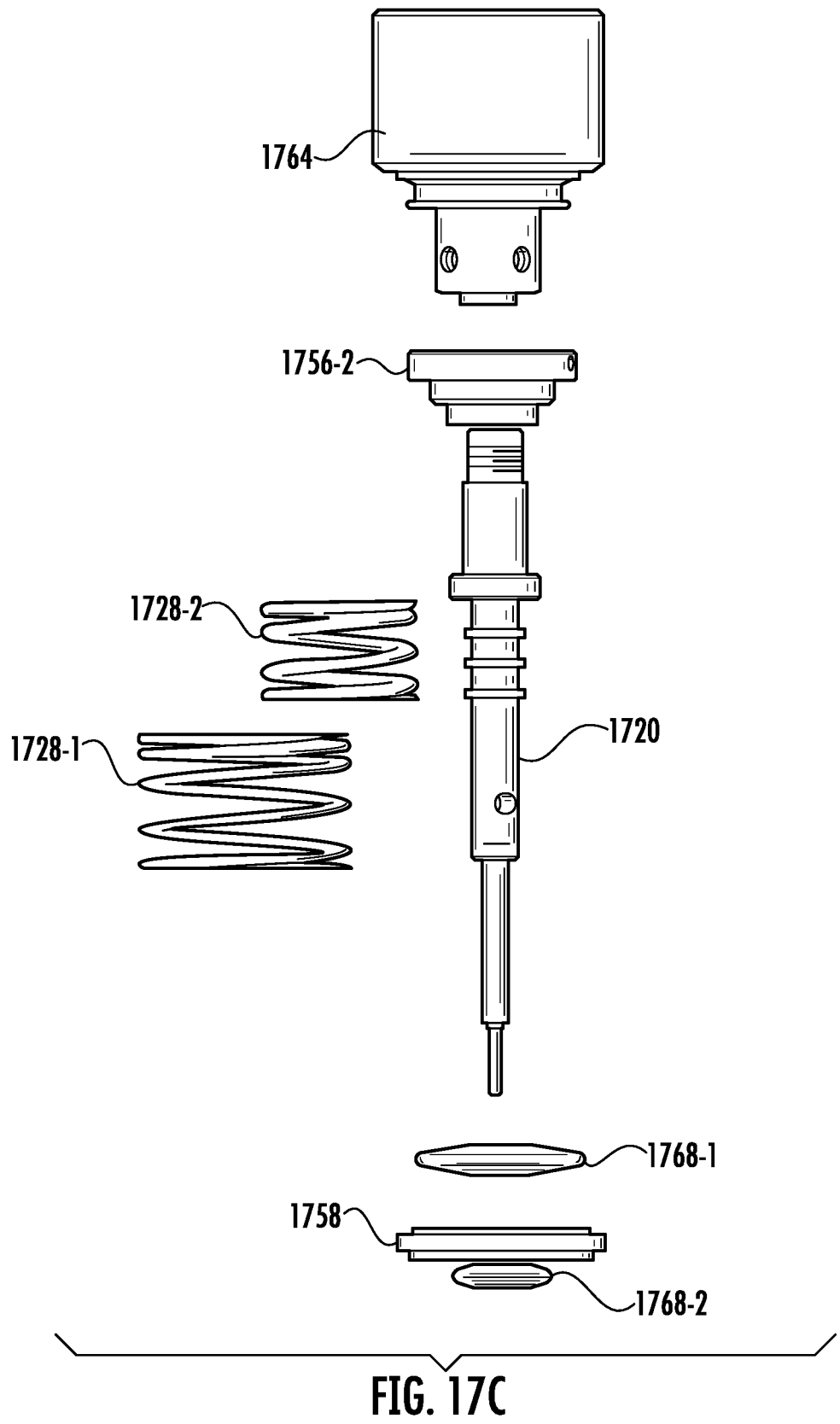
Figure 17D:
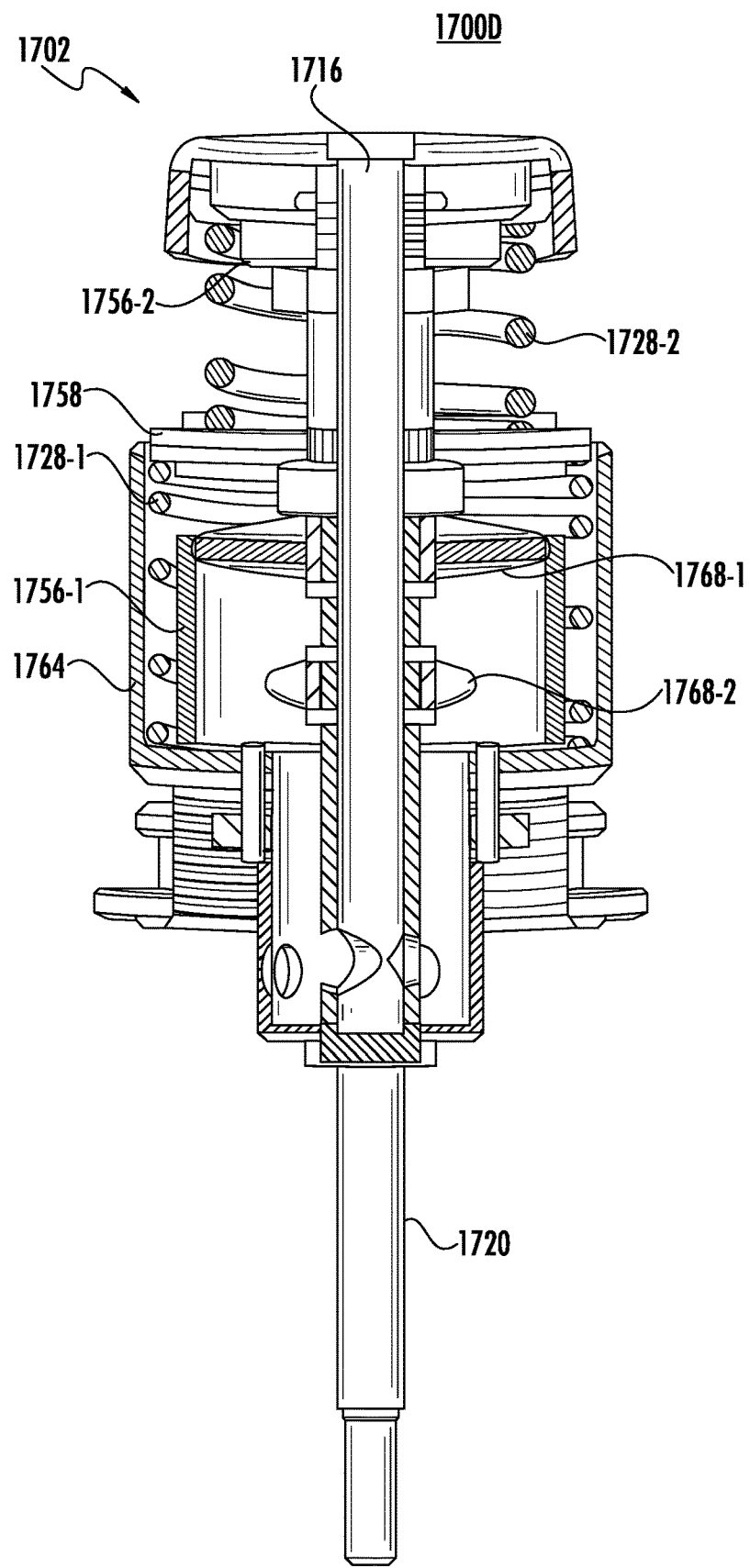

Referring to FIG. 17C, environment 1700C illustrates an exploded view of various components of AW valve assembly 1702. The illustrated embodiment may include bowl 1764, linkage 1756-2, biasing members 1728-1, 1728-2, primary control valve 1720, seals 1768-1, 1768-2, and hat 1758. Referring to FIG. 17D, environment 1700D illustrates a cross-sectional view of various components of AW valve assembly 1702. In the illustrated embodiment, AW valve assembly 1702 may include linkages 1756-1, 1756-2, hat 1758, biasing members 1728-1, 1728-2, bowl 1764, and primary control valve 1720 with at least a portion of atmospheric channel 1716 and seals 1768-1, 1768-2. In various embodiments, linkage 1756-1 may comprise a portion of the bowl 1764. For example, linkage 1756-1 may be a circumferential wall that separates a biasing member seat from another region of the bowl 1764 (see e.g., biasing member seat 2278-3 and region 2280-1 of bowl 2264 in FIG. 22E).

Figure 18C:
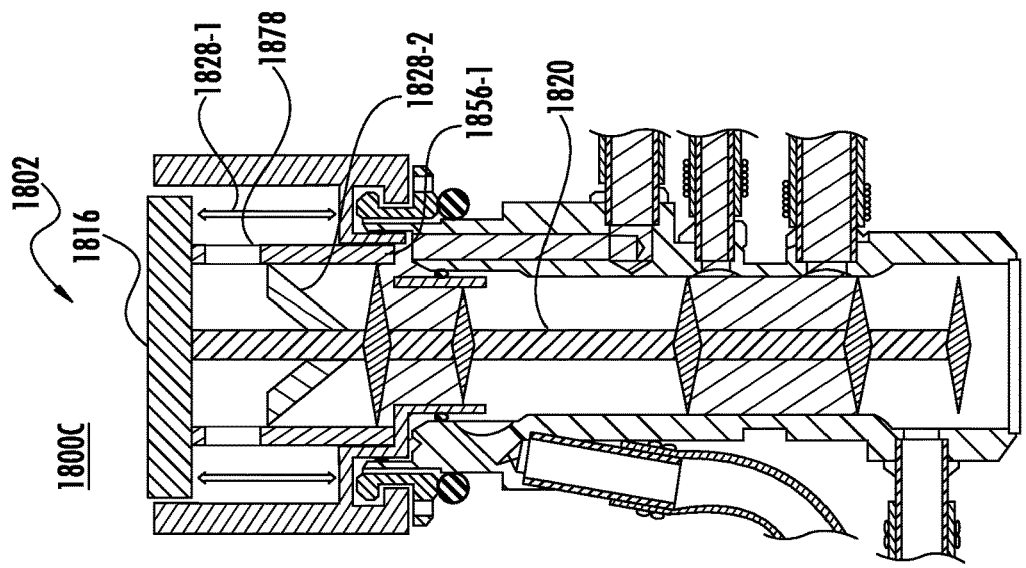
FIGS. 18A-18C illustrate various aspects of an exemplary AW valve assembly, according to one or more embodiments described herein.
Figure 18B:
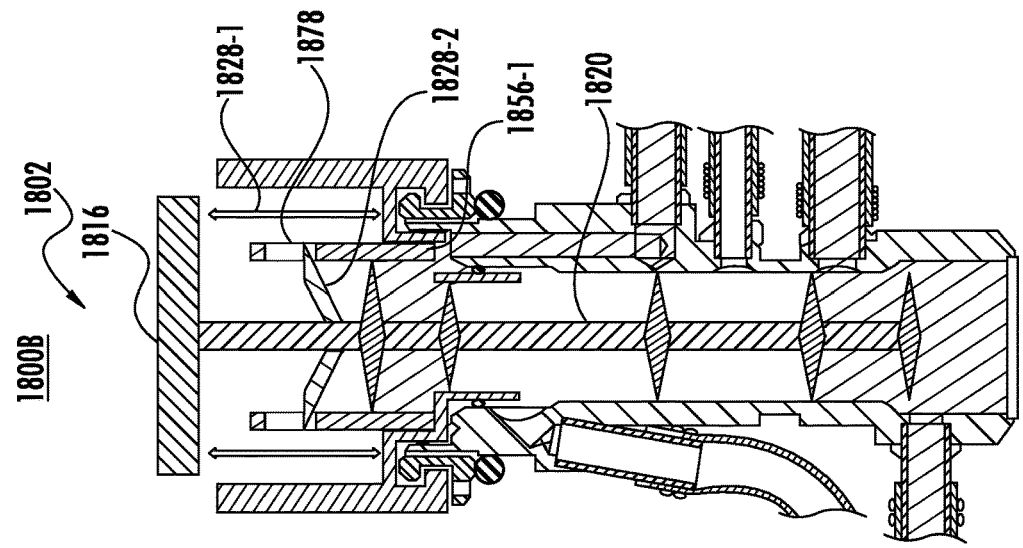
Figure 18A:
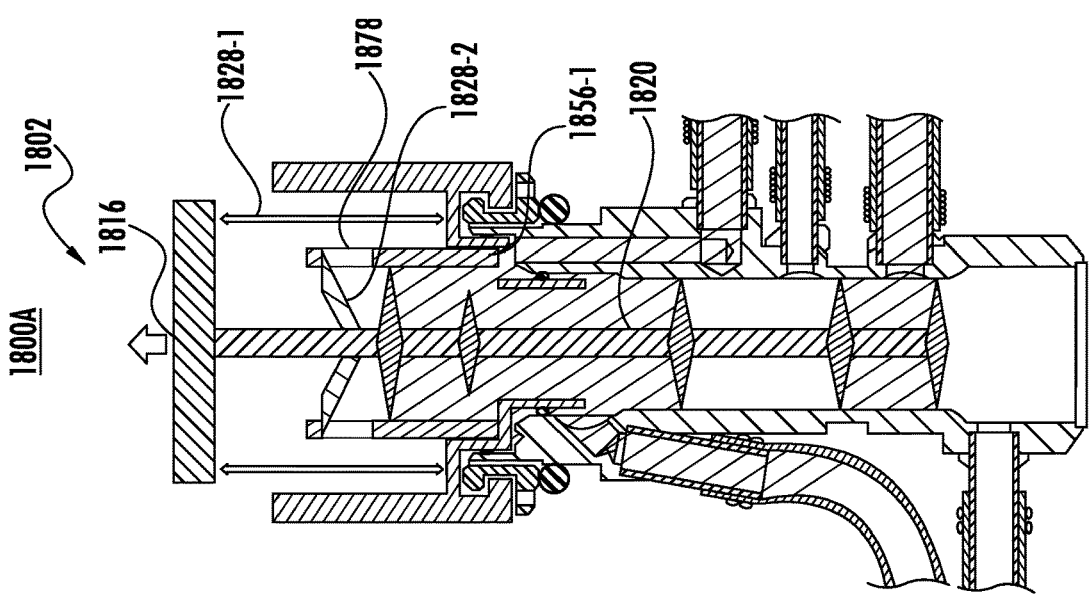

FIGS. 18A-18C illustrate various aspects of an exemplary AW valve assembly 1802 in environments 1800A, 1800B, 1800C according to one or more embodiments described herein. In many embodiments, a cross section of one or more components may be illustrated in environments 1800A, 1800B, 1800C. In some embodiments, one or more components of FIGS. 18A-18C may be the same or similar to one or more other components described herein. Environments 1800A, 1800B, 1800C may include an AW valve assembly 1802. In many embodiments, the AW valve assembly 1802 may be the same or similar to AW valve assemblies 1602, 1702 with the exception of biasing member 1828-2 and vertical slot 1878 in linkage 1856-1. In one or more embodiments described herein, biasing member 1828-2 may include a set of one or more cantilever spring arms with first ends coupled to the primary control valve 1820. In one or more such embodiments, the set of one or more cantilever spring arms may have second ends disposed in corresponding vertical slots in linkage 1856-1. Further, the one or more cantilever spring arms may be able to slide up and down in the corresponding vertical slots. Embodiments are not limited in this context.

Environment 1800A may include the AW valve assembly 1802 in an air escape state. However, by sealing the atmospheric channel 1816, such as with an atmospheric valve or a finger, AW valve assembly 1802 may transition into an air delivery state. Environment 1800B may include the AW valve assembly 1802 in a water delivery state and environment 1800C may include the AW valve assembly 1802 in a balloon fill state. In various embodiments, AW valve assembly 1802 may utilize the biasing member 1828-2 to provide tactile feedback through the entire travel of the primary control valve 1820. Accordingly, biasing member 1828-2 contacting the bottom of the vertical slot 1878 may provide first feedback and biasing member 1828-2 reaching a flex limit may provide second feedback. In many embodiments, biasing member 1828-1 may bias the AW valve assembly into the configuration illustrated in environment 1800A (FIG. 18A).

Figure 19:
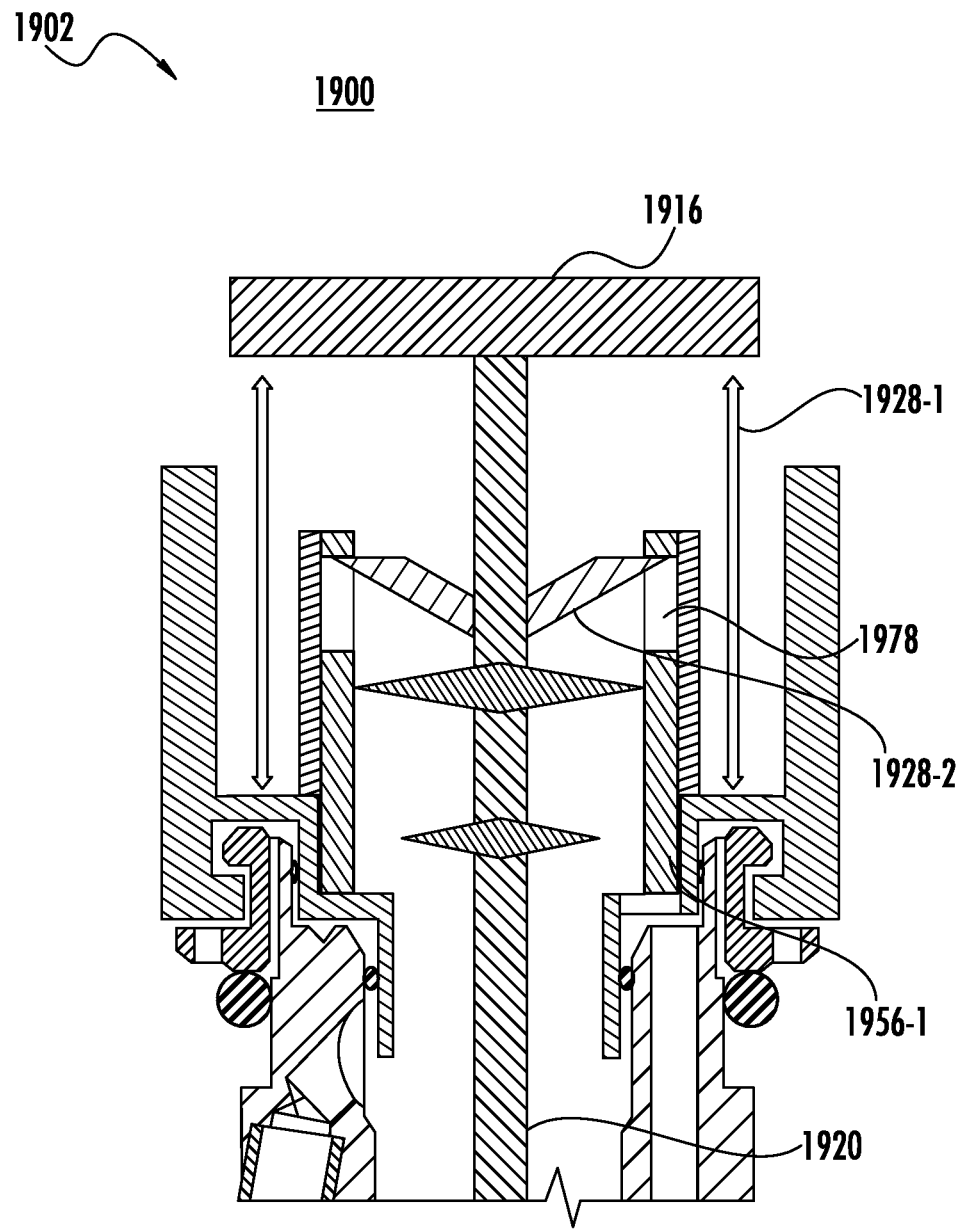
FIG. 19 illustrates various aspects of an exemplary AW valve assembly, according to one or more embodiments described herein.

FIG. 19 illustrates various aspects of an exemplary AW valve assembly 1902 in environment 1900, according to one or more embodiments described herein. In many embodiments, a cross section of one or more components may be illustrated in environment 1900. In some embodiments, one or more components of FIG. 19 may be the same or similar to one or more other components described herein. In many embodiments, the AW valve assembly 1902 may be the same or similar to AW valve assembly 1802 with the exception of circumferential slot 1978. Accordingly, instead of having one or more vertical slots, AW valve assembly 1902 may include a single slot that extends around the inner circumference of linkage 1956-1. In some embodiments, this may simplify assembly by removing the need for rotational control (e.g., aligning cantilever arms with vertical slots). Embodiments are not limited in this context.

Figure 20A:
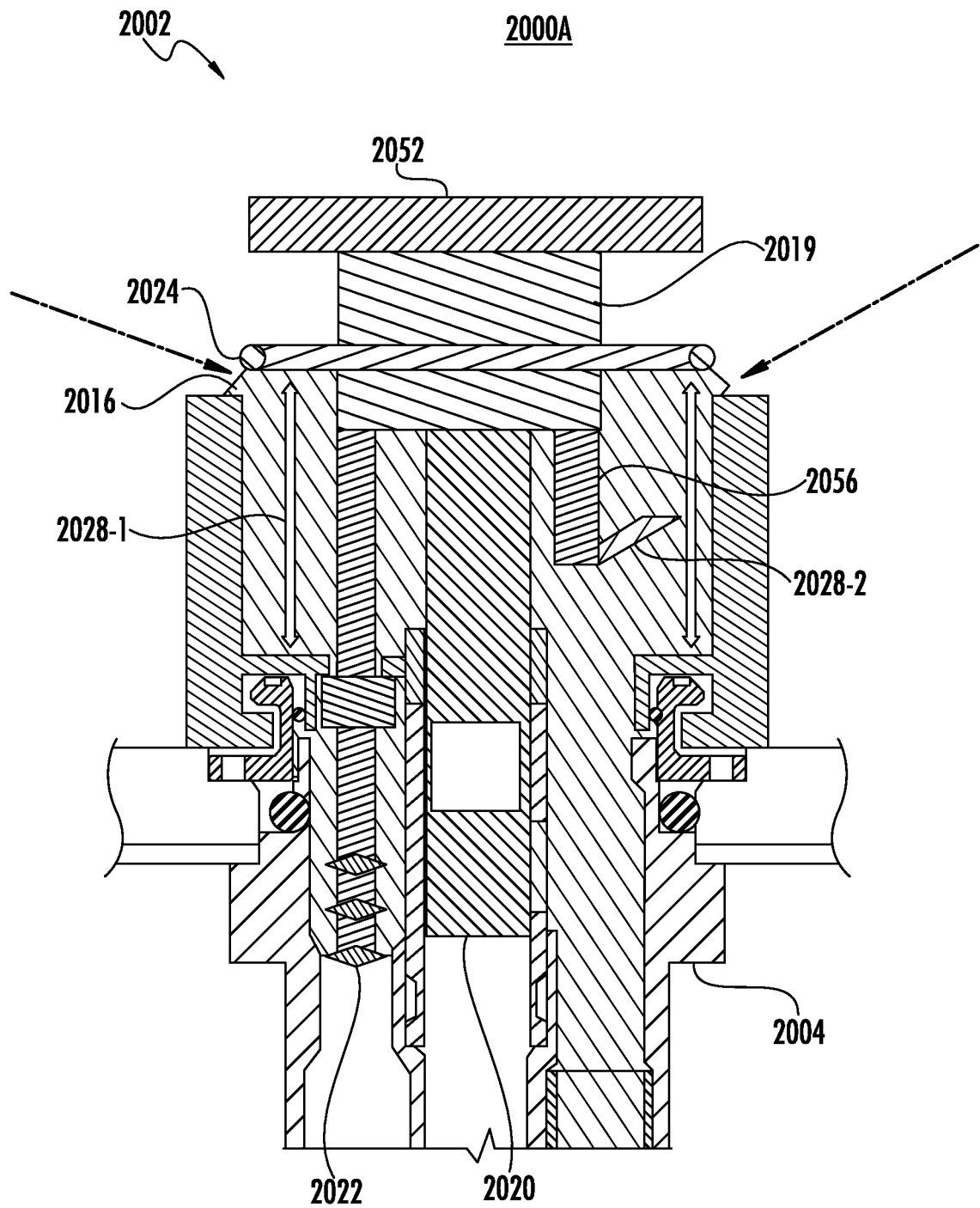
FIGS. 20A-20C illustrate various aspects of an exemplary suction valve assembly, according to one or more embodiments described herein.
Figure 20B:
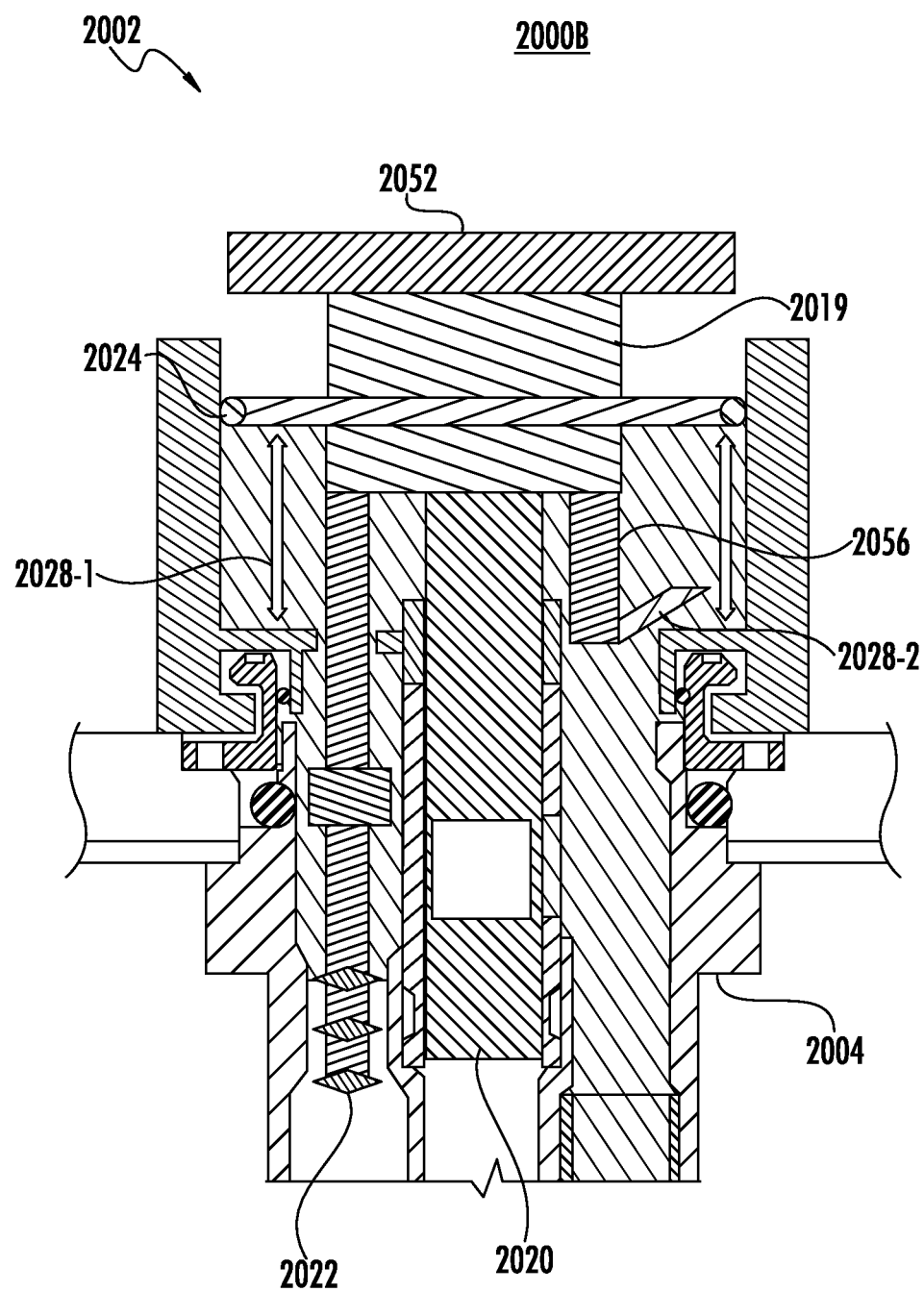
Figure 20C:
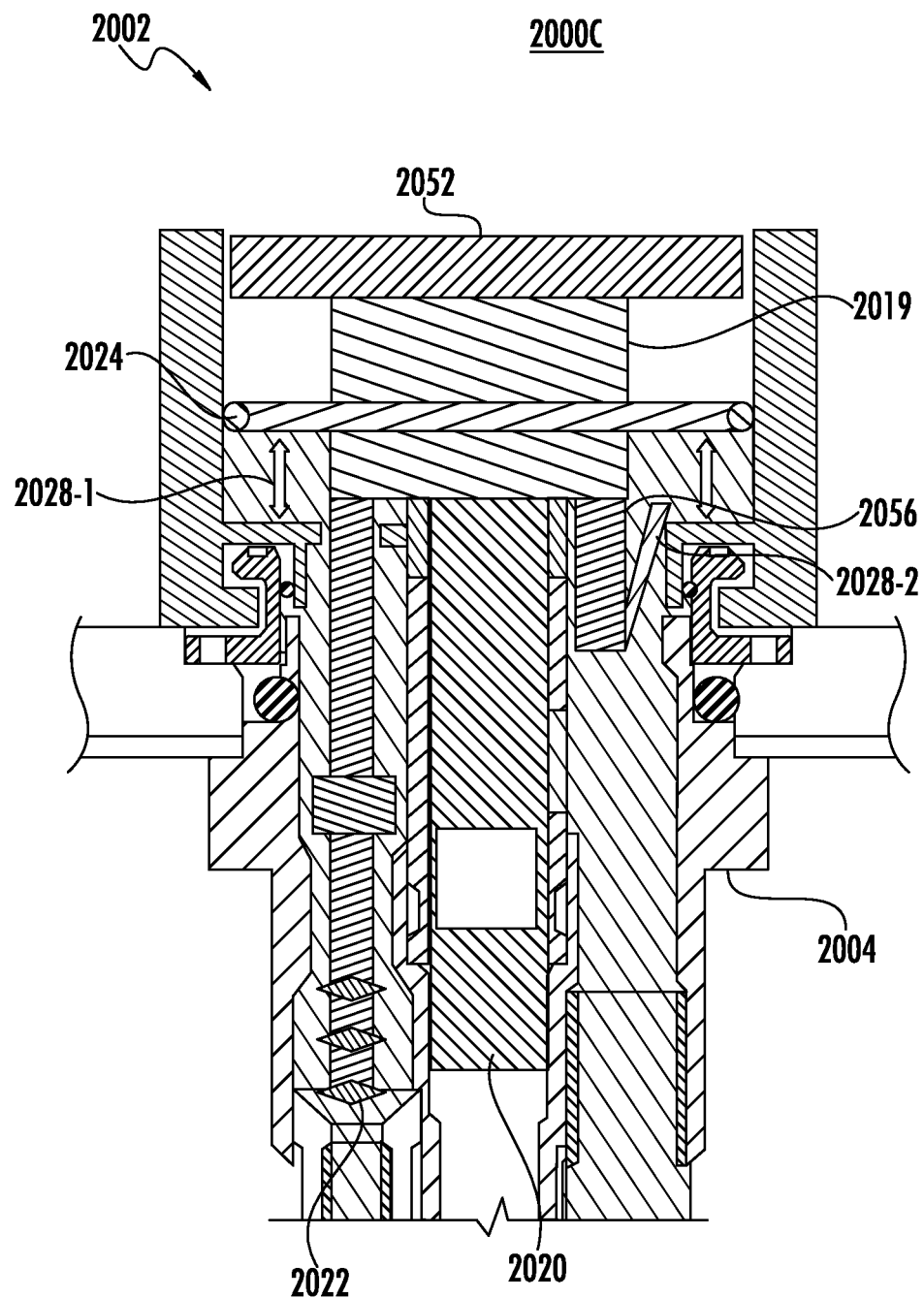

FIGS. 20A-20C illustrate various aspects of an exemplary suction valve assembly 2002 in environments 2000A, 2000B, 2000C according to one or more embodiments described herein. In many embodiments, a cross section of one or more components may be illustrated in environments 2000A, 2000B, 2000C. In some embodiments, one or more components of FIGS. 20A-20C may be the same or similar to one or more other components described herein. Environments 2000A, 2000B, 2000C may include a suction valve assembly 2002. The illustrated embodiment of suction valve assembly 2002 includes interface 2052, valve mechanism 2019, atmospheric valve 2024, biasing members 2028-1, 2028-2, linkage 2056, balloon valve 2022, working channel valve 2020, and suction valve well 2004. In one or more embodiments described herein, the valve mechanism 2019 may be configured to move the balloon valve 2022 and the working channel valve 2020 in unison. In the illustrated embodiment, the valve mechanism 2019 is configured to move the balloon valve 2022, the working channel valve 2020, and the atmospheric valve 2024 in unison. Embodiments are not limited in this context.

In several embodiments, suction valve assembly 2002, may combine the shafts of the balloon valve 2022 and the working channel valve 2020 into a single body. As shown in environment 2000B, in many embodiments, tactile feedback of the first stop may be provided by biasing member 2028-2 (e.g., a cantilever spring) that is used to indicate when the valve has been pushed/displaced to a working channel suction state. Further, as shown in environment 2000C, the biasing member 2028-2 may flex towards linkage 2056 and enter, at least in part, the suction channel to indicate the balloon suction state.

FIGS. 21A-21D illustrate various aspects of an exemplary AW valve assembly 2102 in environments 2100A-2100D, according to one or more embodiments described herein. In many embodiments, a cross section of one or more components may be illustrated in environments 2100A-2100D. In some embodiments, one or more components of FIGS. 21A-21D may be the same or similar to one or more other components described herein. Environments 2100A-2100D may include one or more portions of the AW valve assembly 2102. In one or more embodiments described herein, AW valve assembly 2102 may include a skirt seal to provide reliable, intuitive, and ergonomic control of fluid through the AW valve well 2104. Embodiments are not limited in this context.

Figure 21A:
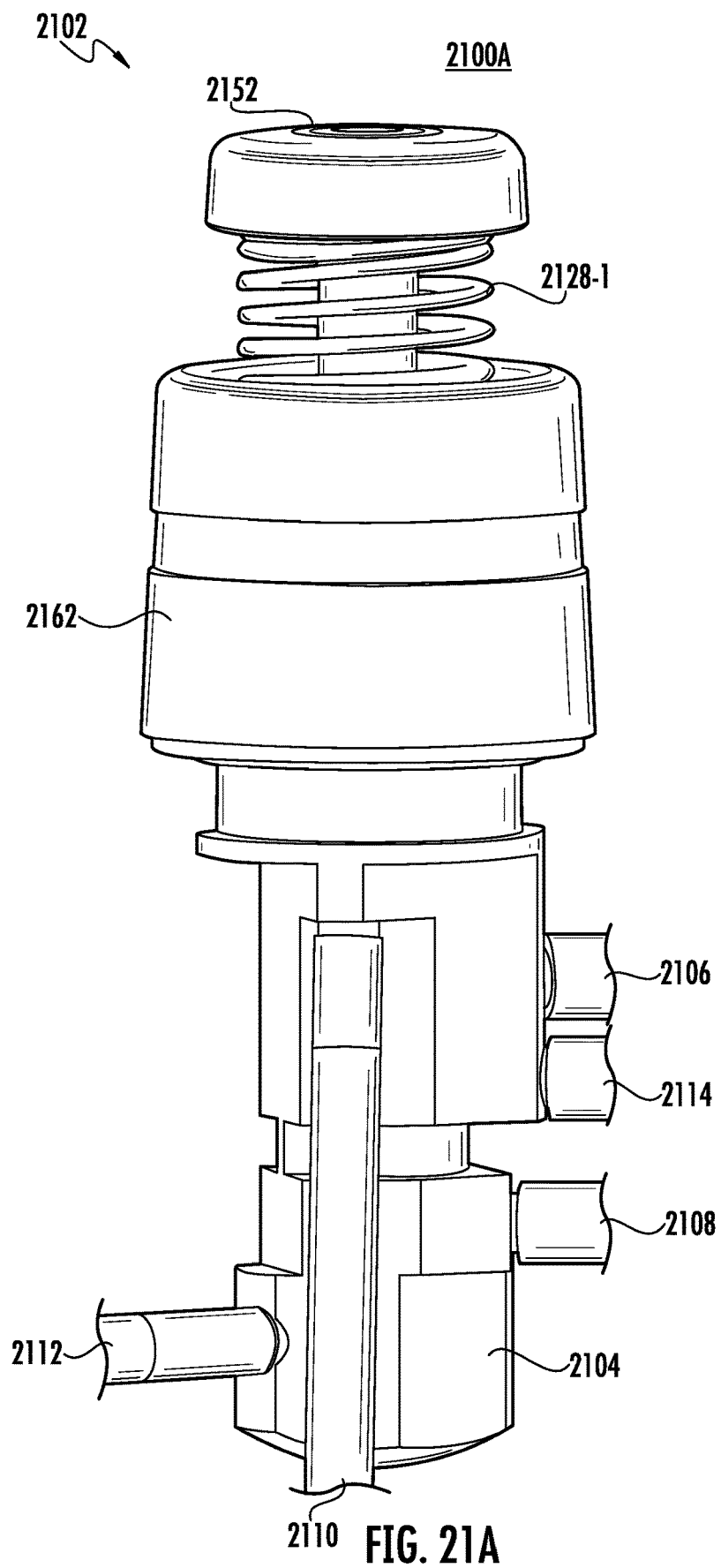
FIGS. 21A-21D illustrate various aspects of an exemplary AW valve assembly, according to one or more embodiments described herein.
Figure 21B:
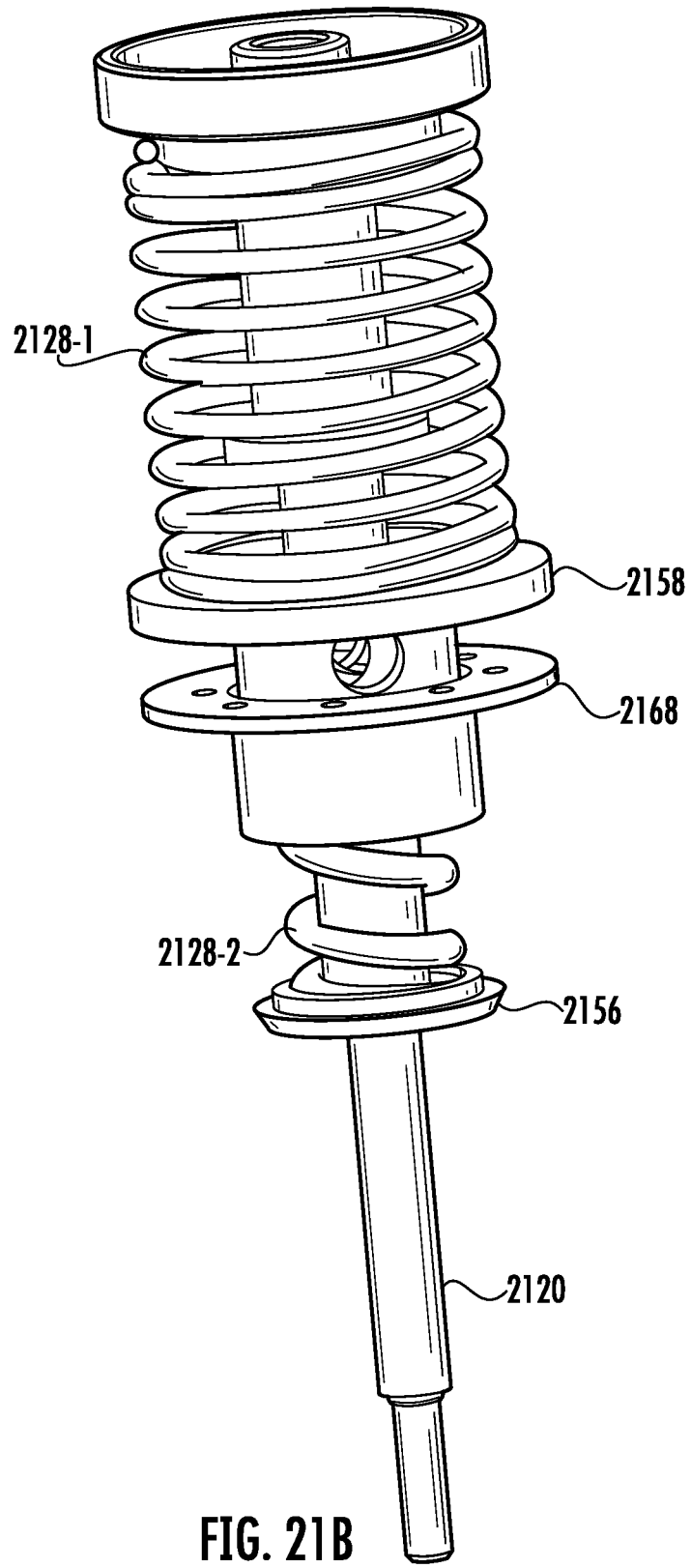

Referring to FIG. 21A, environment 2100A illustrates a perspective view of AW valve assembly 2102. In the illustrated embodiment, AW valve assembly 2102 may include an interface 2152, biasing members 2128-2, housing 2162, and AW valve well 2104 with air input channel 2106, water input channel 2108, water output channel 2112 and balloon channel 2121. Referring to FIG. 21B, environment 2100B illustrates an assembly stage of the AW valve assembly 2102. The illustrated embodiment may include biasing members 2128-1, 2128-2, hat 2158, skirt seal 2168, linkage 2156, and primary control valve 2120. In various embodiments, the skirt seal 2168 may provide a reliable closure mechanism to prevent reverse flow into primary control valve 2120. In many embodiments, the skirt seal 2168 can simplify the design, geometry, assembly, and/or manufacture of one or more components of AW valve assembly 2102, such as bowl 2164 and/or primary control valve 2120.

Figure 21C:
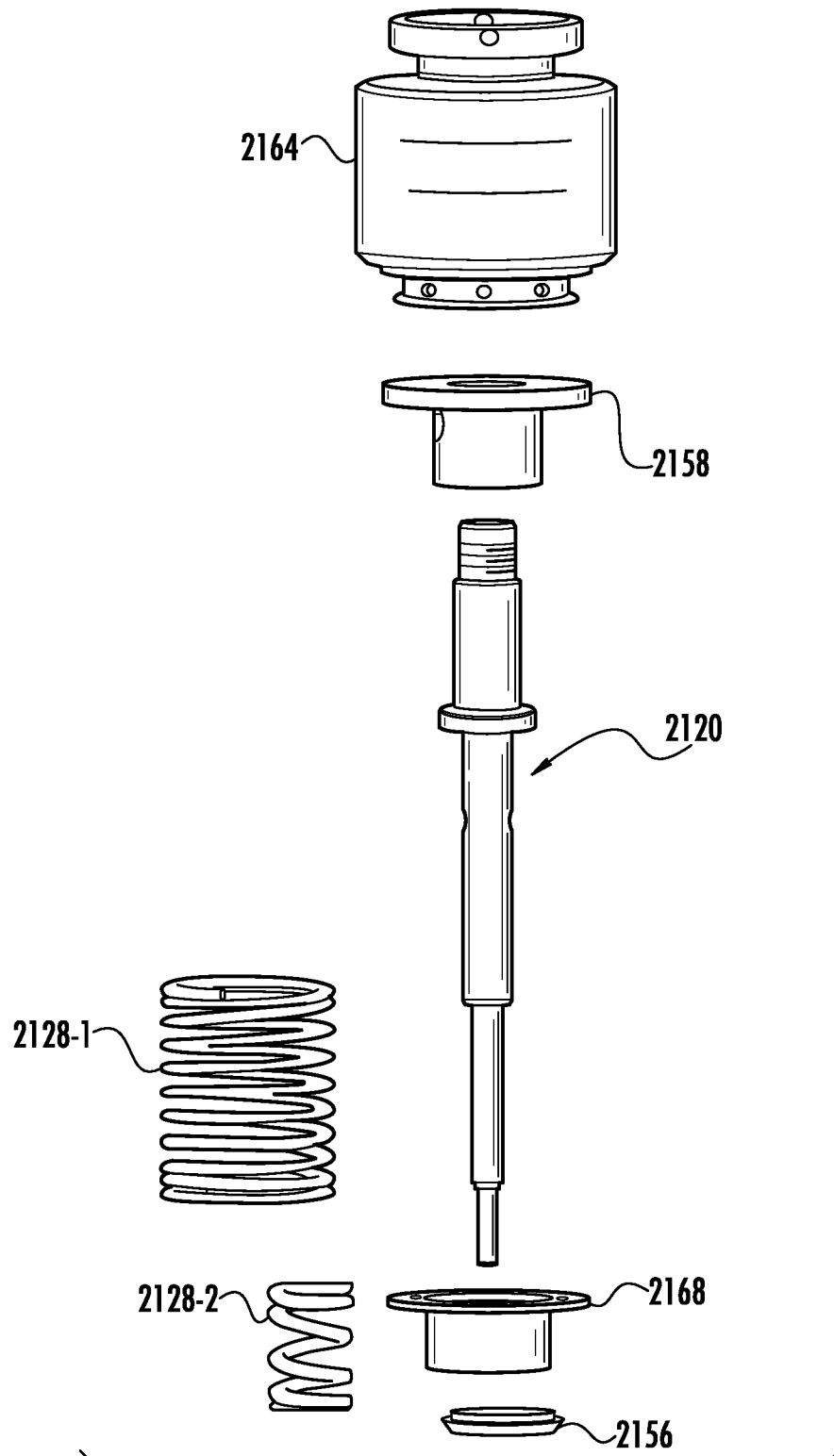
Figure 21D:
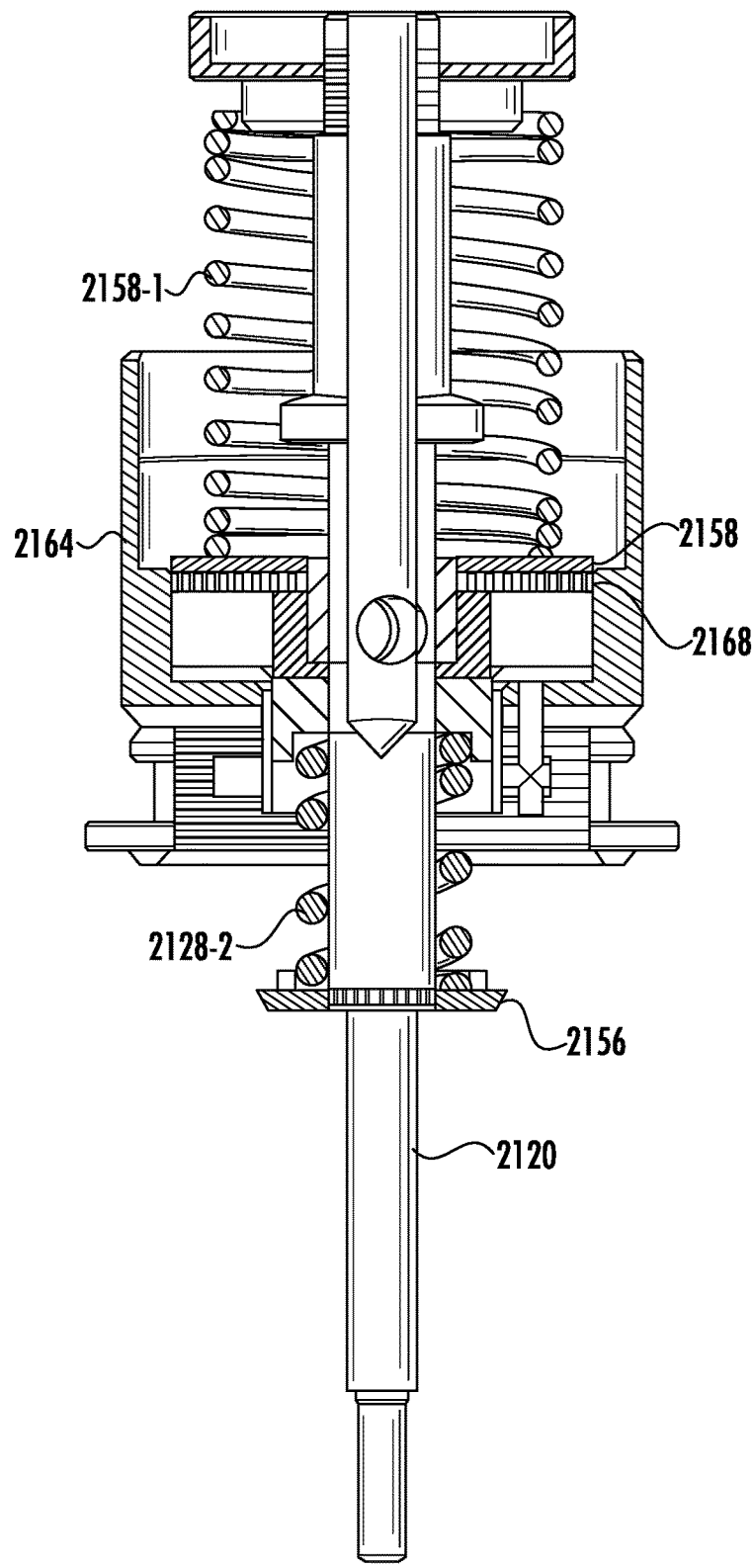

Referring to FIG. 21C, environment 2100C illustrates an exploded view of various components of suction valve assembly 2102. The illustrated embodiment may include bowl 2164, hat 2158, primary control valve 2120, biasing members 2128-1, 2128-2, and skirt seal 2168. Referring to FIG. 21D, environment 2100D illustrates a cross-sectional view of various components of suction valve assembly 2102. In the illustrated embodiment, AW valve assembly 2102 may include biasing members 2128-1, 2128-2, bowl 2164, hat 2158, skirt seal 2168, linkage 2156, and primary control valve 2120.

In various embodiments, when venting to atmosphere (e.g., air escape state), flow may travel across and through holes in bowl 2164, into the primary control valve 2120, and out of the top primary control valve. When the top (e.g., atmospheric channel) is covered, flow is forced out of the inner circumference of the bowl 2164 and under skirt seal 2168, thereby pushing the skirt seal 2168 inwards and open. This may be opposite of the flapper 2267 of AW valve assembly 2202, as will be discussed in more detail below. When the interface 2152 is actuated, the hat 2158 moves down and seals both the holes in the bowl on the top and seals the skirt seal 2168 to the bowl 2164, preventing flow and compressing biasing member 2128-2. This may also move the distal seals of primary control valve 2120 (see e.g., FIGS. 12A-12C) to allow flow from the water input channel to the water output channel (i.e., water delivery state). Biasing member 2128-1 may be compressed to transition to the balloon fill state. In various embodiments, one or more components of valve assemblies may fit with sufficiently tight tolerances to provide a seal with one or more other components, such as by assembling the valve set and/or valve interface mechanism into a valve well. The primary control valve 2120 may also include a seal to prevent airflow into water channels.

FIGS. 22A-22H illustrate various aspects of an exemplary AW valve assembly 2202 in environments 2200A-2200H, according to one or more embodiments described herein. In many embodiments, a cross section of one or more components may be illustrated in environments 2200A-2200H. In some embodiments, one or more components of FIGS. 22A-22H may be the same or similar to one or more other components described herein. For instance, AW valve assembly 2202 may be the same or similar to AW valve assembly 1602 and/or AW valve assembly 1702. Environments 2200A-2200H may include one or more portions of the AW valve assembly 2202. In one or more embodiments described herein, AW valve assembly 2202 may include a set of components to control fluid flow (e.g., air and/or water flow) through an AW valve well when assembled into the valve well. In one or more such embodiments, utilization of the set of components may provide reliable, intuitive, and ergonomic control of fluid through an AW valve well (e.g., AW valve well 1704). Additionally, or alternatively, utilization of seals to control fluid flow through the valve well may simplify manufacturing and/or assembly. Embodiments are not limited in this context.

Figure 22A:
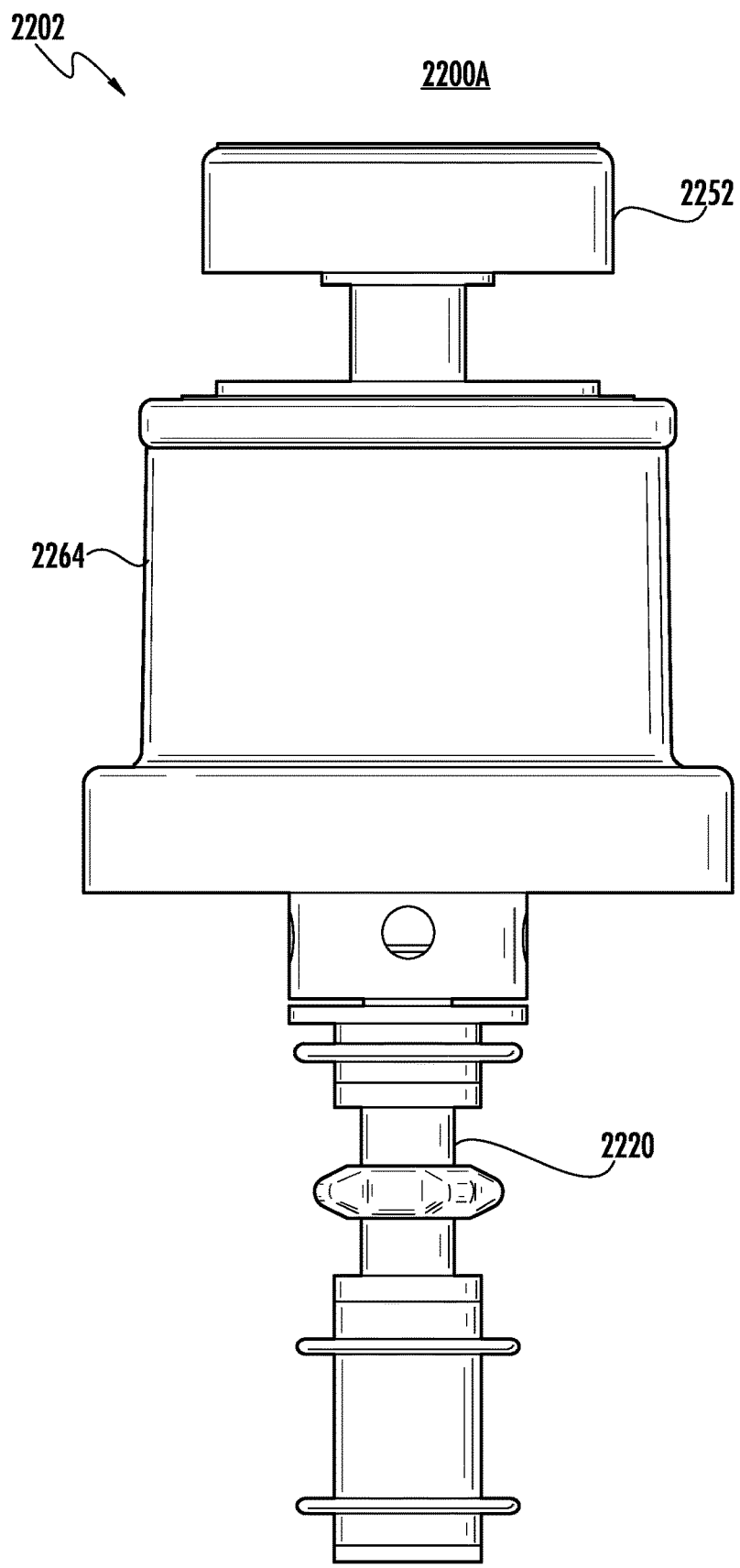
FIGS. 22A-22H illustrate various aspects of an exemplary AW valve assembly, according to one or more embodiments described herein.

Referring to FIG. 22A, environment 2200A illustrates a front view of AW valve assembly 2202. In the illustrated embodiment, AW valve assembly 2202 may include an interface member 2252, bowl 2264, and primary control valve 2220. In various embodiments, the AW valve assembly 2202 may be inserted into an AW valve (e.g., AW valve well 2104). In various such embodiments, the AW valve assembly 2202 may be operated via interface member 2252 to control fluid flow through the AW valve well. Operation of the AW valve assembly 2202 via interface member 2252 may move the primary control valve 2220 up and/or down to control fluid flow through the AW valve well. In many embodiments, the AW valve assembly 2202 may include the AW valve well. In some embodiments, bowl 2264 may comprise a housing for one or more components of the AW valve assembly 2202. As will be discussed in more detail below, in many embodiments, the bowl 2264 may include one or more features to align and/or attach the AW valve assembly to an AW valve well.

Figure 22B:
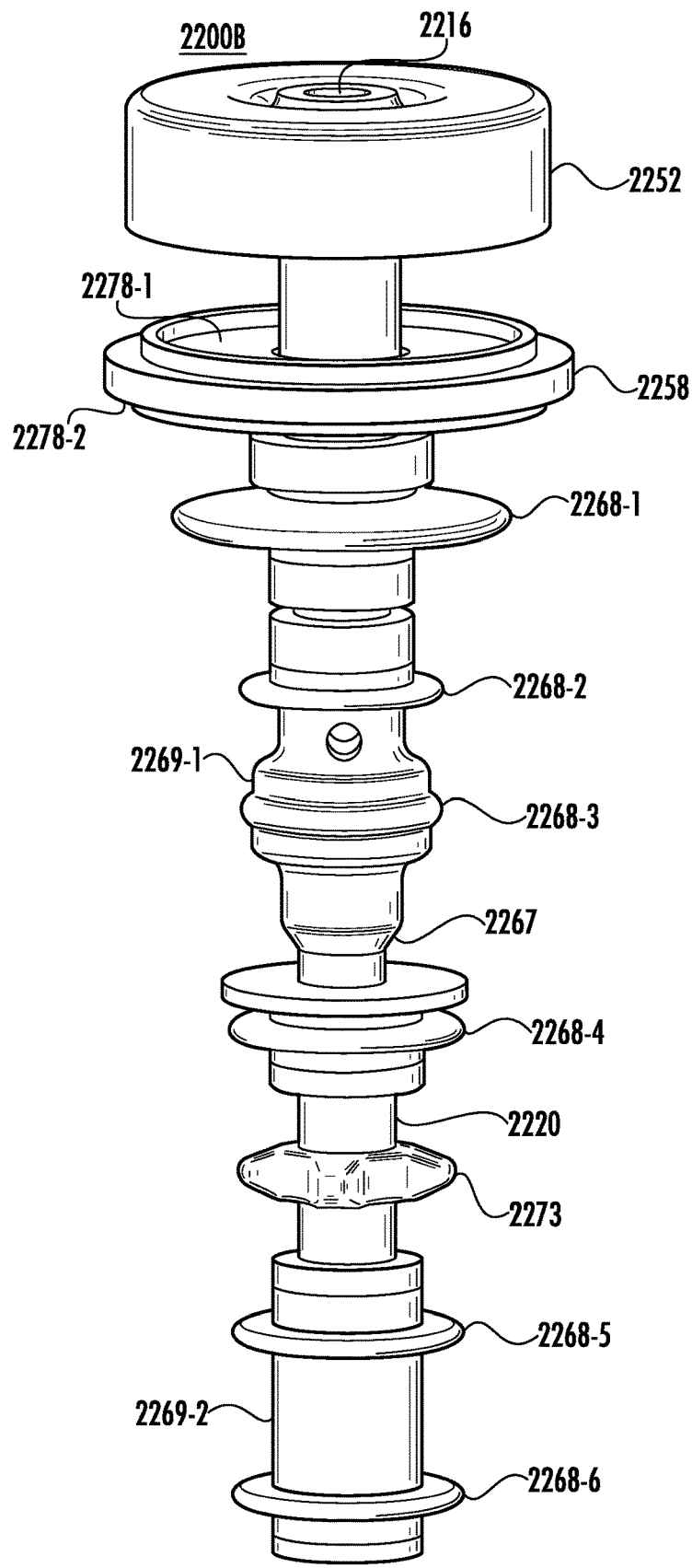

Referring to FIG. 22B, environment 2200B illustrates an assembly stage of the AW valve assembly 2202. The illustrated embodiment may include atmospheric channel 2216, interface member 2252, hat 2258 with biasing member seats 2278-1, 2278-2, seal 2268-1, flow component 2269-1 with seals 2268-2, 2268-3 and flapper 2267, seal 2268-4, primary control valve 2220, stabilizer 2273, and flow component 2269-2 with seals 2268-5, 2268-6. In some embodiments, one or more of the interface member 2252, hat 2258, seal 2268-1, flow component 2269-1, seal 2268-4, stabilizer 2273, and flow component 2269-2 may be comprised in, or disposed along, the primary control valve 2220. Additionally, or alternatively, the primary control valve 2220 may include a lumen comprising atmospheric channel 2216. The biasing member seats 2278 may provide surfaces for biasing members to push against. For example, a biasing member may be included between the biasing member seat 2278 and biasing member seat 2278-4 of interface member 2252 (see FIG. 22H). In another example, a biasing member may be included between biasing member seat 2278-2 and biasing member seat 2278-3 of bowl 2264 (see FIGS. 22E and 22H). These and other aspects of AW valve assembly 2202 will be described in more detail below.

Figure 22C:
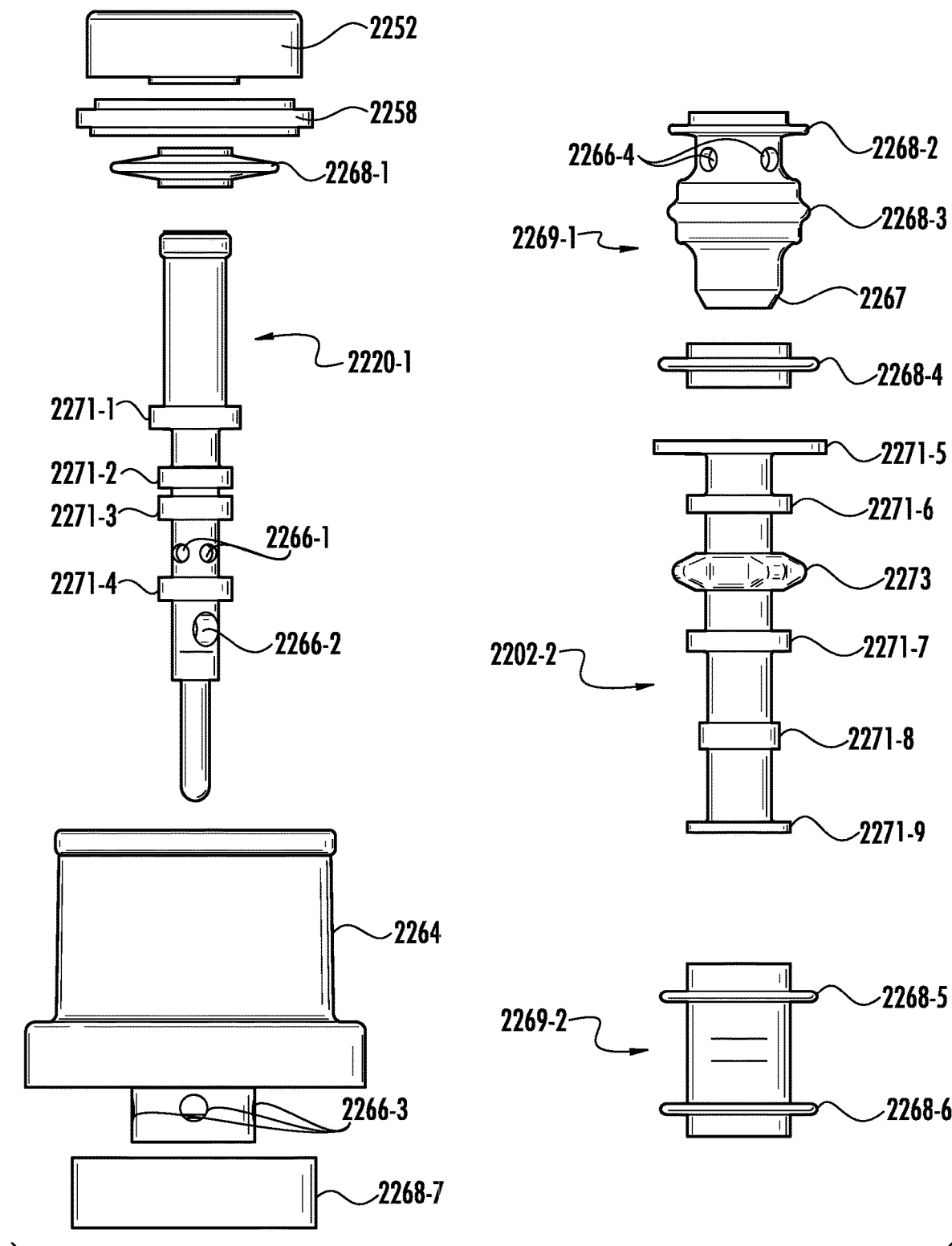

Referring to FIG. 22C, environment 2200C illustrates an exploded view of various components of AW valve assembly 2202. The illustrated embodiment may include interface member 2252, hat 2258, seal 2268-1, primary control valve 2220-1 with flanges 2271-1, 2271-2, 2271-3, 2271-4, a first set of one or more radial holes 2266-1, and a second set of one or more radial holes 2266-2, bowl 2264 with one or more radial holes 2266-3, seal 2268-7, flow component 2269-1 with one or more radial holes 2266-4, flapper 2267, and seals 2268-2, 2268-3, seal 2268-4, primary control valve 2220-2 with stabilizer 2273 and flanges 2271-5, 2271-6, 2271-7, 2271-8, 2271-9, and flow component 2269-2 with seals 2268-5, 2268-6. In various embodiments, the distal end of primary control valve 2220-1 may be inserted into the proximal end of primary control valve 2220-2 to assemble primary control valve 2220. The stabilizer 2273 may assist in keeping the primary control valve 2220 centered in an AW valve well. Further, the shape of the stabilizer 2273 may enable fluid flow to still pass around the stabilizer in the AW valve well.

In various embodiments, one or more of the flanges 2271 may provide a seat, attachment member, retention member, positioning member, manufacturing fixture, and/or the like for one or more other components of the AW valve assembly 2202. For example, seal 2268-1 may seat between flanges 2271-1, 2271-2. In another example, flow component 2269-2 may be overmolded on primary control valve 2220-2 and flanges 2271-7, 2271-9 may provide stops to prevent material run during the overmolding process. Further, flow component 2269-2 may seat onto flange 2271-8. In yet another example, seal 2268-4 may seat between flanges 2271-5, 2271-6. In yet another example, flow component 2269-1 may seat onto flange 2271-4. The assembled relationships between various components is illustrated in FIG. 22H.

Figure 22D:
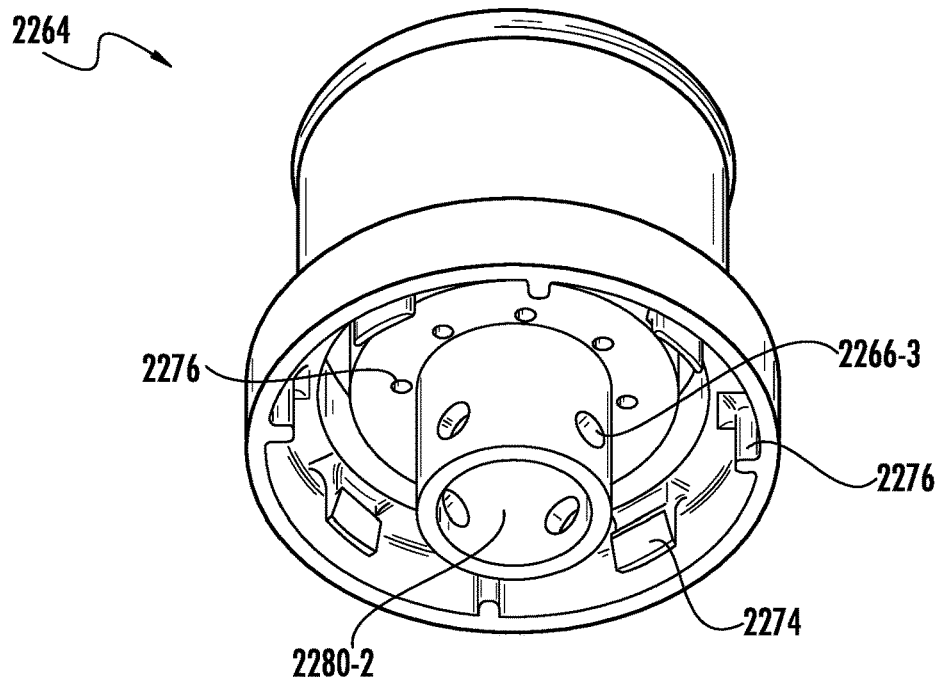
Figure 22E:
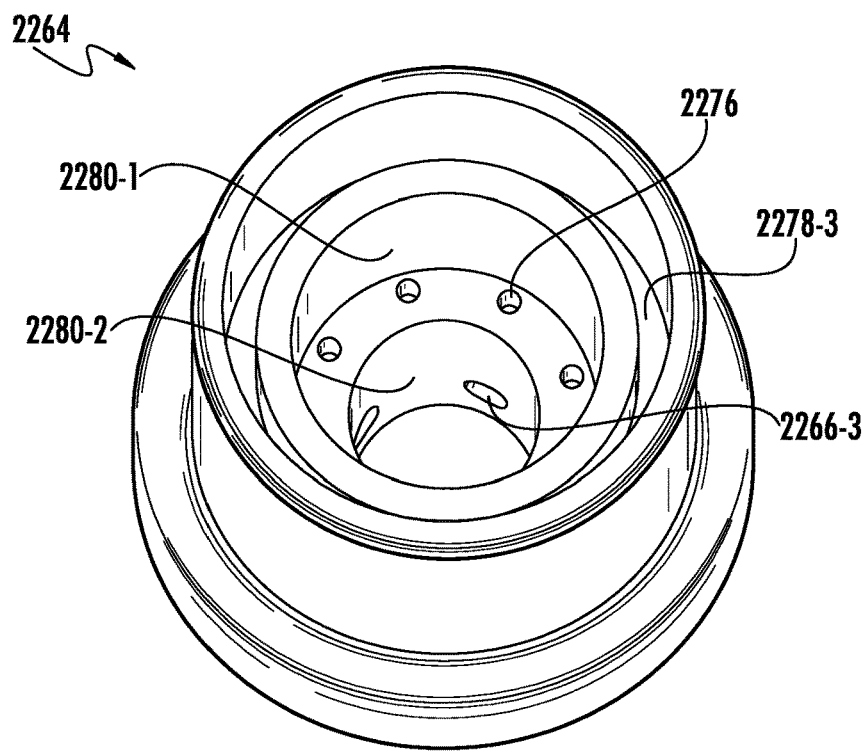

Referring to FIGS. 22D and 22E, environments 2200D, 2200H illustrate various aspects of bowl 2264. Environment 2200D includes a bottom perspective view of bowl 2264 with one or more radial holes 2266-3, one or more vertical holes 2276, one or more retention members 2274, one or more alignment members 2276, and region 2280-2. Environment 2200E includes a top perspective view of bowl 2264 with one or more radial holes 2266-3, one or more vertical holes 2276, regions 2280-1, 2280-2, and biasing member seat 2278-3. In various embodiments, the regions 2280-1, 2280-2 may include separate portions of the bowl with different diameters. As shown in FIG. 22E, region 2280-1 may have a larger diameter than region 2280-2. Also, the one or more vertical holes 2276 may provide fluid access into region 2280-1 while the one or more radial holes 2266-3 may provide fluid access into region 2280-2. In many embodiments, the seal 2268-1 may have the same or similar diameter as region 2280-1 of bowl 2264 to allow the seal 2268-1 to prevent fluid flow within region 2280-1.

In various embodiments, bowl 2264 may include one or more alignment members 2274 to guide proper alignment of the AW valve assembly 2202 with an AW valve well. In many embodiments, the one or more alignment members 2276 may be received by a corresponding one or more slots in the AW valve well. The one or more retention members 2274 may secure the AW valve assembly 2202 to the AW valve well. The biasing member seat 2278-3 may include a circumferential slot for disposing a biasing member, such as a spring. In some embodiments, a spring may be disposed between biasing member seat 2278-3 and biasing member seat 2278-2 of hat 2258.

Figure 22F:
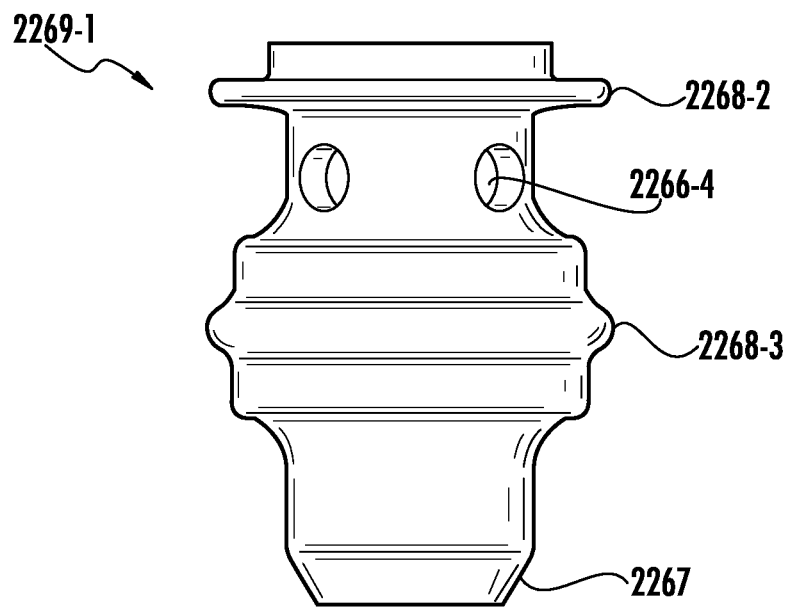
Figure 22G:
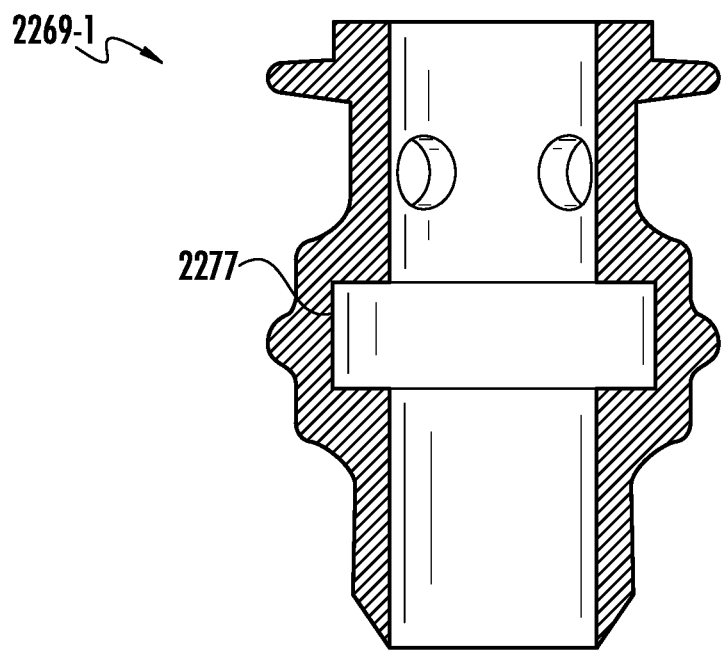
Figure 22H:
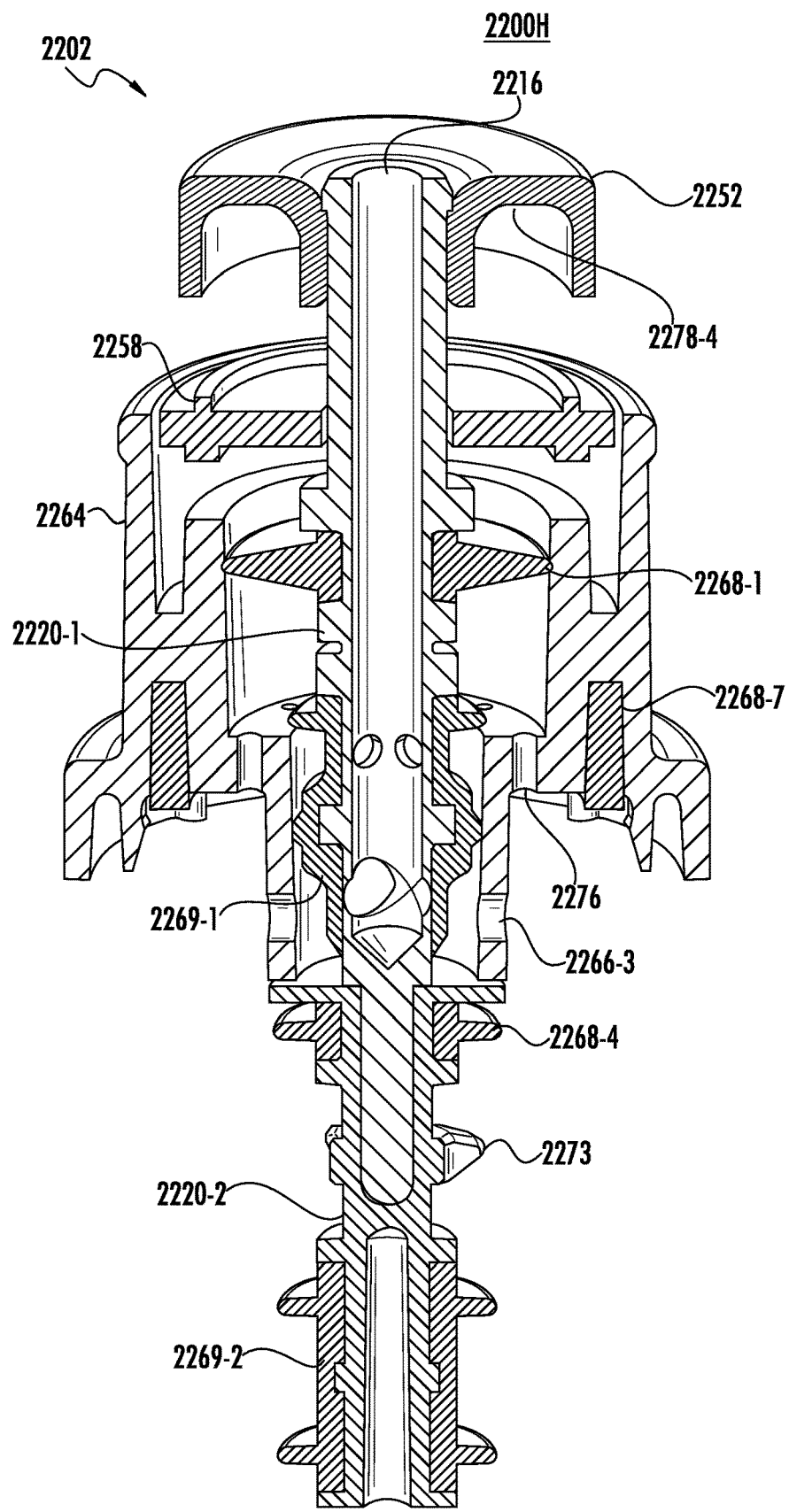

Referring to FIGS. 22F and 22G, environments 2200F, 2200G illustrate various aspects of flow component 2269-1. Environment 2200F includes a side perspective view of flow component 2269-1 with one or more radial holes 2266-4, seals 2268-2, 2268-3, and flapper 2267. Environment 2200G includes a cross-section of flow component 2269-1 illustrating recess 2277. In various embodiments, the recess 2277 may be positioned over flange 2271-4. In many embodiments, the seals 2268-2, 2268-3 may have the same or similar diameter as region 2280-2 of bowl 2264 to allow the seals 2268-2, 2268-3 to prevent fluid flow within region 2280-2. In one or more embodiments, flapper 2267 may flare out to allow fluid to escape when sufficient pressure builds up within the flow component 2269-1. This and other aspects of AW valve assembly 2202 will be described in more detail with respect to FIG. 22H.

Referring to FIG. 22H, environment 2200H illustrates a cross-sectional view of AW valve assembly 2202. In the illustrated embodiment, the assembled relationships between components of the AW valve assembly 2202 is shown. In many embodiments, the one or more vertical holes 2276 may enable fluid from the air input channel of an AW valve well to enter region 2280-1 of bowl 2264. In several embodiments, the one or more radial holes 2266-3 may enable fluid from region 2280-2 of bowl 2264 to pass into the air output channel of an AW valve well.

In many embodiments, the primary control valve 2220 may move up and down with respect to bowl 2264 and an AW valve well to control fluid flow through the AW valve well. As previously mentioned, and described, fluid control through the AW valve well may include an air escape state, an air delivery state, a water delivery state, and a balloon fill state (see e.g., FIGS. 4A-4E).

In the air escape state, air from an air input channel may enter region 2280-1 of bowl 2264 through the one or more vertical holes 2276. Next, the air may pass through radial holes 2266-4 of flow component 2269-1, through radial holes 2266-1 of primary control valve 22020, and out atmospheric channel 2216. In the air escape state, the pressure within the lumen of primary control valve 2220 may not be sufficient to allow air to escape via flapper 2267 of flow component 2269-1.

The air delivery state may include a similar flow path as the air escape state except that the atmospheric channel 2216 is blocked. Accordingly, sufficient pressure is able to build up within the lumen of primary control valve 2220 to allow air to escape via flapper 2267 of flow component 2269-1 into region 2280-2 of bowl 2264. The air may then exit region 2280-2 via radial holes 2266-3 and into the air output channel of an AW valve well. Further, seal 2268-3 may prevent the air from moving into region 2280-1 of bowl 2264 instead of exiting region 2280-2 via radial holes 2266-3 and into the air output channel of an AW valve well.

In the water delivery state, the air input channel may be blocked by trapping air primarily within region 2280-1 of bowl 2264 between seal 2268-1 and seal 2268-2 of flow component 2269-1. Further, by moving seal 2268-2 into region 2280-2 of bowl 2264, air may be prevented from passing through radial holes 2266-4 of flow component 2269-1 and into the lumen of primary control valve 2220. In the water delivery state, the seal 2268-4 and seals 2268-5, 2268-6 of flow component 2269-2 may be arranged in the same or similar manner as illustrated in FIG. 12B.

The balloon fill state may include a similar flow path as the water delivery state. However, in the balloon fill state, seal 2268-1 and seal 2268-2 of flow component 2269-1 may be moved further toward the bottom of the AW valve assembly 2202. In some embodiments, seal 2268-1 may block air from entering region 2280-1 by contacting and sealing vertical holes 2276. In the balloon fill state, the seal 2268-4 and seals 2268-5, 2268-6 of flow component 2269-2 may be arranged in the same or similar manner as illustrated in FIG. 12C.

FIGS. 23A-23D illustrate various aspects of an exemplary AW valve assembly 2302 in environments 2300A-2300D, according to one or more embodiments described herein. In many embodiments, a cross section of one or more components may be illustrated in environments 2300A-2300D. In some embodiments, one or more components of FIGS. 23A-23D may be the same or similar to one or more other components described herein. For instance, AW valve assembly 2302 may be the same or similar to AW valve assembly 1702. Environments 2300A-2300D may include one or more portions of the AW valve assembly 2302. In one or more embodiments described herein, AW valve assembly 2302 may include a set of components to control fluid flow (e.g., air and/or water flow) through an AW valve well when assembled into the valve well. In one or more such embodiments, utilization of the set of components may provide reliable, intuitive, and ergonomic control of fluid through an AW valve well (e.g., AW valve well 1704). Additionally, or alternatively, utilization of seals to control fluid flow through the valve well may simplify manufacturing and/or assembly. Embodiments are not limited in this context.

Figure 23A:
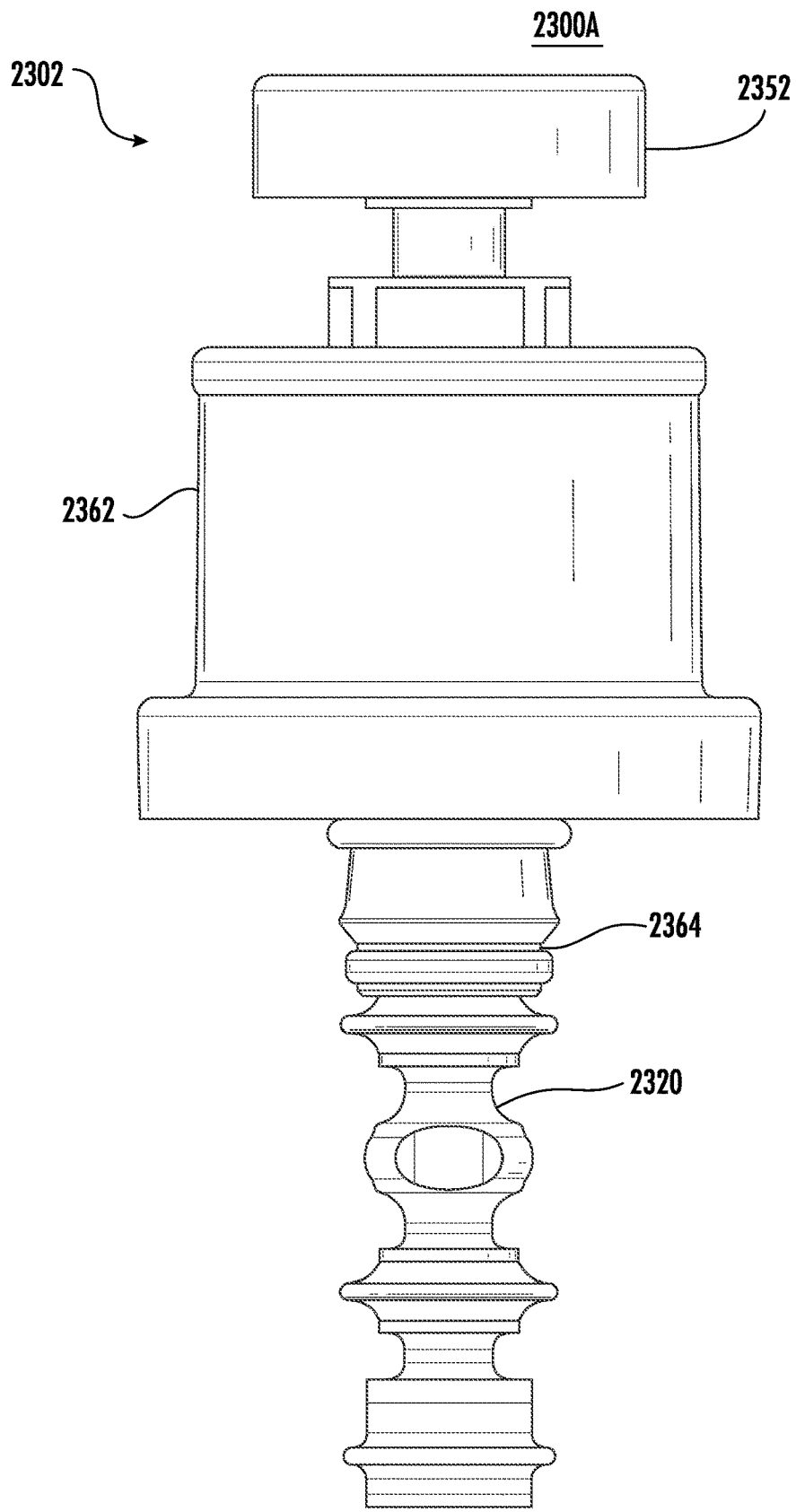
FIGS. 23A-23D illustrate various aspects of an exemplary AW valve assembly, according to one or more embodiments described herein.

Referring to FIG. 23A, environment 2300A illustrates a front view of AW valve assembly 2302. In the illustrated embodiment, AW valve assembly 2302 may include an interface member 2352, bowl 2364, and primary control valve 2320. In various embodiments, the AW valve assembly 2302 may be inserted into an AW valve (e.g., AW valve well 2104). In various such embodiments, the AW valve assembly 2302 may be operated via interface member 2352 to control fluid flow through the AW valve well. Operation of the AW valve assembly 2302 via interface member 2352 may move the primary control valve 2320 up and/or down to control fluid flow through the AW valve well. In many embodiments, the AW valve assembly 2302 may include the AW valve well. In many embodiments, the bowl 2364 may include one or more mating features 2387 to align with and/or attach the housing 2362 of the AW valve assembly to an AW valve well. In several embodiments, the housing 2362 may include one or more features to align and/or attach the AW valve assembly to an AW valve well.

Figure 23B:
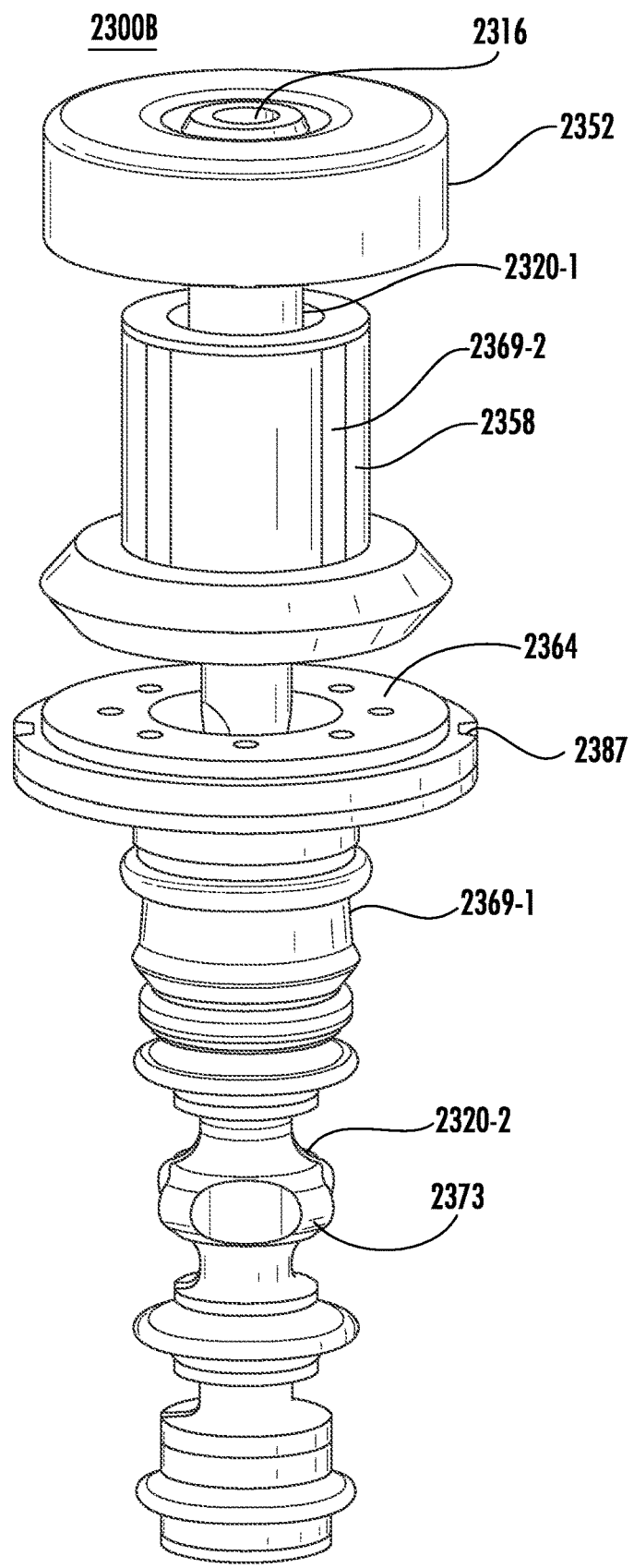

Referring to FIG. 23B, environment 2300B illustrates an assembly stage of the AW valve assembly 2302. The illustrated embodiment may include atmospheric channel 2316, interface member 2352, primary control valve 2320-1, 2320-2, flow components 2369-1, 2369-2, and hat 2358. In some embodiments, one or more of the interface member 2352, hat 2358, seal 2368-1, flow component 2369-1, stabilizer 2373, and flow component 2369-2 may be comprised in, or disposed along, the primary control valve 2320. Additionally, or alternatively, the primary control valve 2320 may include a lumen comprising atmospheric channel 2316. In some embodiments, flow component 2369-2 may be overmolded on hat 2358. One or more embodiments may include a biopsy port interface. In one or more such embodiments, the biopsy port interface may be press-fit. For example, the biopsy port interface may be press-fit onto the primary control valve 2320-1, such as in place of the interface member 2352. These and other aspects of AW valve assembly 2302 will be described in more detail below.

Figure 23C:
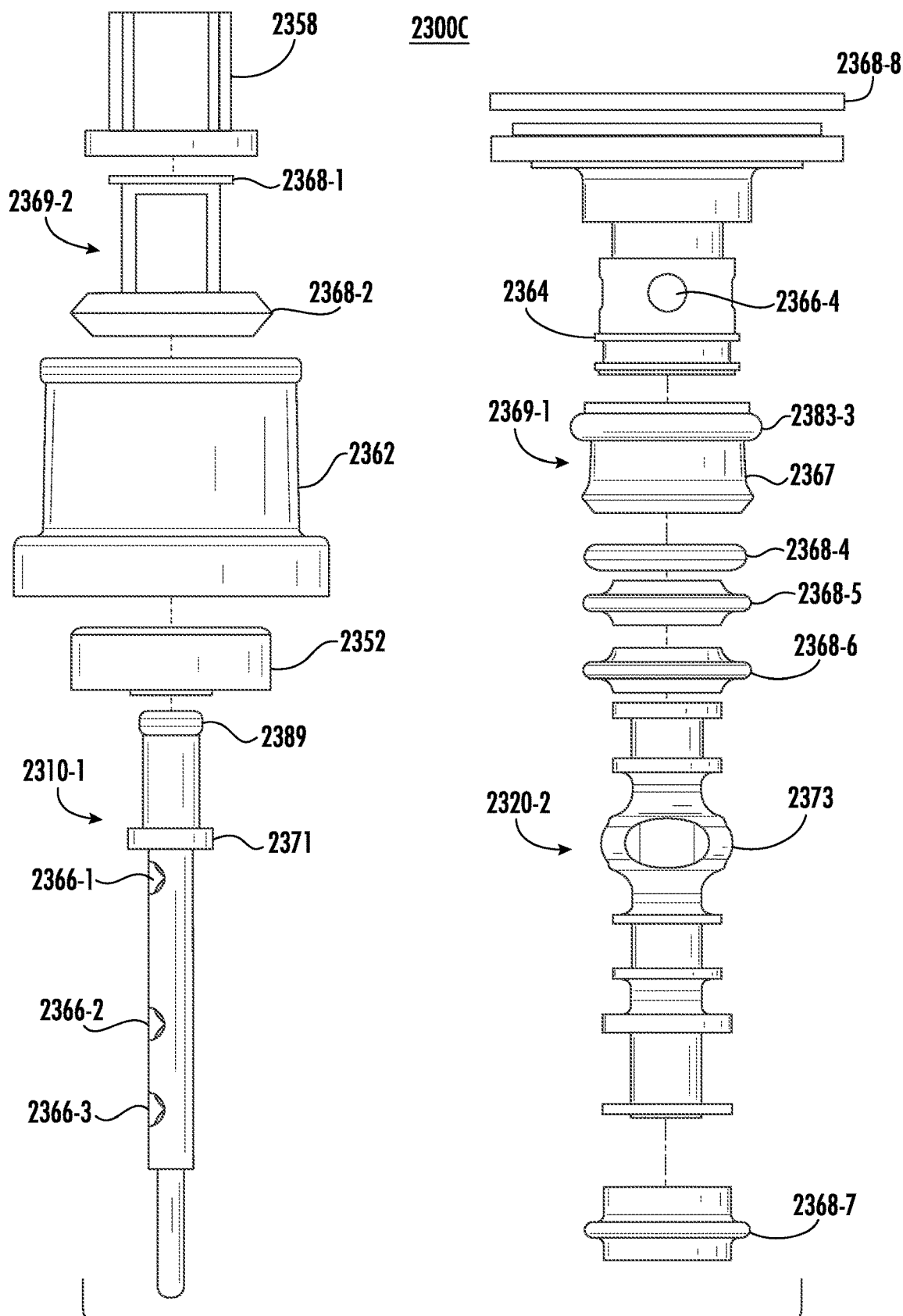

Referring to FIG. 23C, environment 2300C illustrates an exploded view of various components of AW valve assembly 2302. The illustrated embodiment may include hat 2358, flow component 2369-2 with seals 2368-1, 2368-2, housing 2362, interface member 2352, primary control valve 2320-1 with coupler 2389, flange 2371, and one or more radial holes 2366-1, 2366-2, 2366-3, seal 2368-8, bowl 2364 with one or more radial holes 2366-4, flow component 2369-1 with seal 2368-3 and flapper 2367, seals 2368-4, 2368-5, 2368-6, primary control valve 2320-2 with stabilizer 2373, and stabilizer 2373. In various embodiments, the distal end of primary control valve 2320-1 may be inserted into the proximal end of primary control valve 2320-2 to assemble primary control valve 2320, such as via press-fitting. The stabilizer 2373 may assist in keeping the primary control valve 2320 centered in an AW valve well. Further, the shape of the stabilizer 2373 may enable fluid flow to still pass around the stabilizer in the AW valve well.

In various embodiments, one or more components, or features thereof, of environment 2300C may provide one or more of a seat, attachment member, retention member, positioning member, manufacturing fixture, and/or the like for one or more other components of the AW valve assembly 2302. For example, flange 2371 may provide a seat for a biasing member. In another example, the bowl 2364, hat 2358, and/or primary control valve 2320 may include one or more seats for flow components 2369 or seals 2368. In a further example, the flow component 2369-1 may couple with features of the bowl 2364.

In several embodiments, the coupler 2389 may enable or include a snap-fit or press-fit with interface member 2352. In many embodiments, the coupler 2389 may enable or include a snap-fit biopsy port interface. In some embodiments, the flange 2371 and primary control valve 2320-1 may provide a spring stanchion. The assembled relationships between various components is illustrated in FIG. 23D.

Figure 23D:
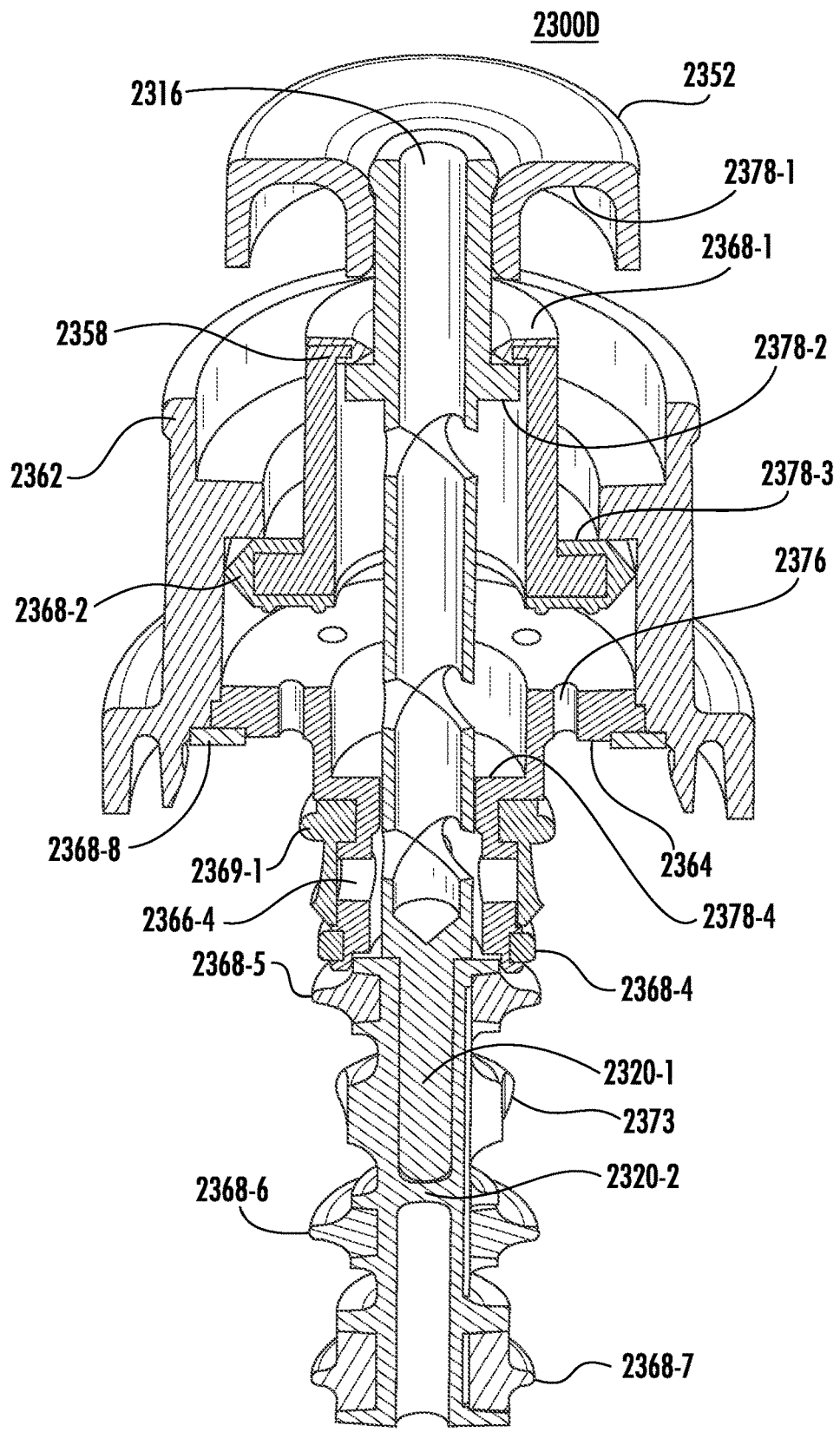

Referring to FIG. 23D, environment 2300D illustrates a cross-sectional view of AW valve assembly 2302. In the illustrated embodiment, the assembled relationships between components of the AW valve assembly 2302 is shown. In various embodiments, the interface member 2352 may include a first biasing member seat 2378-1, the flange 2371 of primary control valve 2320-1 may include a second biasing member seat 2378-2, the hat 2358 and/or flow component 2369-2 may include a third biasing member seat 2378-3, and the bowl 2364 may include a fourth biasing member seat 2378-4. In one or more embodiments, a first biasing member (e.g., spring) may sit between biasing member seats 2378-1, 2378-3 while a second biasing member may sit between biasing member seats 2378-2, 2378-4.

In many embodiments, the primary control valve 2320 may move up and down with respect to bowl 2364 and an AW valve well to control fluid flow through the AW valve well. As previously mentioned, and described, fluid control through the AW valve well may include an air escape state, an air delivery state, a water delivery state, and a balloon fill state (see e.g., FIGS. 4A-4E).

In the air escape state, air from an air input channel may enter the housing 2362 through the one or more vertical holes 2376. Next, the air may pass through radial holes of the primary control valve and out atmospheric channel 2316. In the air escape state, the pressure within the lumen of primary control valve 2320 may not be sufficient to allow air to escape via flapper 2367 of flow component 2369-1.

The air delivery state may include a similar flow path as the air escape state except that the atmospheric channel 2316 is blocked. Accordingly, sufficient pressure is able to build up within the lumen of primary control valve 2320 to allow air to escape via flapper 2367 of flow component 2369-1 and out of radial holes 2366-4 of bowl 2364. The air may then exit into the air output channel of an AW valve well. Further, seal 2368-3, 2368-4, and/or seal 2368-5 may prevent the air from moving elsewhere in the valve well instead of into the air output channel of an AW valve well.

In the water delivery state, the air input channel may be blocked by hat 2358 and flow component 2369-2 covering the one or more vertical holes 2376. In the water delivery state, the seal 2368-5, 2868-6, 2368-7 may be arranged in the same or similar manner as illustrated in FIG. 12B. The balloon fill state may include a similar air flow path as the water delivery state. Further, In the balloon fill state, the seal 2368-5, 2868-6, 2368-7 may be arranged in the same or similar manner as illustrated in FIG. 12C.

The medical devices of the present disclosure are not limited, and may include a variety of medical devices for accessing body passageways, including, for example, duodenoscopes, catheters, ureteroscopes, bronchoscopes, colonoscopes, arthroscopes, cystoscopes, hysteroscopes, EUS endoscopes, and the like. In various embodiments, the valve assemblies, or components thereof, described herein may include one or more (e.g., as a single or set of units) of a mounting point, mechanical coupler, bearing, seal, O-ring, actuator, valve, diaphragm, gasket, housing, connector, structural member, manifold, ergonomic features (e.g., finger/thumb grooves, padding, grip, application of mechanical advantage, and the like), spring, bellow, cantilever biasing member, torsional biasing member, linear biasing member, flapper valve, skirt, fin, disc, channel, cavity, lumen, and the like. In many embodiments, one or more components described herein may be constructed utilizing a variety of devices, technologies and/or processes, such as three-dimensional (3D) printing, multi-axis computer numeric control (CNC) machines, additive manufacturing, subtractive manufacturing, injection molding, overmolding, computer aided design (CAD) programs, path planning programs, machining, forging, casting, and the like.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device, comprising:
 a valve well comprising a water input channel, a water output channel, a balloon channel, an air input channel, an atmospheric channel, and an air output channel,
 a valve set including a primary control valve, an air input valve, and an atmospheric valve, the primary control valve configured to control flow between the water input channel, the water output channel, and the balloon channel of the valve well, the air input valve configured to control flow through the air input channel of the valve well, and the atmospheric valve configured to control flow through the atmospheric channel, wherein the primary control valve comprises the air input valve; and
 a valve interface mechanism including a set of one or more biasing members and a user interface mechanism, the user interface mechanism operable between a first state, a second state, a third state, and a fourth state, the first state comprising the valve set configured to place the air input channel in fluid communication with the atmospheric channel, the second state comprising the valve set configured to place the air input channel in fluid communication with the air output channel, the third state comprising the valve set configured to place the water input channel in fluid communication with the water output channel, and the fourth state comprising the valve set configured to place the water input channel in fluid communication with the balloon channel;

wherein the primary control valve comprises a set of seals, wherein a first subset of the set of seals is configured to control flow through the air input channel of the valve well by moving from a first position in which air is blocked-from the air input channel to a second position in which air is permitted into the air input channel and a second subset of the set of seals is configured to control flow between the water input channel, the water output channel, and the balloon channel of the valve well, and wherein the valve interface mechanism comprises a hat with a top side and a bottom side and the set of one or more biasing members comprises first and second biasing members disposed on the top side of the hat.

2. The medical device of claim 1, the primary control valve comprising a set of radial seals, wherein a first subset of the set of radial seals comprise the air input valve.

3. The medical device of claim 2, wherein each seal in the first subset of the set of seals creates a seal with one or more portions of the valve interface mechanism.

* * * * *